US012688464B2

(12) United States Patent
Kawabata et al.

(10) Patent No.: US 12,688,464 B2
(45) Date of Patent: Jul. 21, 2026

(54) MACHINE LEARNING MODEL, PROGRAM, ULTRASOUND DIAGNOSTIC APPARATUS, ULTRASOUND DIAGNOSTIC SYSTEM, IMAGE PROCESSING APPARATUS, AND TRAINING APPARATUS

(71) Applicant: Konica Minolta, Inc., Tokyo (JP)

(72) Inventors: Akihiro Kawabata, Tokyo (JP); Hiroaki Matsumoto, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 121 days.

(21) Appl. No.: 18/602,562

(22) Filed: Mar. 12, 2024

(65) Prior Publication Data

US 2024/0311695 A1 Sep. 19, 2024

(30) Foreign Application Priority Data

Mar. 13, 2023 (JP) ................................. 2023-038382

(51) Int. Cl.
*G06N 20/00* (2019.01)
*A61B 8/00* (2006.01)
(Continued)

(52) U.S. Cl.
CPC ........... *G06N 20/00* (2019.01); *A61B 8/5223* (2013.01); *G06T 7/0016* (2013.01); *G06T 7/13* (2017.01);
(Continued)

(58) Field of Classification Search
CPC ...... G06N 20/00; G06N 3/045; G06N 3/0464; G06N 3/084; A61B 8/5223; A61B 8/06;
(Continued)

(56) References Cited

U.S. PATENT DOCUMENTS

2011/0021915 A1 1/2011 Feng et al.
2017/0116497 A1* 4/2017 Georgescu ............. G06N 3/006
(Continued)

FOREIGN PATENT DOCUMENTS

JP 2006-181058 A 7/2006
JP 2006-197969 A 8/2006
(Continued)

OTHER PUBLICATIONS

Notice of Reasons of Refusal, dated Feb. 25, 2025, for the corresponding Japanese Patent Application No. 2023-038382, with its English translation, 11 pages.
(Continued)

*Primary Examiner* — Bo Joseph Peng
(74) *Attorney, Agent, or Firm* — LUCAS & MERCANTI, LLP

(57) ABSTRACT

Techniques for efficiently generating time-varying image data for use in training a machine learning model are disclosed. An aspect of the present disclosure relates to a machine learning model trained using training data that includes at least one piece of training time-varying image data of second time-varying image data and third time-varying image data, the second time-varying image data being obtained by standardizing first time-varying image data in a time direction, the first time-varying image data being based on a reception signal for image generation received by an ultrasound probe, third time-varying image data being based on the second time-varying image data, and, and ground truth data including a detection target corresponding to the at least one piece of training time-varying image data.

21 Claims, 57 Drawing Sheets

(51) Int. Cl.

| | |
|---|---|
| *G06T 7/00* | (2017.01) |
| *G06T 7/13* | (2017.01) |
| *G06T 7/62* | (2017.01) |
| *G06T 7/73* | (2017.01) |
| *G16H 30/40* | (2018.01) |
| *G16H 50/20* | (2018.01) |

(52) U.S. Cl.
  CPC .................. *G06T 7/62* (2017.01); *G06T 7/73* (2017.01); *G16H 30/40* (2018.01); *G16H 50/20* (2018.01); *G06T 2207/10132* (2013.01); *G06T 2207/20081* (2013.01); *G06T 2207/30104* (2013.01)

(58) Field of Classification Search
  CPC ..... A61B 8/0883; A61B 8/0891; A61B 8/488; A61B 8/5207; A61B 8/48; A61B 8/543; G06T 7/0016; G06T 7/13; G06T 7/62; G06T 7/73; G06T 2207/10132; G06T 2207/20081; G06T 2207/30104; G06T 7/0012; G06T 2207/20084; G16H 30/40; G16H 50/20; G06V 2201/03; G06V 10/62; G06V 10/778; G06V 10/774; G06V 10/82
  See application file for complete search history.

(56) References Cited

U.S. PATENT DOCUMENTS

| | | | | |
|---|---|---|---|---|
| 2017/0337682 A1* | 11/2017 | Liao | ............................. | G06T 7/30 |
| 2018/0137633 A1* | 5/2018 | Chang | ..................... | G06N 3/045 |
| 2018/0232878 A1* | 8/2018 | Braun | ........................ | G06T 7/20 |
| 2019/0332942 A1* | 10/2019 | Wang | ....................... | G06F 17/13 |
| 2021/0397886 A1* | 12/2021 | Chen | ....................... | G06V 10/82 |
| 2024/0311695 A1* | 9/2024 | Kawabata | ................. | G06T 7/13 |

FOREIGN PATENT DOCUMENTS

| | | |
|---|---|---|
| JP | 2020-075104 A | 5/2020 |
| JP | 2021-164533 A | 10/2021 |
| JP | 2021-164572 A | 10/2021 |

OTHER PUBLICATIONS

Notice of Reasons of Refusal ("Communication") issued on Oct. 22, 2024, for the corresponding Japanese Patent Application No. 2023-038382, with an English translation.

\* cited by examiner

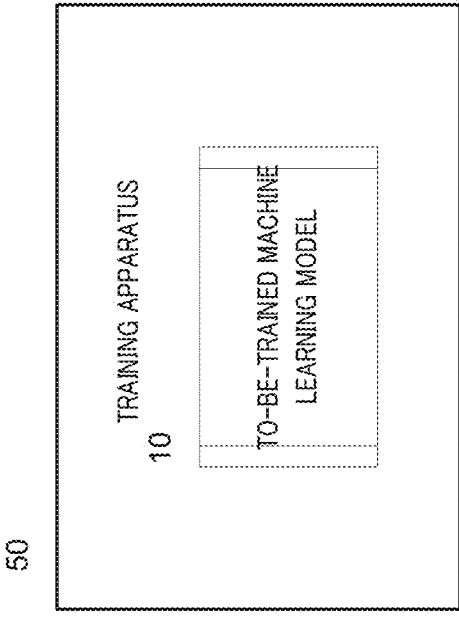
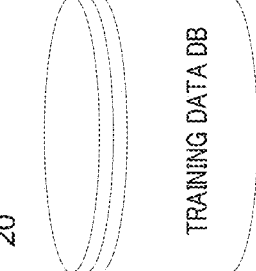
FIG. 3

INFERENCE RESULT

10

TRAINED MACHINE LEARNING MODEL

STANDARDIZED PREDICTION
TARGET TIME-VARYING
IMAGE DATA

FIG. 4

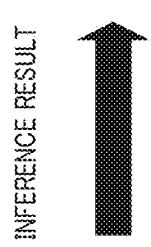
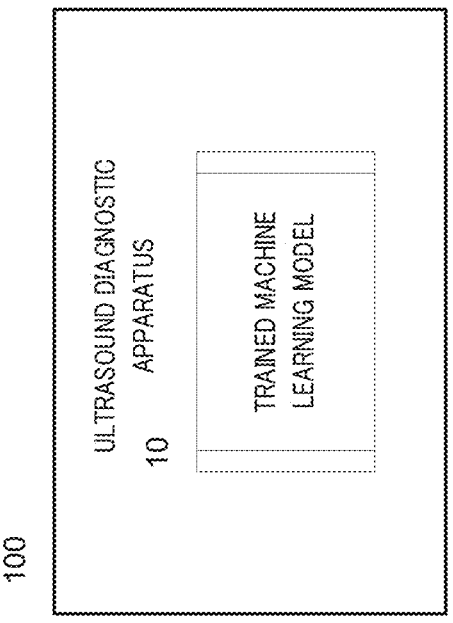
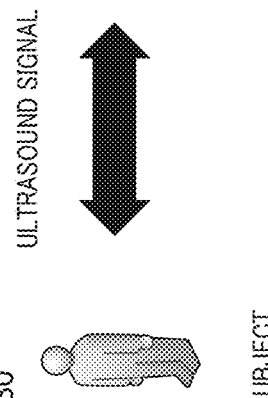
FIG. 5

50

100

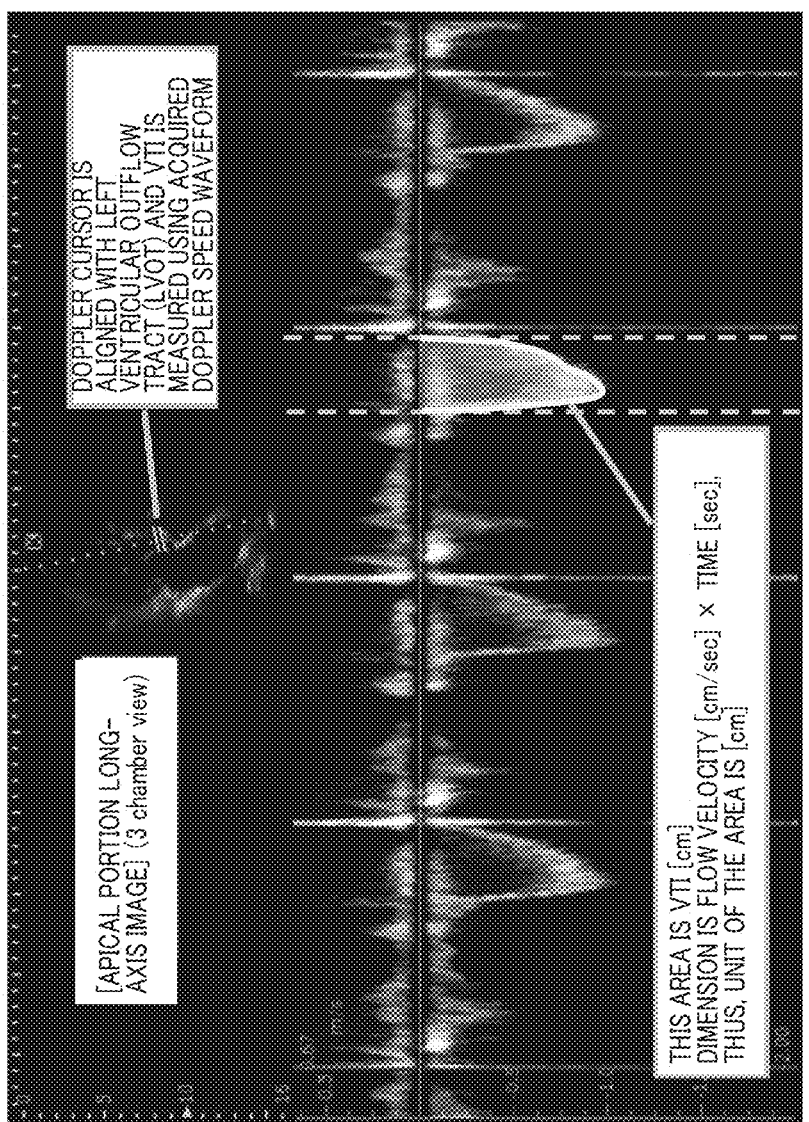
DOPPLER CURSOR IS ALIGNED WITH LEFT VENTRICULAR OUTFLOW TRACT (LVOT) AND VTI IS MEASURED USING ACQUIRED DOPPLER SPEED WAVEFORM
[APICAL PORTION LONG-AXIS IMAGE] (3 chamber view)
THIS AREA IS VTI [cm]
DIMENSION IS FLOW VELOCITY [cm/sec] × TIME [sec]
THUS, UNIT OF THE AREA IS [cm]
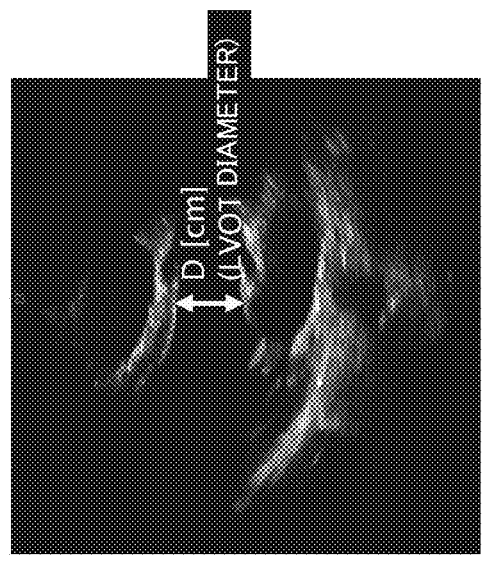
D [cm]
(LVOT DIAMETER)
FIG. 16

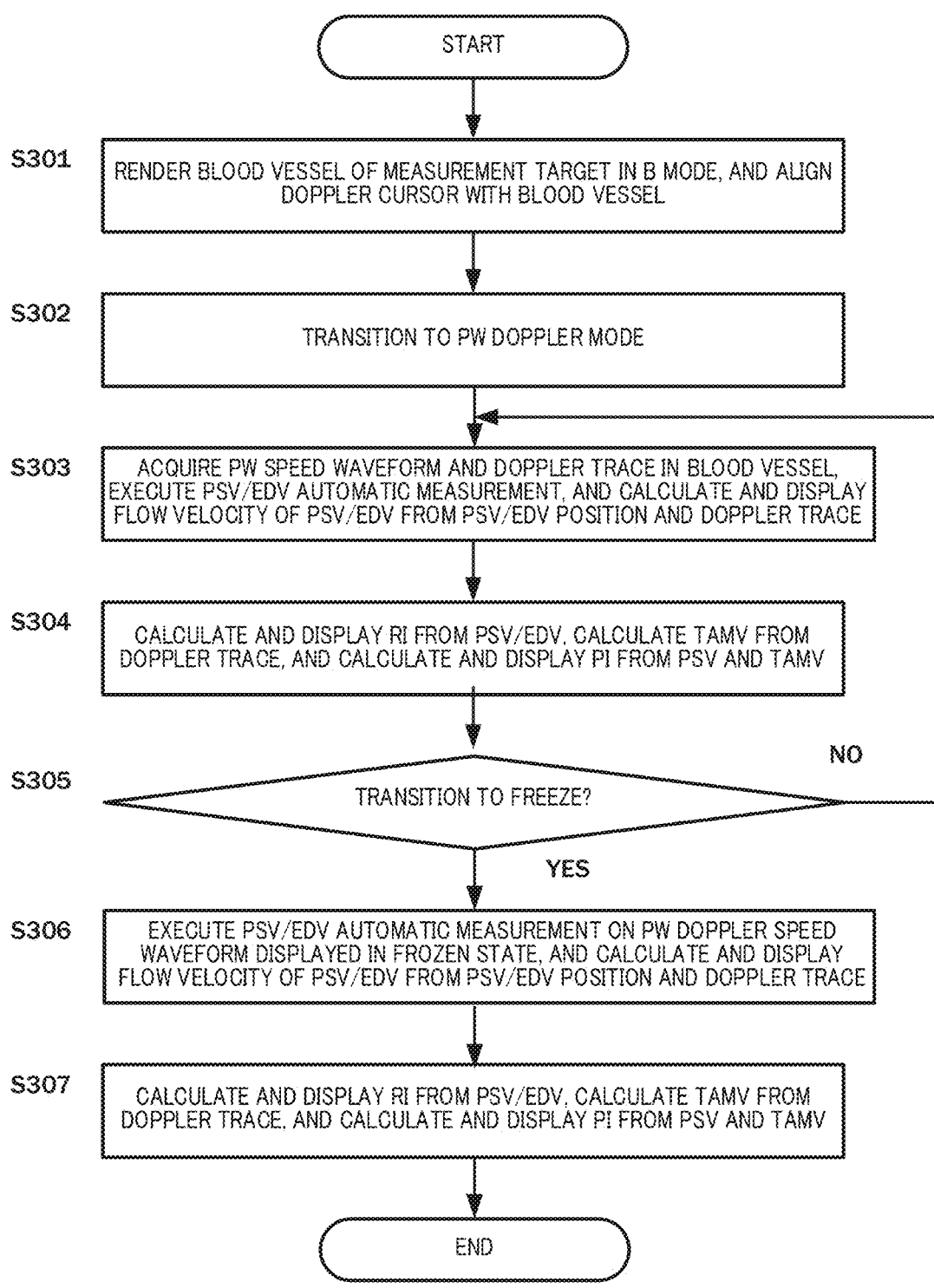

S301 — RENDER BLOOD VESSEL OF MEASUREMENT TARGET IN B MODE, AND ALIGN DOPPLER CURSOR WITH BLOOD VESSEL

S302 — TRANSITION TO PW DOPPLER MODE

S303 — ACQUIRE PW SPEED WAVEFORM AND DOPPLER TRACE IN BLOOD VESSEL, EXECUTE PSV/EDV AUTOMATIC MEASUREMENT, AND CALCULATE AND DISPLAY FLOW VELOCITY OF PSV/EDV FROM PSV/EDV POSITION AND DOPPLER TRACE

S304 — CALCULATE AND DISPLAY RI FROM PSV/EDV, CALCULATE TAMV FROM DOPPLER TRACE, AND CALCULATE AND DISPLAY PI FROM PSV AND TAMV

S305 — TRANSITION TO FREEZE? — NO / YES

S306 — EXECUTE PSV/EDV AUTOMATIC MEASUREMENT ON PW DOPPLER SPEED WAVEFORM DISPLAYED IN FROZEN STATE, AND CALCULATE AND DISPLAY FLOW VELOCITY OF PSV/EDV FROM PSV/EDV POSITION AND DOPPLER TRACE

S307 — CALCULATE AND DISPLAY RI FROM PSV/EDV, CALCULATE TAMV FROM DOPPLER TRACE, AND CALCULATE AND DISPLAY PI FROM PSV AND TAMV

FIG. 28

BOUNDARY OF MEASUREMENT TARGET SECTION (ONE HEARTBEAT SECTION) FOR FLOW VOLUME MEASUREMENT IS DETEDCTED
(THE BOUNDARY IS DETECTED BECAUSE MEASUREMENT TARGET SECTION IS CONTINUOUS WITH NEIGHBORING HEARTBEATS)
USUALLY EDV TIMING IS USED AS HEARTBEAT BOUNDARY

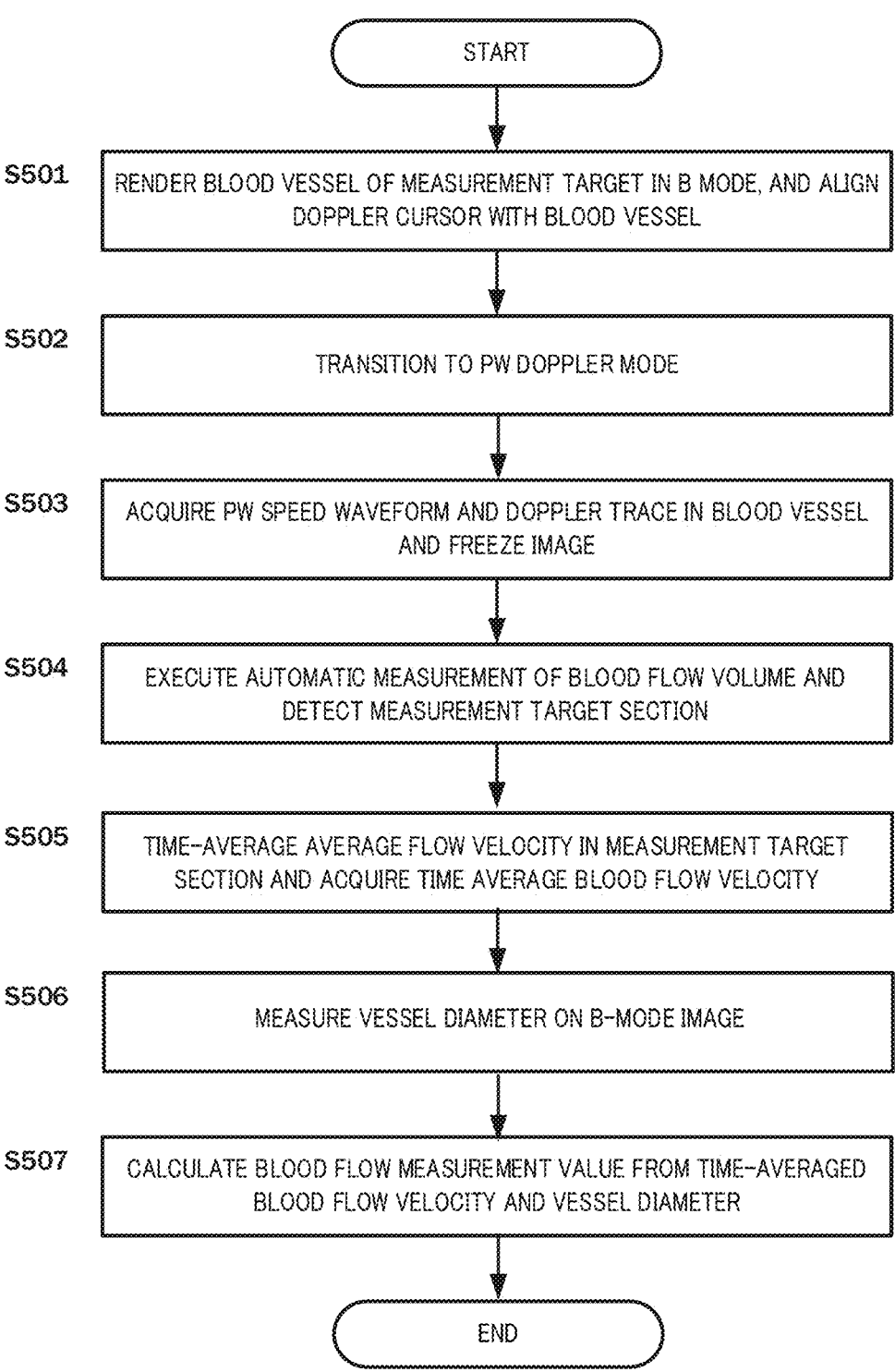

START

S501    RENDER BLOOD VESSEL OF MEASUREMENT TARGET IN B MODE, AND ALIGN DOPPLER CURSOR WITH BLOOD VESSEL

S502    TRANSITION TO PW DOPPLER MODE

S503    ACQUIRE PW SPEED WAVEFORM AND DOPPLER TRACE IN BLOOD VESSEL AND FREEZE IMAGE

S504    EXECUTE AUTOMATIC MEASUREMENT OF BLOOD FLOW VOLUME AND DETECT MEASUREMENT TARGET SECTION

S505    TIME-AVERAGE AVERAGE FLOW VELOCITY IN MEASUREMENT TARGET SECTION AND ACQUIRE TIME AVERAGE BLOOD FLOW VELOCITY

S506    MEASURE VESSEL DIAMETER ON B-MODE IMAGE

S507    CALCULATE BLOOD FLOW MEASUREMENT VALUE FROM TIME-AVERAGED BLOOD FLOW VELOCITY AND VESSEL DIAMETER

END

FIG. 35

MACHINE LEARNING MODEL, PROGRAM, ULTRASOUND DIAGNOSTIC APPARATUS, ULTRASOUND DIAGNOSTIC SYSTEM, IMAGE PROCESSING APPARATUS, AND TRAINING APPARATUS

CROSS REFERENCE TO RELATED APPLICATIONS

The entire disclosure of Japanese Patent Application No. 2023-038382 filed on Mar. 13, 2023, is incorporated herein by reference in its entirety.

BACKGROUND

Technological Field

The present disclosure relates to a machine learning model, a program, an ultrasound diagnostic apparatus, an ultrasound diagnostic system, an image processing apparatus, and a training apparatus.

Description of the Related Art

With the recent development of deep learning technology, machine learning models have come to be used for various purposes. For example, in the medical field, attempts have been made to use machine learning for diagnostic imaging such as ultrasonic diagnosis.

A typical ultrasound diagnostic apparatus can operate in two modes: a Doppler mode and an M mode, in addition to a B mode for displaying a tomographic image and a color Doppler mode for displaying a blood flow image. The Doppler mode is an image mode for spectrally displaying a speed change of a blood flow (tissue). Examples thereof include a pulse wave Doppler (Pulse Wave Doppler: PWD), continuous wave Doppler (CWD), and tissue Doppler (Tissue Doppler Imaging: TDI). On the other hand, the M mode is a mode in which a temporal change of one line on a tomographic image (B mode) is displayed. Various diagnostic imaging techniques using ultrasonic images have been proposed.

SUMMARY

In the Doppler mode, when the sweep speed of the ultrasound diagnostic apparatus is different, the width of the spectrum in the time direction in an ultrasonic image may differ even for the same subject. When the sweep speed is low, the spectrum contracts in the time direction in the ultrasonic image, and when the sweep speed is high, the spectrum expands in the time direction. Furthermore, the heart rate (HR) may vary depending on the subject. When the heartbeat is fast, the spectrum in the ultrasound image is narrowed in the time direction, and when the heartbeat is slow, the spectrum is spread out in the time direction.

Also in the M mode, when the sweep speed is low, the M mode image contracts in the time direction, and when the sweep speed is high, the M mode image expands in the time direction. In addition, when the heartbeat is high, the M-mode image is narrowed in the time direction, and when the heartbeat is low, the M-mode image expands in the time direction.

In the time-varying image mode such as the Doppler mode or the M mode, the time-varying image data changes so as to be expanded or contracted in the time direction, depending on settings such as the sweep speed. Therefore, in a case where an artificial intelligence (AI) model is applied to automatic measurement on a time-varying image, patterns required to train the AI model increase due to a difference in sweep speed. For this reason, learning data (training data) of time-varying images needs to be prepared for each sweep speed, and when the amount of training data is small, the performance of the AI processing may decrease.

In addition, in the time-varying image mode, even when the sweep speed is the same, the acquired data may appear to change in expansion and contraction in the time direction when the heart rate of a subject is different. Therefore, a difference in heart rate can also cause a similar problem to the above-described difference in the sweep speed.

In consideration of the above-described problem, an object of the present disclosure is to provide a technique for efficiently generating time-varying image data to be used in the training of a machine learning model.

To achieve at least one of the abovementioned objects, according to an aspect of the present invention, an aspect of the present disclosure relates to a machine learning model trained by using training data including the following data: at least one piece of training time-varying image data of second time-varying image data and third time-varying image data, the second time-varying image data being obtained by standardizing first time-varying image data in a time direction, the first time-varying image data being based on a reception signal for image generation received by an ultrasound probe, third time-varying image data being based on the second time-varying image data, and ground truth data including a detection target corresponding to the at least one piece of training time-varying image data.

BRIEF DESCRIPTION OF DRAWINGS

The advantages and features provided by one or more examples of the invention will become more fully understood from the detailed description given hereinbelow and the appended drawings which are given by way of illustration only, and thus are not intended as a definition of the limits of the present invention:

FIG. 3 is a schematic diagram illustrating training processing of a machine learning model according to the example of the present disclosure;

FIG. 4 is a schematic diagram illustrating inference processing of the machine learning model according to the example of the present disclosure;

FIG. 5 is a schematic diagram illustrating ultrasound diagnostic processing according to the example of the present disclosure;

FIG. 16 is a diagram illustrating VTI measurement processing according to the example of the present disclosure;

FIG. 28 is a flowchart illustrating PSV and EDV measurement processing according to an example of the present disclosure;

FIG. 35 is a flowchart illustrating blood flow volume measurement processing according to an example of the present disclosure;

DETAILED DESCRIPTION OF EMBODIMENTS

Hereinafter, one or more examples of the present invention will be described with reference to the drawings. However, the scope of the invention is not limited to the disclosed examples.

The following examples disclose an image processing apparatus using a machine learning model that outputs a detection target from a time-varying image acquired from a subject.

Overview

Figure 1:
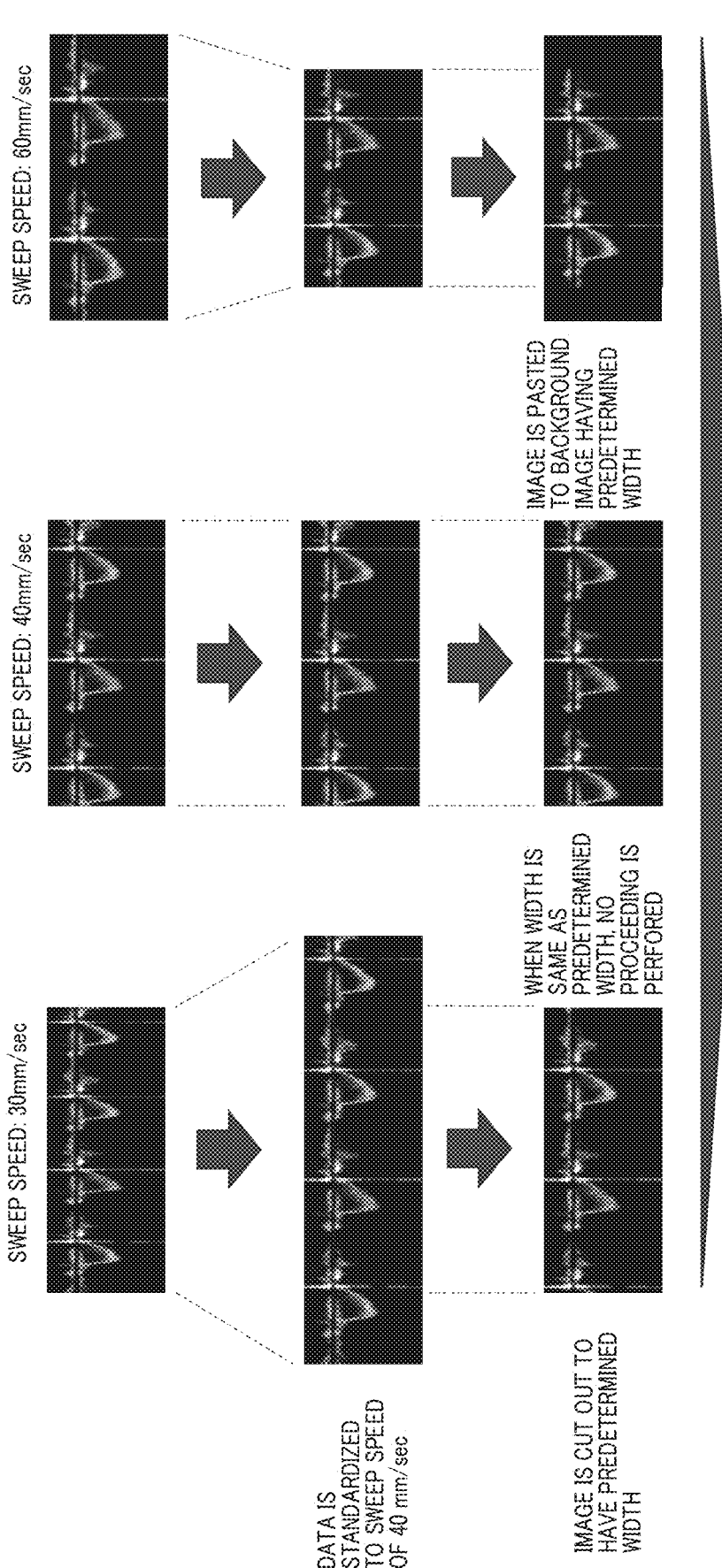
FIG. 1 is a schematic diagram illustrating standardization of training data according to an example of the present disclosure.

In general, it is known that time-varying images acquired by an ultrasound diagnostic apparatus at different sweep speeds are different even for the same subject. For example, FIG. 1 illustrates time-varying images acquired at three sweep speeds of 30 mm/sec, 40 mm/sec, and 60 mm/sec. Three time-varying images show that the widths of the spectra in the time direction are different. That is, when the sweep speed is low, the spectrum on the time-varying image is contracted in the time direction, and when the sweep speed is high, the spectrum is expanded in the time direction. In other words, the spectrum of the time-varying image at 30 mm/sec is smaller in the time direction than the spectrum of the time-varying image at 60 mm/sec. As described above, in a time-varying image mode such as Doppler mode or M mode of an ultrasound diagnostic apparatus, an acquired time-varying image may be expanded or contracted in the time direction depending on a sweep speed set by a user. Therefore, when a machine learning model is applied to time-varying image data, the number of patterns required for training the machine learning model increases due to the difference in the sweep speed, and training data for various sweep speeds needs to be prepared in order to satisfy satisfactory model prediction performance.

In the following example, data expansion is executed on time-varying image data acquired by an image diagnostic apparatus, and the time-varying image data is standardized to a predetermined sweep speed. The training processing and inference processing for the machine learning model are executed by using the standardized time-varying image. For example, as illustrated in FIG. 1, two pieces of training time-varying image data of 30 mm/sec and 60 mm/sec are standardized by a sweep speed of 40 mm/sec. To be more specific, when the time-varying image at the sweep speed $SS_1$ is standardized to the predetermined sweep speed $SS_0$, the time-varying image at the sweep speed $SS_1$ is enlarged or reduced $SS_0/SS_1$ times in the time axis direction, i.e., in the width direction of the image. That is, as illustrated in FIG. 1, the time-varying image acquired at the sweep speed of 30 mm/sec is enlarged by 40/30 (1.33) times, and the time-varying image acquired at the sweep speed of 60 mm/sec is reduced by 40/60 (0.66) times. Time-varying images acquired for the same subject at different sweep speeds can be standardized by such standardization.

Thereafter, the enlarged and reduced time-varying images are adjusted to have a predetermined image width. To be specific, as illustrated in FIG. 1, the enlarged time-varying image may be cut out in accordance with the width of the time-varying image at a sweep speed of 40 mm/sec. On the other hand, the reduced time-varying image may be pasted on a background image having a width of the time-varying image at a sweep speed of 40 mm/sec.

In this manner, it is possible to acquire training data of a machine learning model by using time-varying image data at a predetermined sweep speed standardized from time-varying image data acquired at a different sweep speed. Accordingly, it is not necessary to prepare time-varying image data of each sweep speed as the training data, and it is possible to train the machine learning model by time-varying image data of a smaller number of samples. When a machine learning model trained with standardized time-varying image data is used for inference processing, the time-varying image data of an inference target is pre-processed so as to be enlarged or reduced to time-varying image data at a predetermined sweep speed, and then input to the trained machine learning model.

Figure 2:
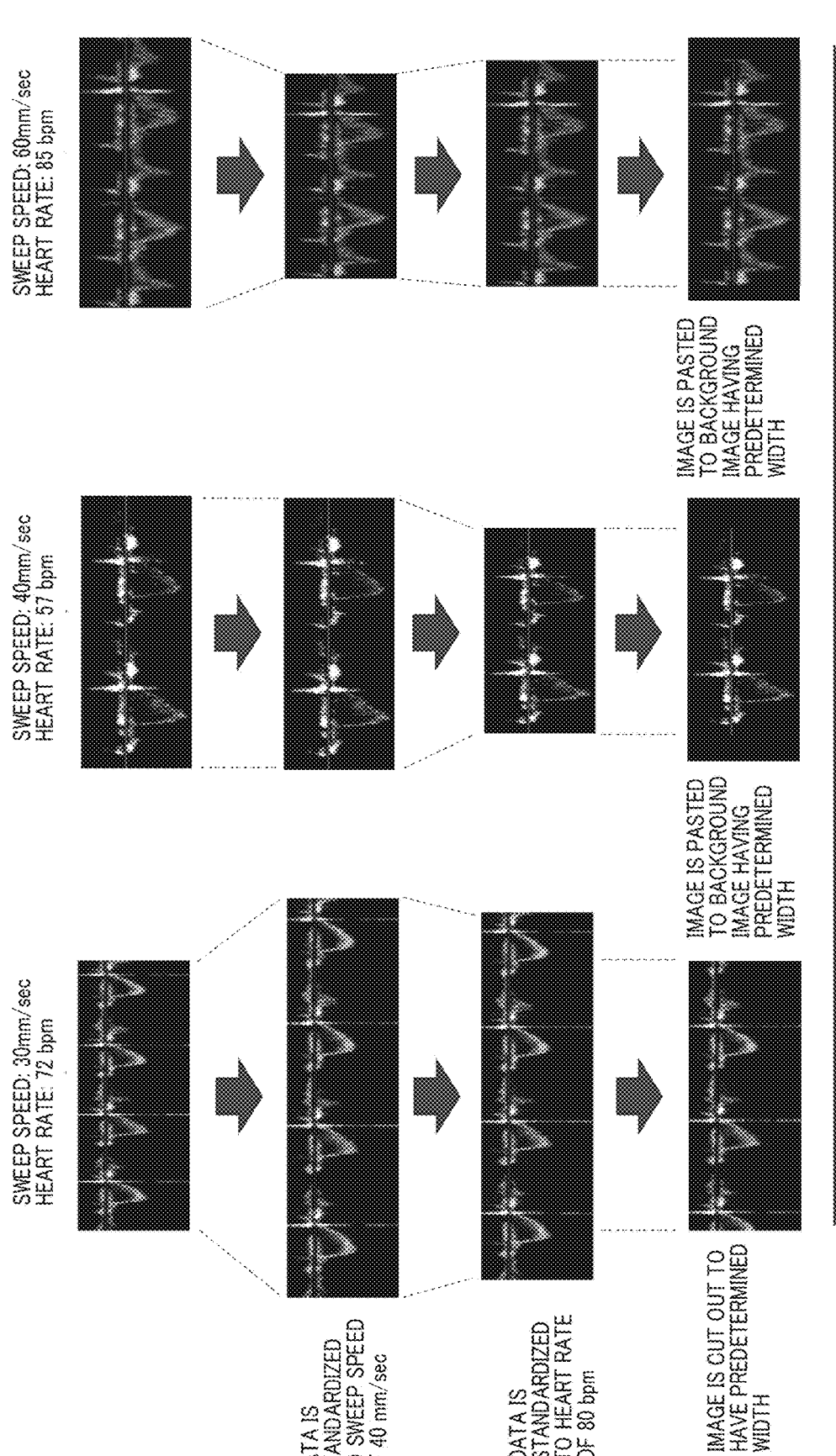
FIG. 2 is a schematic diagram illustrating standardization of training data according to the example of the present disclosure.

In addition, for time-varying images acquired for different subjects and/or different heart rates, the time-varying image data is first standardized to a predetermined sweep speed. As illustrated in FIG. 2, the time-varying image data may be standardized to a sweep speed of 40 mm/sec. Next, the time-varying image data standardized with respect to the sweep speed may be standardized to have a predetermined heart rate. Here, the standardization regarding the heart rate may be executed by enlarging or reducing the time-varying image in the time axis direction, that is, in the width direction of the image, in a similar manner to the standardization regarding the sweep speed described above. In the example illustrated in FIG. 2, the time-varying image data may be standardized to have a heart rate of 80 bpm.

Thereafter, the enlarged and reduced time-varying images are adjusted to have a predetermined image width. To be more specific, as illustrated in FIG. 2, the enlarged time-varying image may be cut out in accordance with the width of the predetermined time-varying image. On the other hand, the reduced time-varying image may be pasted on the background image having a predetermined width of the time-varying image.

In this manner, it is possible to acquire training data of a machine learning model by using time-varying image data standardized from time-varying image data acquired at different sweep speeds and heart rates. Accordingly, it is not necessary to prepare the time-varying image data of each sweep speed and each heart rate as the training data, and it is possible to train the machine learning model with the time-varying image data of a smaller number of samples. When the machine learning model trained by the standardized time-varying image data is used for the inference processing, the time-varying image data of an inference target is pre-processed in such a way that the time-varying image data of a predetermined sweep speed and/or heart rate is enlarged or reduced, and then input to the trained machine learning model.

For example, when the machine learning model is trained by using the time-varying image data generated by the above-described data expansion, time-varying image data with different sweep speeds and/or heart rates are stored in the training database (DB) 20 in association with ground truth data, and the training apparatus 50 performs the above-described data expansion on the time-varying image data acquired from the training data DB20, to acquire standardized time-varying image data, as illustrated in FIG. 3. The training apparatus 50 trains a machine learning model 10 to be trained by using the standardized time-varying image data. For example, when the machine learning model 10 to be trained is implemented as a certain type of neural network such as a convolutional neural network, the training apparatus 50 inputs the standardized time-varying image data to the neural network to be trained, and updates the parameters of the neural network to be trained in accordance with a certain training algorithm such as an error backpropagation method based on the error between the output result from the neural network and the ground truth data.

Figure 4:
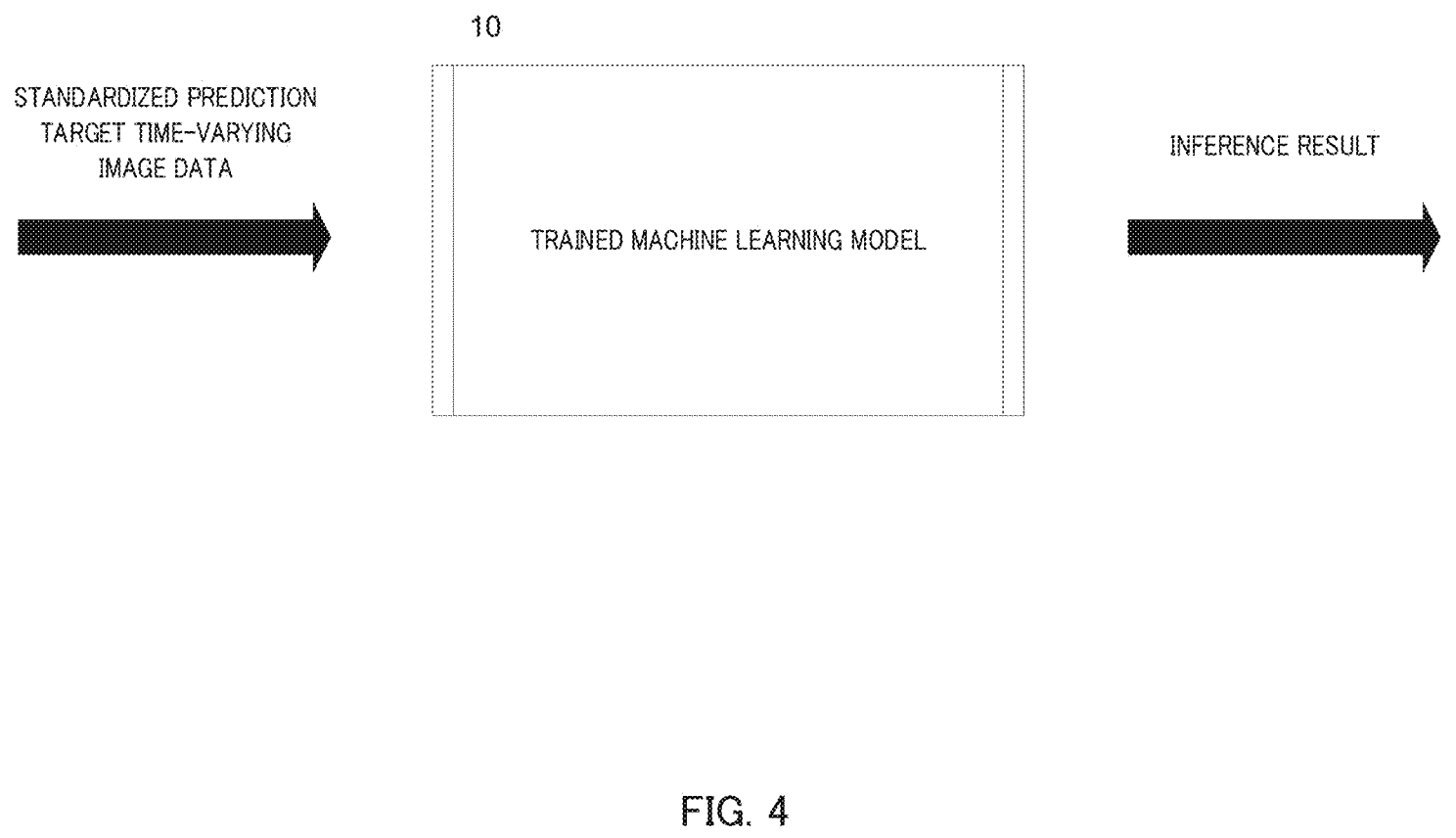

When the training of the machine learning model 10 ends in this manner, the trained machine learning model 10 outputs an inference result when the trained machine learning model 10 receives the standardized time-varying image data from the time-varying image to be predicted, as illustrated in FIG. 4. For example, in ultrasound diagnostics, the inference result may be a particular position, timing, region, or the like, represented by a spectrum on a time-varying image, as described in more detail below. As illustrated in FIG. 5, the ultrasound diagnostic apparatus 100 sends ultrasound signals to a subject 30 and acquires time-varying image data on the basis of reflection signals from the subject 30. The ultrasound diagnostic apparatus 100 standardizes the acquired time-varying image data, inputs the standardized time-varying image to the trained machine learning model 10 provided from the training apparatus 50, and outputs a processing result obtained by performing processing opposite to the preprocessing on the inference result acquired from the trained machine learning model 10.

Figure 6:
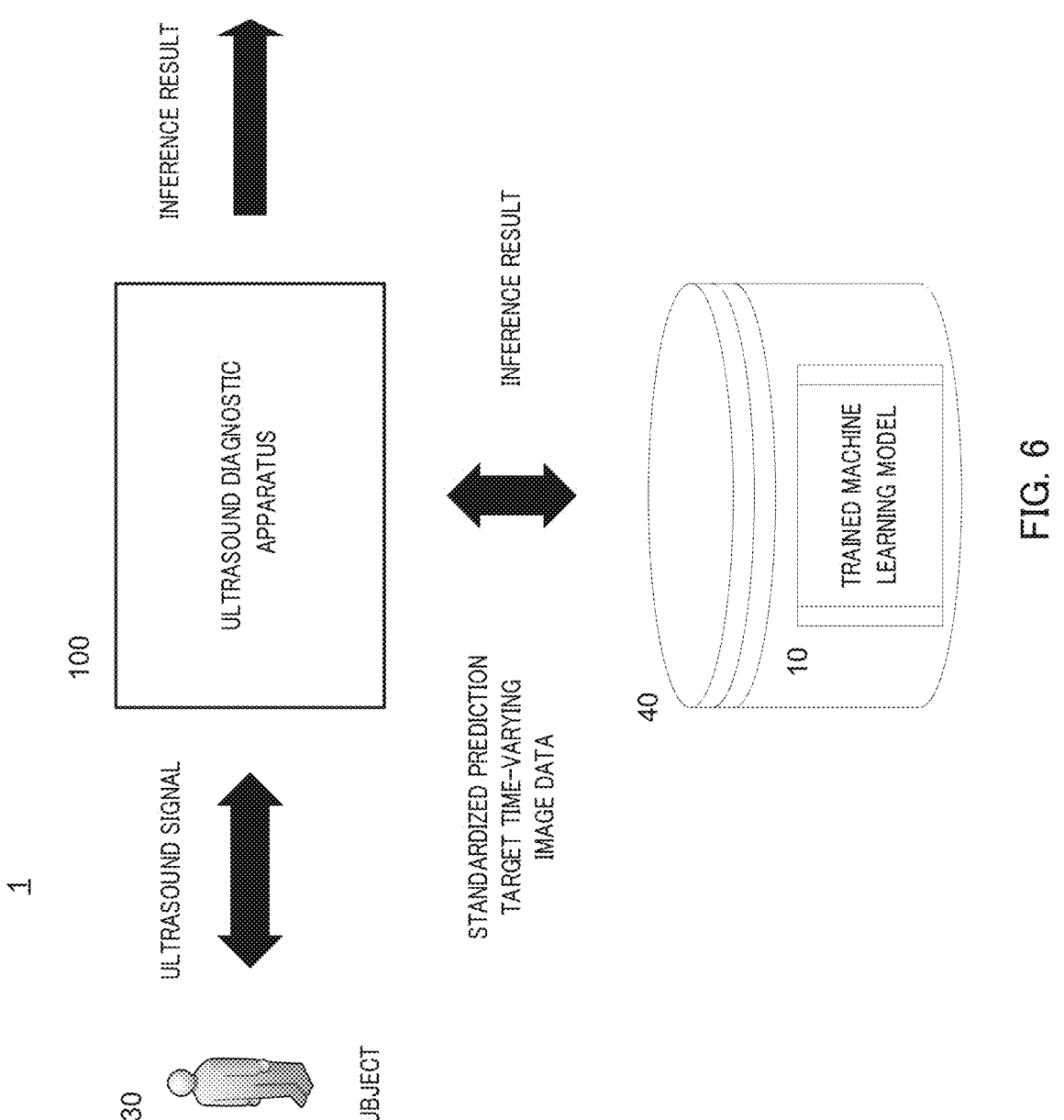
FIG. 6 is a schematic diagram illustrating ultrasound diagnostic processing according to the example of the present disclosure.

Note that although the ultrasound diagnostic apparatus 100 stores the trained machine learning model 10 provided from the training apparatus 50 in the example illustrated in FIG. 5, the ultrasound diagnostic apparatus 100 according to the present disclosure is not necessarily limited thereto and may use the trained machine learning model 10 stored in an external model database (DB) 40 on the cloud or the like, as illustrated in FIG. 6. To be more specific, the ultrasound diagnostic system 1 includes the ultrasound diagnostic apparatus 100 and a model DB40, and the ultrasound diagnostic apparatus 100 standardizes the time-varying image data to be predicted acquired from the subject 30 and sends the standardized time-varying image data to the model DB40. When an inference result for the standardized time-varying image is acquired from the model DB40, the ultrasound diagnostic apparatus 100 may output the acquired inference result.

Figure 7:
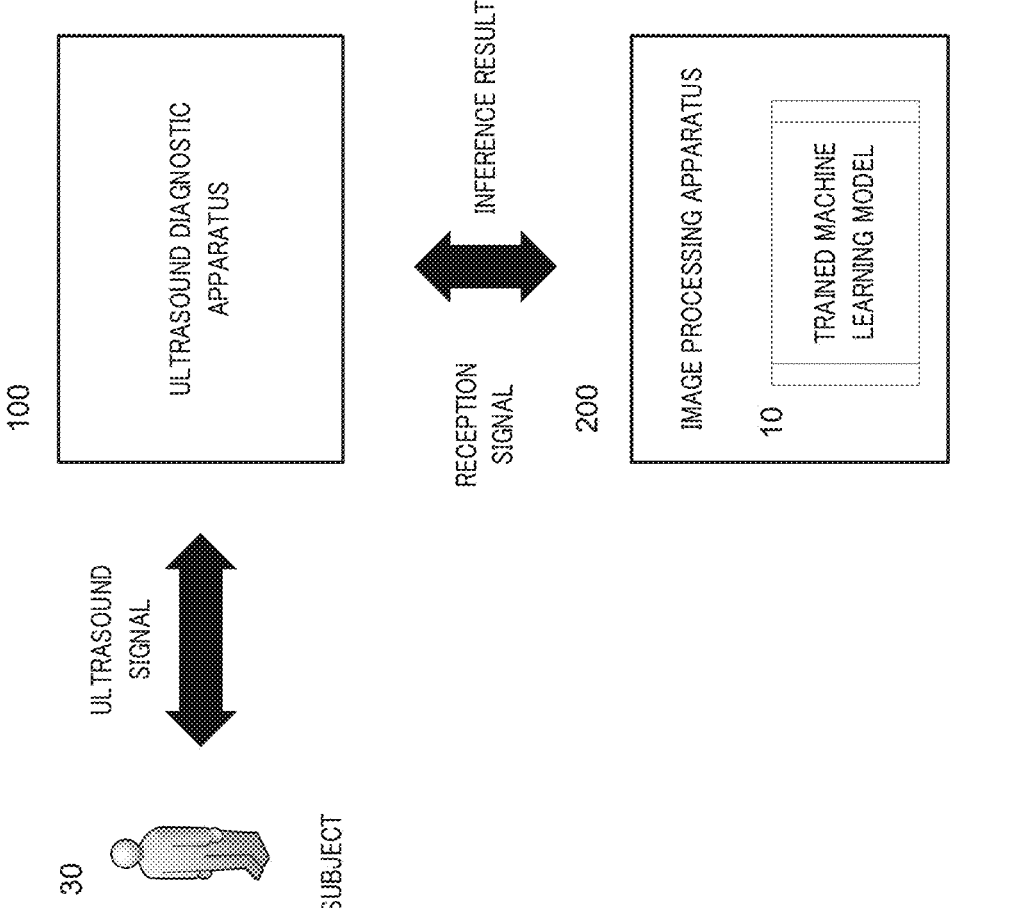
FIG. 7 is a schematic diagram illustrating ultrasound diagnostic processing according to the example of the present disclosure.

Alternatively, as illustrated in FIG. 7, the ultrasound diagnostic apparatus 100 according to the present disclosure may communicate with an external image processing apparatus 200 on the cloud or the like. For example, the ultrasound diagnostic apparatus 100 transmits, to the image processing apparatus 200, a reception signal acquired for an ultrasound signal sent to the subject 30. The image processing apparatus 200 standardizes the reception signal and acquires an inference result from the standardized reception signal using the trained machine learning model 10. The image processing apparatus 200 may store the acquired inference result and/or provide the inference result to the ultrasound diagnostic apparatus 100.

Hardware Configuration of Ultrasound Diagnostic Apparatus

Figure 8:
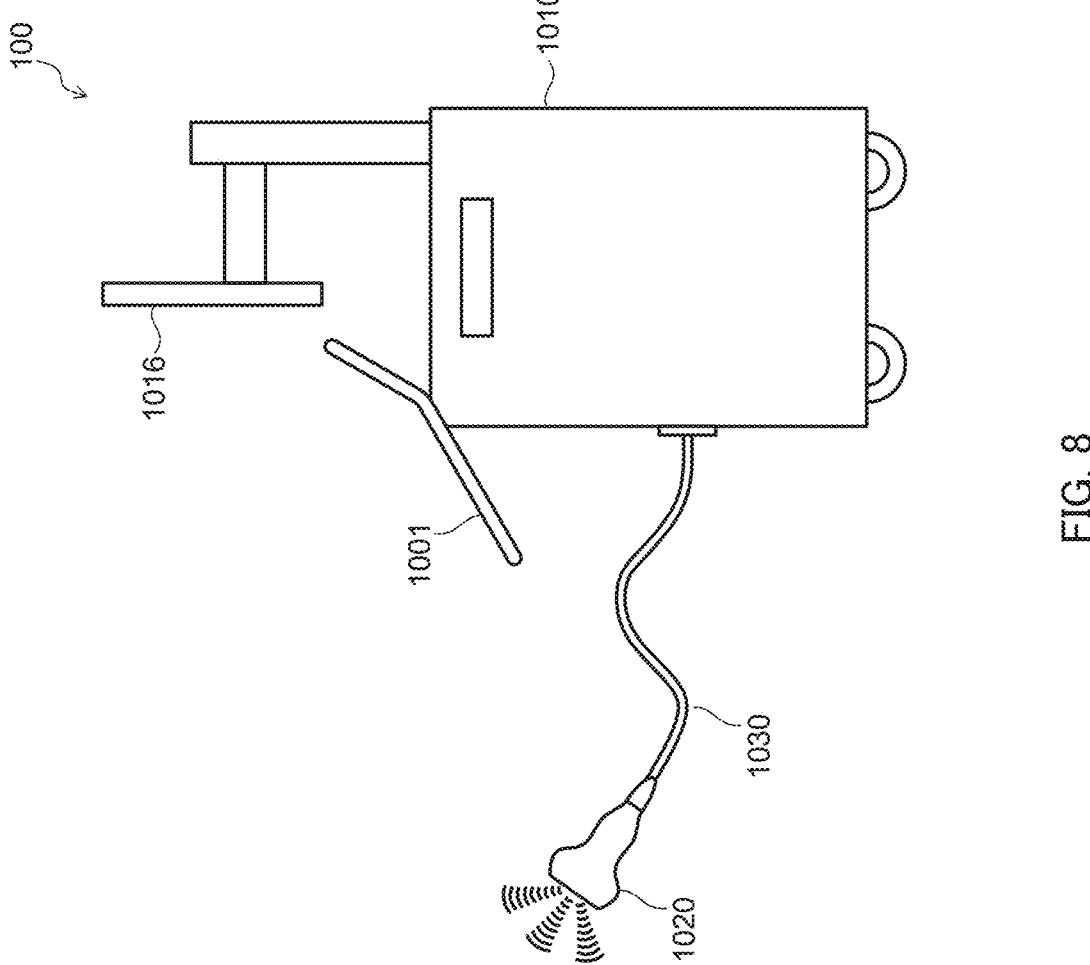
FIG. 8 is a diagram illustrating an appearance of an ultrasound diagnostic apparatus according to the example of the present disclosure.
Figure 9:
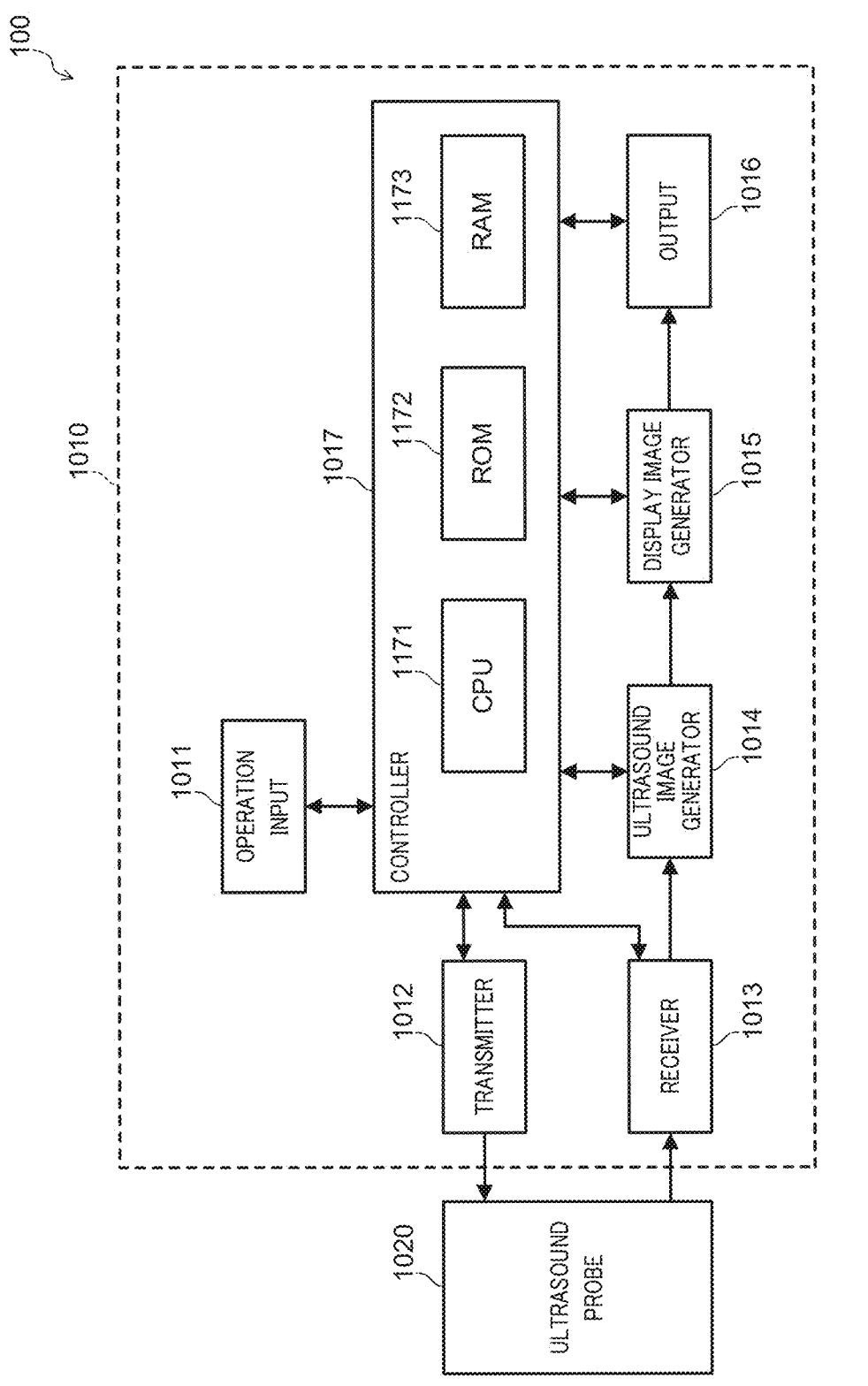
FIG. 9 is a block diagram illustrating a hardware configuration of an ultrasound diagnostic apparatus according to the example of the present disclosure.

FIG. 8 is a diagram illustrating an example of an appearance of the ultrasound diagnostic apparatus 100. FIG. 9 is a block diagram illustrating an example of a configuration of a main part of a control system of the ultrasound diagnostic apparatus 100.

The ultrasound diagnostic apparatus 100 visualizes the shape or dynamics of the inside of the subject 30 as an ultrasound image. The ultrasound diagnostic apparatus 100 according to the present embodiment is used, for example, to take an ultrasonic image (i.e., a tomographic image) of a detection target site and perform an inspection on the detection target site.

As illustrated in FIG. 8, the ultrasound diagnostic apparatus 100 includes an ultrasound diagnostic apparatus main body 1010 and an ultrasound probe 1020. The ultrasound diagnostic apparatus main body 1010 and the ultrasound probe 1020 are connected to each other via a cable 1030.

The ultrasound probe 1020 functions as an acoustic sensor that transmits ultrasonic beams (for example, about 1 to 30 MHz) to the inside of the subject 30 (for example, a human body), receives ultrasonic echoes reflected in the subject 30 among the transmitted ultrasonic beams, and converts the ultrasonic echoes into electric signals.

A user brings the ultrasound beam transmission/reception surface of the ultrasound probe 1020 into contact with the body surface of the detection target site of the subject 30, operates the ultrasound diagnostic apparatus 100 to perform an inspection. As the ultrasound probe 1020, any probe, such as a convex probe, a linear probe, a sector probe, or a three dimensional probe may be used.

The ultrasound probe 1020 is configured to include, for example, a plurality of transducers (e.g., piezoelectric elements) arranged in a matrix, and a channel switching device (e.g., a multiplexer) for controlling switching of on/off of a drive state of the plurality of transducers individually or in units of blocks (hereinafter referred to as "channels").

Each transducer of the ultrasound probe 1020 converts a voltage pulse generated by the ultrasound diagnostic apparatus main body 1010 (a transmitter 1012) into an ultrasonic beam, transmits the ultrasonic beam into the subject 30, receives an ultrasonic echo reflected inside the subject 30, converts the ultrasonic echo into an electric signal (hereinafter referred to as a "reception signal"), and outputs the electric signal to the ultrasound diagnostic apparatus main body 1010 (a receiver 1013).

As illustrated in FIG. 9, the ultrasound diagnostic apparatus main body 1010 includes an operation input 1011, the transmitter 1012, the receiver 1013, an ultrasound image generator 1014, a display image generator 1015, an output 1016, and a controller 1017.

The transmitter 1012, the receiver 1013, the ultrasound image generator 1014, and the display image generator 1015 are formed by dedicated or general-purpose hardware (electronic circuit) corresponding to each processing, such as a digital signal processor (DSP), an application specific integrated circuit (ASIC), or a programmable logic device (PLD), and realize each function in cooperation with the controller 1017.

The operation input 1011 receives, for example, an input of a command instructing the start of diagnosis or the like or information on the subject 30. The operation input 1011 may include, for example, an operation panel including a plurality of input switches, a keyboard, a mouse, and the like. Note that the operation input 1011 May include a touch panel provided integrally with the output 1016.

The transmitter 1012 is a transmitter that sends a voltage pulse as a drive signal to the ultrasound probe 1020 according to an instruction of the controller 1017. The transmitter 1012 may include, for example, a high-frequency pulse oscillator, a pulse setter, and the like. The transmitter 1012 may adjust the voltage pulse generated by the high-frequency pulse oscillator to have a voltage amplitude, a pulse width, and sending timing set by the pulse setter, and sends the voltage pulse for each channel of the ultrasound probe 1020.

The transmitter 1012 includes a pulse setter for each of the plurality of channels of the ultrasound probe 1020, so that the voltage amplitude, pulse width, and sending timing of a voltage pulse can be set for each of the plurality of channels. For example, the transmitter 1012 may change a target depth or generate different pulse waveforms by setting appropriate delay times for a plurality of channels.

The receiver 1013 is a receiver that performs reception processing on a reception signal related to an ultrasonic echo generated by the ultrasound probe 1020 in accordance with an instruction from the controller 1017. The receiver 1013 may include a preamplifier, an AD converter, and a reception beamformer.

The receiver 1013 amplifies a reception signal related to a weak ultrasonic echo for each channel in the preamplifier, and converts the reception signal into a digital signal by the AD converter. Then, the receiver 1013 may collect the reception signals of the plurality of channels into one signal by performing phasing addition on the reception signals of the respective channels in the reception beamformer to obtain acoustic line data.

The ultrasound image generator 1014 acquires the reception signals (acoustic line data) from the receiver 1013 and generates an ultrasonic image (i.e., a tomographic image) of the inside of the subject 30.

For example, when the ultrasound probe 1020 transmits a pulsed ultrasonic beam toward the depth direction, the ultrasound image generator 1014 accumulates, in the line memory, the signal intensity (intensity) of the ultrasonic echoes detected thereafter in a temporally continuous manner. Then, as the ultrasonic beam from the ultrasound probe 1020 scans the inside of the subject 30, the ultrasound image generator 1014 sequentially accumulates the signal intensity of the ultrasonic echo at each scanning position in the line memory, and generates two dimensional data in units of frames. The ultrasound image generator 1014 may then convert the signal intensity of the two dimensional data into a brightness value, to generate an ultrasound image representing a two dimensional structure in a cross section including the transmission direction of the ultrasound and the scanning direction of the ultrasound.

Note that the ultrasound image generator 1014 may include, for example, an envelope detection circuit that performs envelope detection on the reception signal acquired from the receiver 1013, a logarithmic compression circuit that performs logarithmic compression on the signal intensity of the reception signal detected by the envelope detection circuit, and a dynamic filter that removes a noise component included in the reception signal by a band-pass filter whose frequency characteristics are changed according to the depth.

The display image generator 1015 acquires the data of the ultrasonic image from the ultrasound image generator 1014 and generates a display image including a display region of the ultrasonic image. Then, the display image generator 1015 sends the data of the generated display image to the output 1016. The display image generator 1015 may sequentially update the display image each time a new ultrasonic image is acquired from the ultrasound image generator 1014, and cause the output 1016 to display the display image in a moving image format.

Furthermore, the display image generator 1015 may generate, in accordance with an instruction from the controller 1017, a display image (in which a graphic display of time-series data of a detection target is embedded within the display region) together with an ultrasound image.

Note that the display image generator 1015 may generate the display image after performing predetermined image processing, such as coordinate conversion processing and data interpolation processing, on the ultrasonic image output from the ultrasound image generator 1014.

In accordance with an instruction from the controller 1017, the output 1016 acquires data of a display image from the display image generator 1015 and outputs the display image. For example, the output 1016 may include a liquid crystal display, an organic EL display, a CRT display, or the like, and may display a display image.

The controller 1017 performs overall control of the ultrasound diagnostic apparatus 100 by controlling each of the operation input 1011, the transmitter 1012, the receiver 1013, the ultrasound image generator 1014, the display image generator 1015, and the output 1016 in accordance with their functions.

The controller 1017 may include a central processing unit (CPU) 1171 as an arithmetic/control device, a read only memory (ROM) 1172 and a random access memory (RAM) 1173 as main storage devices, and the like. The ROM1172 stores basic programs and basic setting information. The CPU1171 reads a program corresponding to processing content from the ROM172, stores the program in the RAM1173, and executes the stored program, thereby centrally controlling the operation of each of the functional blocks (the transmitter 1012, the receiver 1013, the ultrasound image generator 1014, the display image generator 1015, and the output 1016) of the ultrasound diagnostic apparatus main body 1010.

Hardware Configuration of Training Apparatus and Image Processing Apparatus

Figure 10:
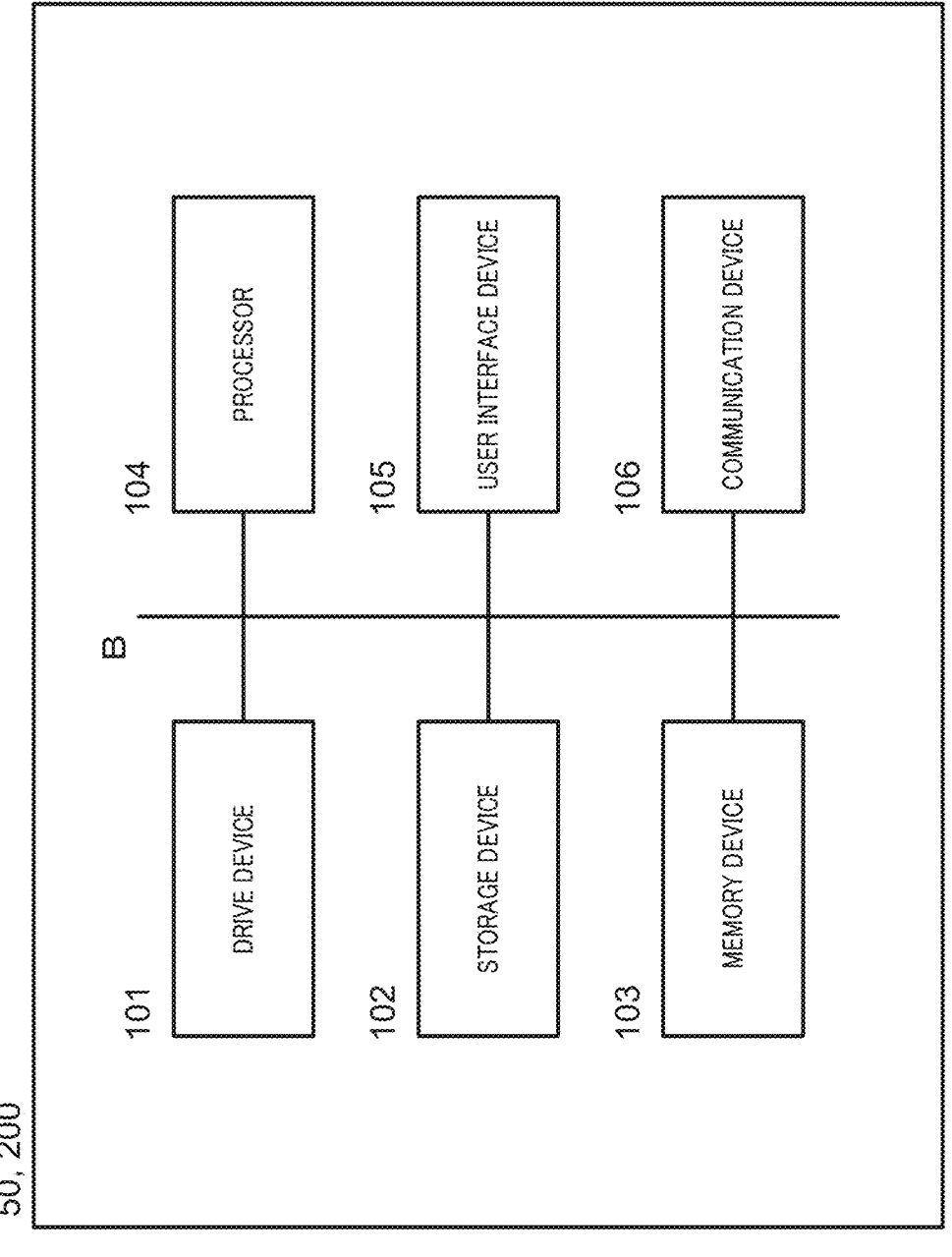
FIG. 10 is a block diagram illustrating a hardware configuration of a training apparatus and an image processing apparatus according to the example of the present disclosure.

Next, a hardware configuration of the training apparatus 50 and the image processing apparatus 200 according to the example of the present disclosure will be described with reference to FIG. 10. FIG. 10 is a block diagram illustrating a hardware configuration of the training apparatus 50 and the image processing apparatus 200 according to the example of the present disclosure.

The training apparatus 50 and the image processing apparatuses 200 may each be implemented by a computing apparatus such as a server, a personal computer, a smartphone, or a tablet, and may have, for example, a hardware configuration as illustrated in FIG. 10. That is, the training apparatus 50 and the image processing apparatus 200 each include a drive device 101, a storage device 102, a memory device 103, a processor 104, a user interface (UI) device 105, and a communication device 106, which are interconnected via a bus B.

The programs or instructions for implementing various functions and processing, which will be described below, in the training apparatus 50 and the image processing apparatus 200 may be stored in removable storage media, such as a compact disk-read only memory (CD-ROM) and a flash memory. When the storage medium is set in the drive device 101, the program or the instruction is installed in the storage device 102 or the memory device 103 from the storage medium via the drive device 101. Note that the program or the instruction does not necessarily have to be installed from the storage media, but may be downloaded from any external device via a network or the like.

The storage device 102 is implemented by a hard disk drive or the like, and stores, together with the installed program or instruction, a file, data, or the like used for execution of the program or instruction.

The memory device 103 is implemented by a random access memory, a static memory, or the like, and when a program or an instruction is activated, reads the program, the instruction, data, or the like from the storage device 102 and stores the read program, instruction, data, or the like. The storage device 102, the memory device 103, and the removable storage medium may be collectively referred to as a non-transitory storage medium.

The processor 104 may be implemented by at least one of central processing unit (CPU), graphics processing unit (GPU), processing circuitry, and the like, which may include one or more processor cores. The processor 104 executes various functions and processing of a below-described model generating apparatus 100 in accordance with programs and instructions stored in the memory device 103, data such as parameters necessary to execute the programs or instructions, and the like.

The user interface (UI) device 105 may include input devices such as a keyboard, a mouse, a camera, and a microphone, output devices such as a display, a speaker, a headset, and a printer, and input/output devices such as a touch panel, and implements an interface between the user and the training apparatus 50 and the image processing apparatus 200. For example, the user operates a graphical user interface (GUI) displayed on a display or a touch panel with a keyboard, a mouse, or the like to operate the training apparatus 50 and the image processing device 200.

The communication device 106 is implemented by various communication circuits that execute wired and/or wireless communication processing with an external apparatus or a communication network such as the Internet, a local area network (LAN), or a cellular network.

However, the above-described hardware configuration is merely an example, and the training apparatus 50 and the image processing apparatuses 200 according to the present disclosure may be implemented by any other appropriate hardware configuration.

Standardization Processing

Next, standardization processing for training and inference processing of a machine learning model used for ultrasonic diagnosis according to an example of the present disclosure will be described. The time-varying image data for training and inference can be acquired from the subject 30 at various sweep speeds and/or acquired from the subject 30 at different heart rates. In a case where the machine learning model is trained by using the time-varying image data of different sweep speeds and/or different heart rates as they are, it is necessary to prepare the required number of pieces of time-varying image data for training the machine learning model 10 for each sweep speed and/or each heart rate, and it takes cost to collect the training data. According to the standardization processing of the present example, the time-varying image data with different sweep speeds and/or different heart rates is standardized to have a predetermined sweep speed and/or a predetermined heart rate, and the machine learning model 10 is trained by using the standardized time-varying image data. Thus, it is not necessary to collect the required number of pieces of time-varying image data for training for each sweep speed and/or each heart rate in order to train the machine learning model 10, and the machine learning model 10 can be generated at a lower cost.

Figure 11:
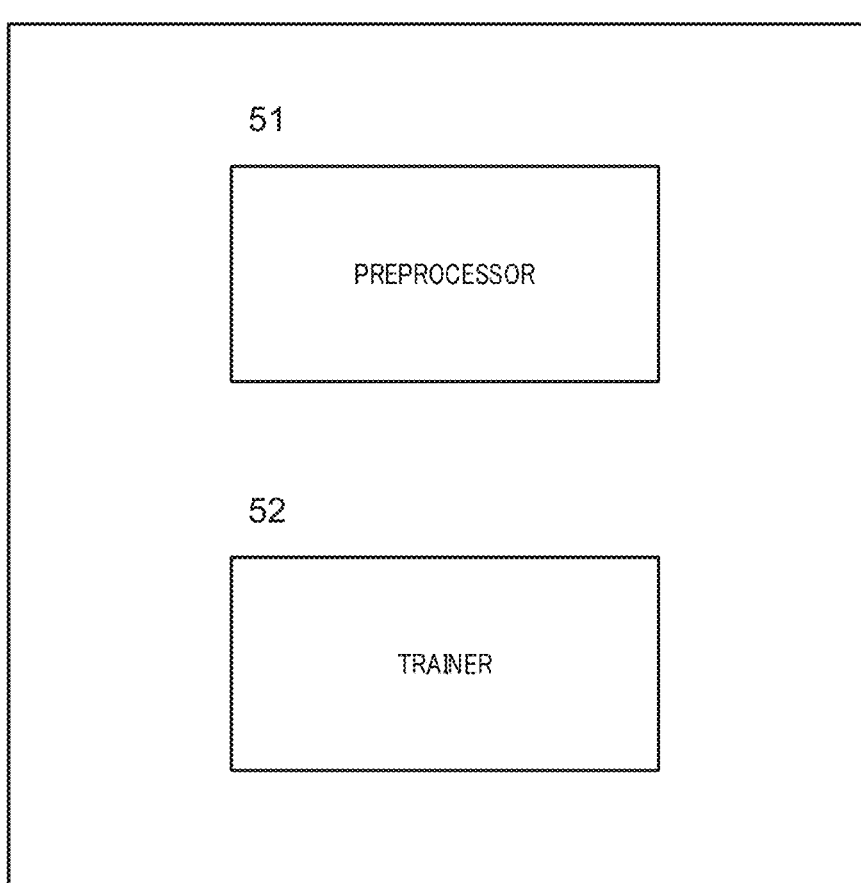
FIG. 11 is a block diagram illustrating a functional configuration of the training apparatus according to the example of the present disclosure.

FIG. 11 is a block diagram illustrating a functional configuration of the training apparatus according to the example of the present disclosure. As illustrated in FIG. 11, a preprocessor 50 according to the present example includes a preprocessor 51 and a trainer 52. For example, one or more functional units of the preprocessor 51 and the trainer 52 may be implemented by one or more processors 104 executing one or more programs or instructions stored in the memory device 103.

Figure 12:
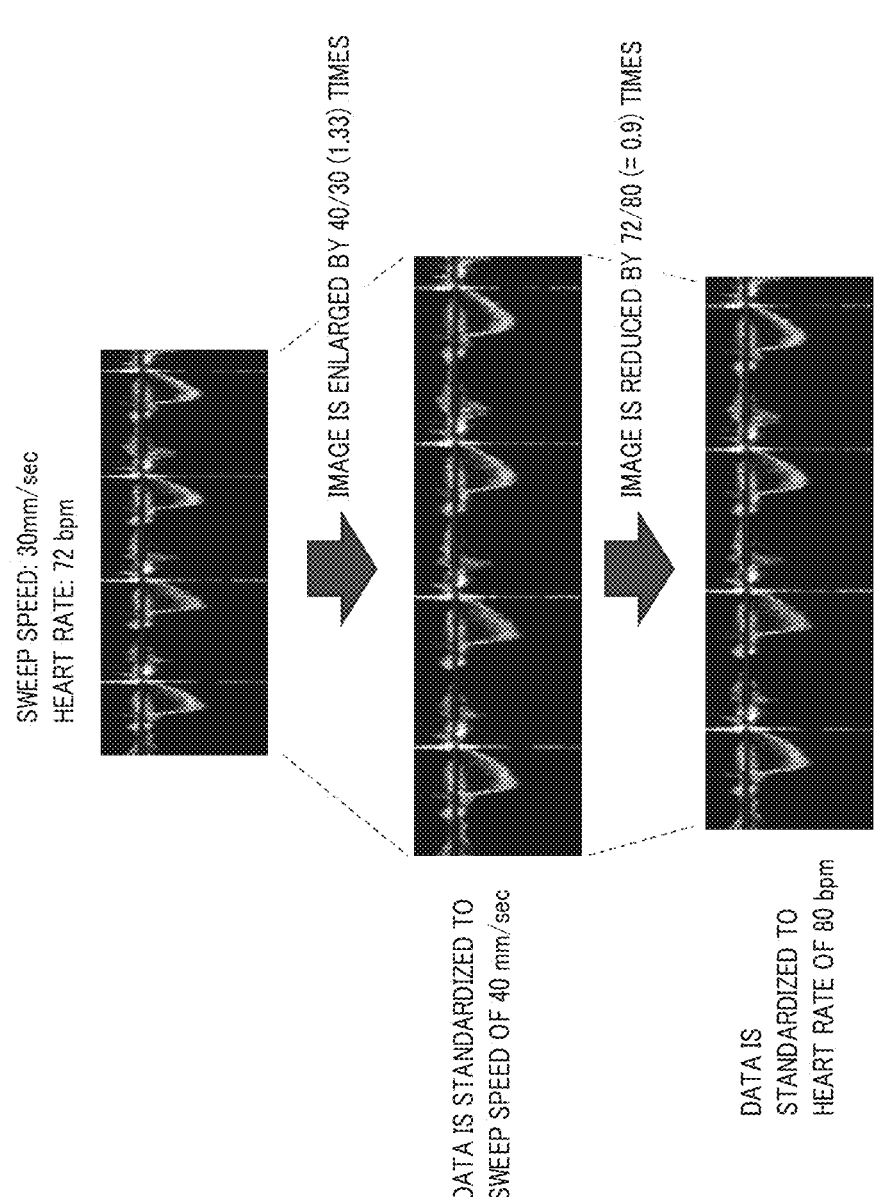
FIG. 12 is a schematic diagram illustrating standardization of time-varying image data according to the example of the present disclosure.

The preprocessor 51 standardizes the time-varying image data. To be specific, the preprocessor 51 may obtain time-varying image data that is obtined in such a way that time-varying image data (that is based on a reception signal for image generation received by the ultrasound probe 1020) is standardized in the time direction, thereby obtaining the time-varying image data. For example, the preprocessor 51 may convert time-varying image data (that is based on a signal received from the subject 30 by the ultrasound probe 1020 at a certain sweep speed) into time-varying image data having a predetermined sweep speed. To be specific, in order to convert time-varying image data for training at a sweep speed of 30 mm/sec into time-varying image data at a predetermined sweep speed of 40 mm/sec, as illustrated in FIG. 12, the preprocessor 51 may enlarge the time-varying image data for training at the sweep speed of 30 mm/sec by 40/30 (=1.33) times in the time direction.

Further, the preprocessor 51 may acquire time-varying image data obtained by further standardizing the enlarged time-varying image data. That is, in order to convert the time-varying image data of a heart rate of 72 bpm standardized with respect to the sweep speed into a predetermined heart rate of 80 bpm, as illustrated in FIG. 12, the preprocessor 51 may reduce the time-varying image data of the heart rate of 72 bpm by 72/80 (=0.9) times in the time direction.

Figure 13:
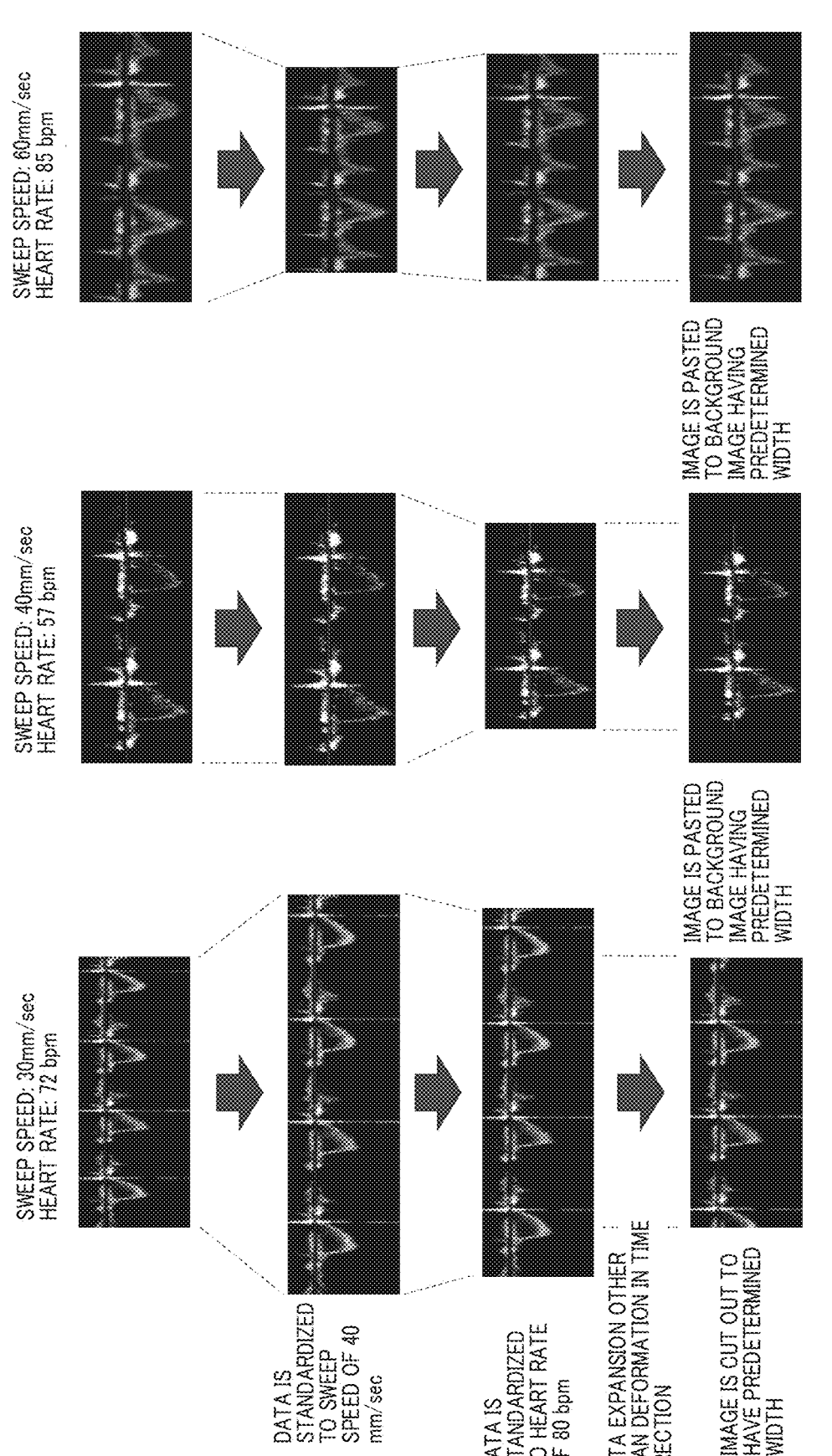
FIG. 13 is a schematic diagram illustrating standardization of time-varying image data according to the example of the present disclosure.

In this manner, the preprocessor 51 standardizes time-varying image data for training at different sweep speeds and/or different heart rates into time-varying image data at a predetermined sweep speed and/or a predetermined heart rate. The preprocessor 51 changes the time-varying image data standardized to have a predetermined sweep speed and/or a predetermined heart rate to time-varying image data having a predetermined width as illustrated in FIG. 13, and acquires time-varying image data for training having a predetermined width in the time direction.

Figure 14:
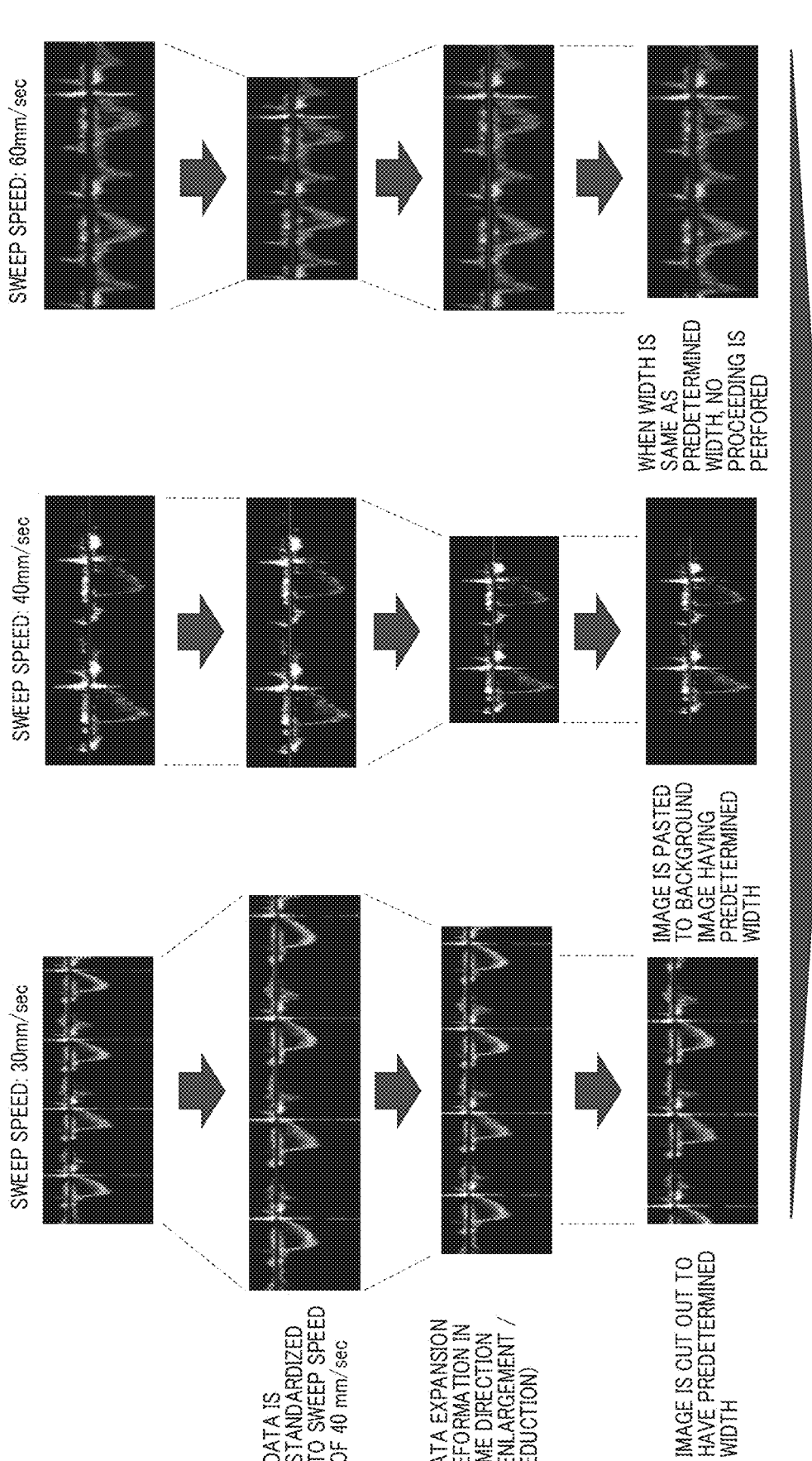
FIG. 14 is a schematic diagram illustrating standardization of time-varying image data according to the example of the present disclosure.

In addition, the preprocessor 51 may perform data expansion for further deforming the time-varying image data, having been standardized in the time direction. That is, in a case where the heart rate of the subject cannot be not obtained, data expansion in which the time-varying image data, having been standardized according to the sweep speed, is enlarged or reduced in the time direction at a random ratio may be performed to cope with the difference in heart rate, as illustrated in FIG. 14.

The trainer 52 trains the machine learning model 10 to be trained by using the time-varying image data preprocessed in this manner. To be more specific, the trainer 52 adjusts the parameters of the machine learning model 10 such as the convolutional neural network by using training data including the time-varying image data for training standardized with respect to the sweep speed and/or the heart rate, and the ground truth data including the detection target corresponding to the time-varying image data for training. Here, the ground truth data may be information related to a feature that is affected by a time change in the time-varying image. To be more specific, the ground truth data (that is, the label data) may be information on a position of at least one point in the time-varying image, information on a width, information on a shape of a waveform, information on timing, information on a time segment, information on a trace, or the like.

For example, when the machine learning model 10 of the training target is a convolutional neural network used for image processing, the trainer 52 may input the standardized time-varying image data for training to the convolutional neural network of the training target and adjust the parameters of the convolutional neural network of the training target in accordance with an error backpropagation method based on the error between the output result from the convolutional neural network of the training target and the ground truth data. The trainer 52 continues the training processing until a predetermined end condition is satisfied, and ends the training processing when the predetermined end condition is satisfied.

Figure 15:
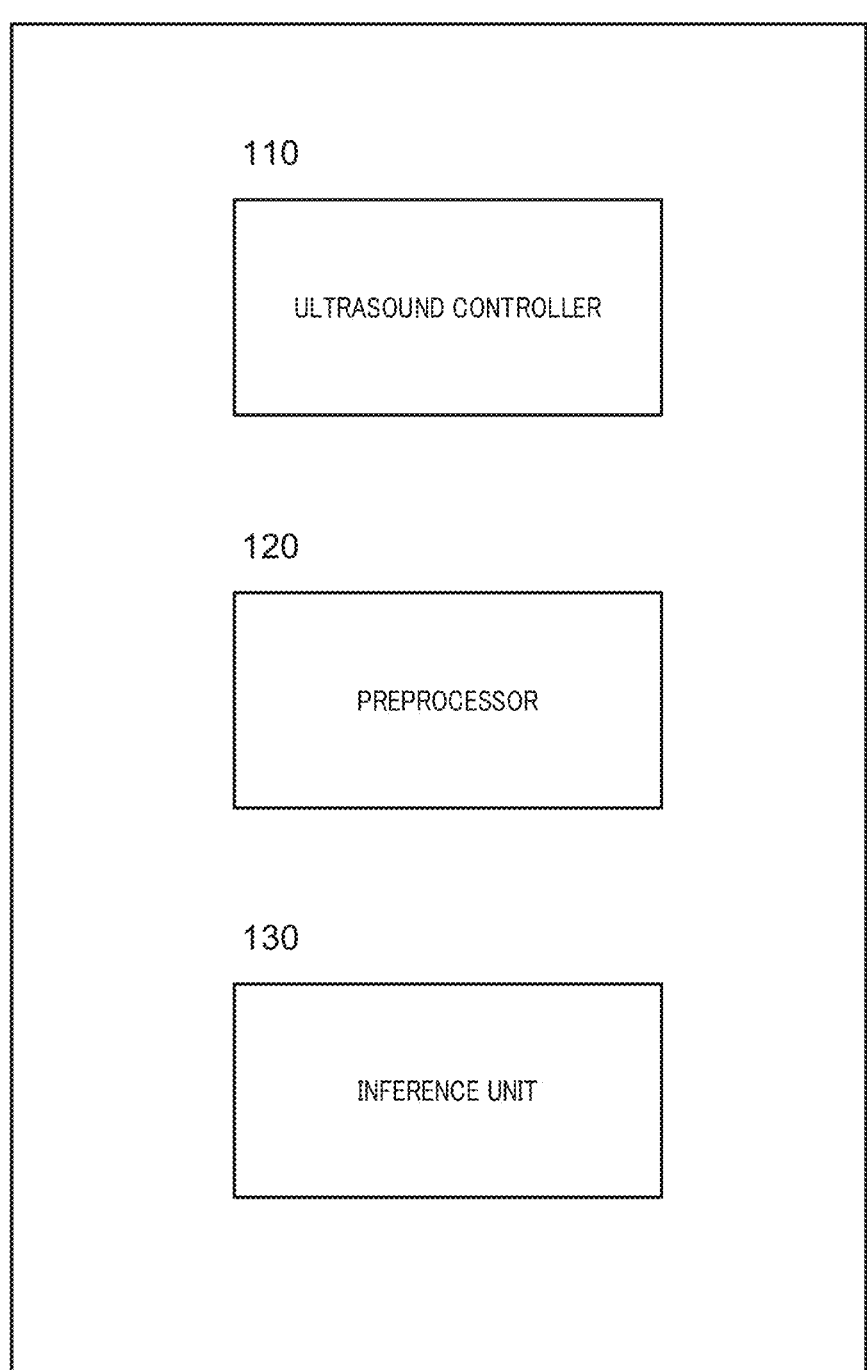
FIG. 15 is a block diagram illustrating a functional configuration of an ultrasound diagnostic apparatus according to the example of the present disclosure.

FIG. 15 is a block diagram illustrating a functional configuration of the ultrasound diagnostic apparatus 100 according to an example of the present disclosure. As illustrated in FIG. 15, the ultrasound diagnostic apparatus 100 according to the present example includes an ultrasound controller 110, a preprocessor 120, and an inference section 130. For example, one or more functional units of the ultrasound controller 110, the preprocessor 120, and the inference section 130 may be implemented by one or more CPU 1171 executing one or more programs or instructions stored in a ROM 1172 or RAM 1173.

The ultrasound controller 110 controls ultrasound signals transmitted and received by the ultrasound diagnostic apparatus 100. To be more specific, the ultrasound controller 110 controls an ultrasound signal to be sent out from the ultrasound probe 1020 to the subject 30, and receives a reflected ultrasound signal from the subject 30. For example, the ultrasound controller 110 may send an ultrasound signal from the ultrasound probe 1020 and receive a reflected ultrasound signal from an object. The ultrasound controller 110 generates time-varying image data in the detection target region of the subject 30 according to the sweep speed set by the user based on the received ultrasound signal.

The preprocessor 120 preprocesses the time-varying image data. To be more specific, when the trained machine learning model 10 is trained with time-varying image data standardized by a predetermined sweep speed and/or a predetermined heart rate, the preprocessor 120 standardizes, by the predetermined sweep speed and/or the predetermined heart rate, the time-varying image data acquired from the subject 30 by the ultrasound controller 110. For example, as illustrated in FIG. 12, when the time-varying image data acquired by the ultrasound controller 110 has a sweep speed of 30 mm/sec and a heart rate of 72 bpm, the preprocessor 120 first enlarges the acquired time-varying image by a factor of 40/30 (=1.33) in order to standardize the image to have the predetermined sweep speed of 40 mm/sec, and further reduces the image by a factor of 72/80 (=0.9) in order to standardize the image to hav the predetermined heart rate 80 bpm. The preprocessor 120 passes the time-varying image data standardized in this manner to the inference section 130.

The inference section 130 acquires, using the trained machine learning model 10, an inference result for the time-varying image data standardized by the preprocessor 120. To be more specific, the inference section 130 inputs the standardized time-varying image data into the trained machine learning model 10, and acquires an inference result regarding the detection target region from the trained machine learning model 10. The inference section 130 performs, on the inference result, processing opposite to the enlargement and/or reduction performed by the preprocessor 120 and acquires an inference result corresponding to the time-varying image data acquired by the ultrasound controller 110.

Example of VTI Measurement

Figure 17:
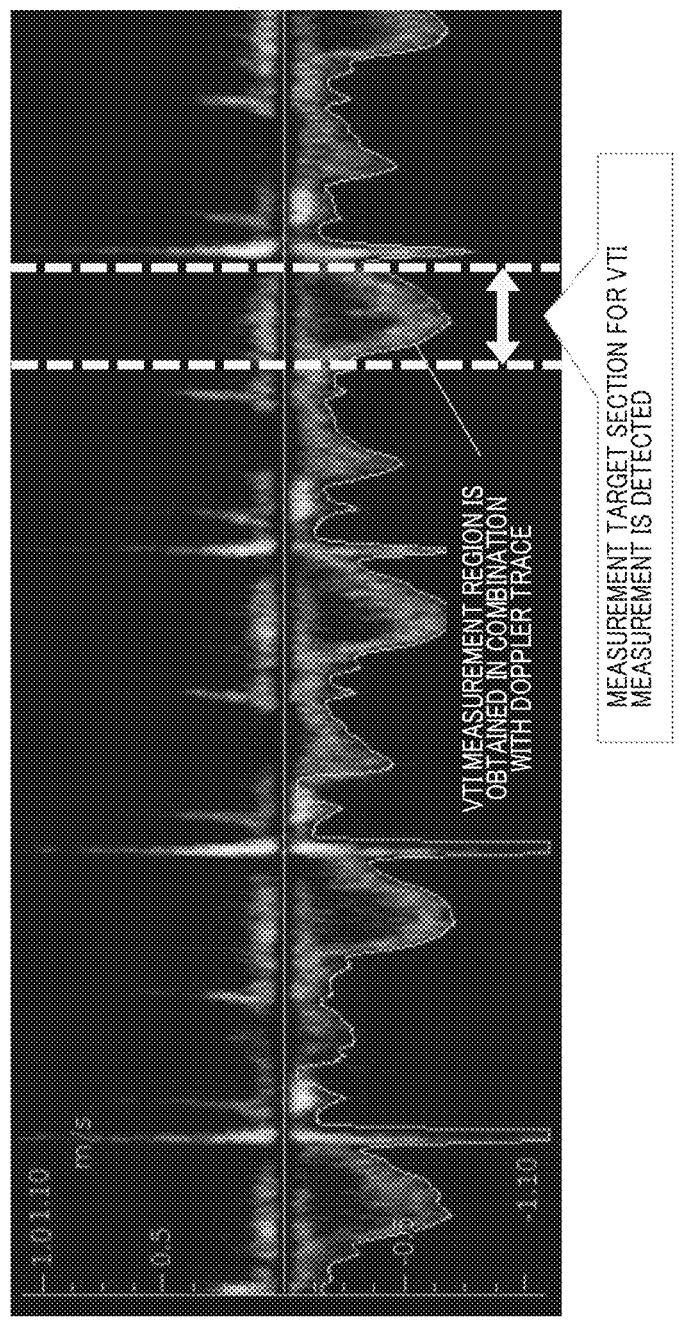
FIG. 17 is a diagram illustrating VTI measurement processing according to the example of the present disclosure.

The machine learning model 10 according to the present example can be used for velocity-time integral (VTI) measurement. Here, the VTI is a velocity-time integral value, and VTI in the left ventricular outflow tract (LVOT) of the heart is used as an evaluation index of cardiac left ventricular systolic function. The area of the PW Doppler speed waveform is equal to the time integral value VTI of the blood flow velocity. Here, for example, as illustrated in FIG. 16, the LVOT diameter can be measured in a parasternal left marginal long-axis image. In FIG. 16, the area of an enclosed region on the time-varying image data corresponds to the VTI. For the VTI measurement, the machine learning model 10 is trained to detect a VTI measurement target section and/or a VTI measurement target region as illustrated in FIG. 17 from the input time-varying image data.

Figure 18:
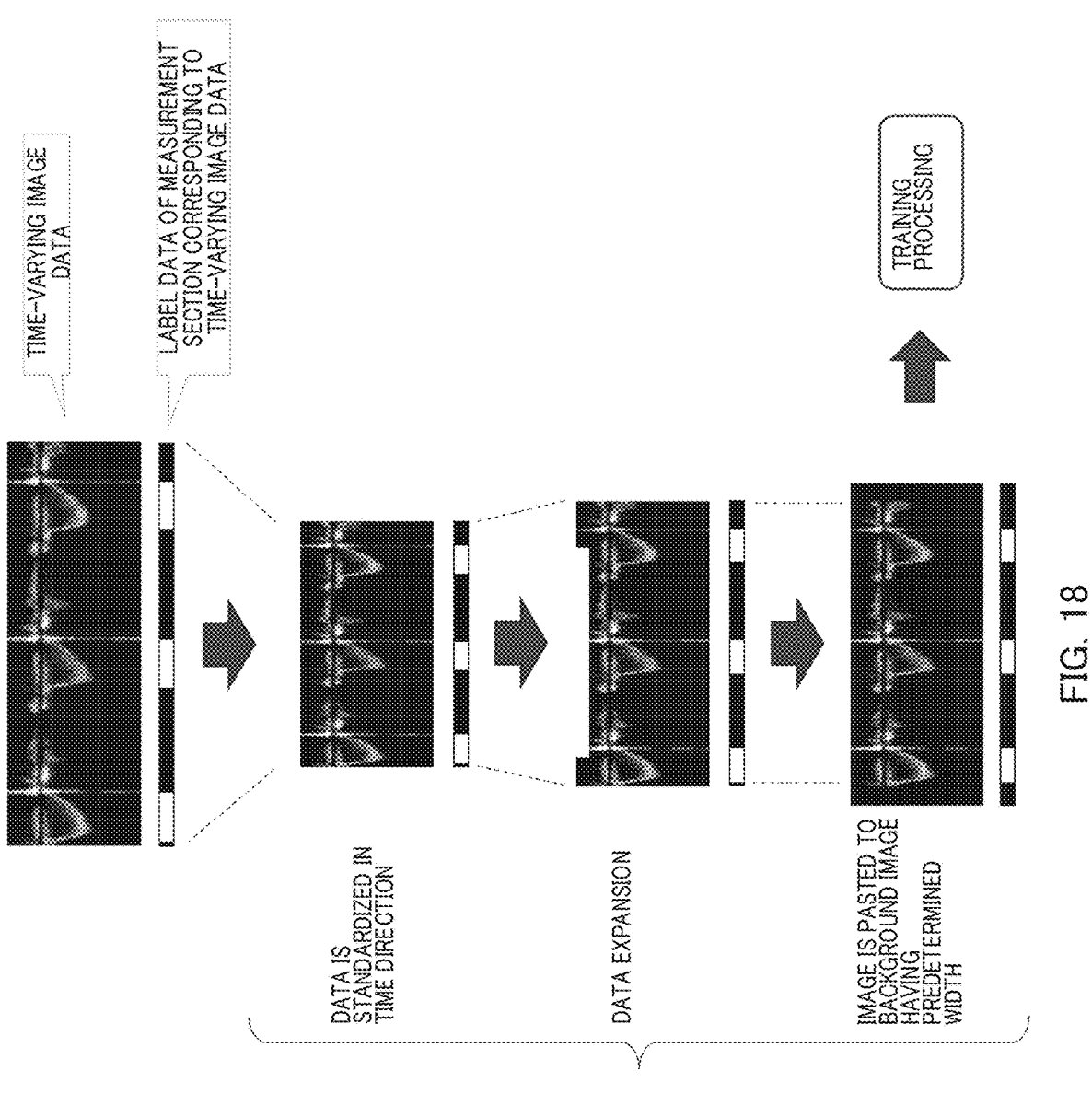
FIG. 18 is a diagram illustrating training processing for VTI measurement according to the example of the present disclosure.

In the training processing of the machine learning model 10, for example, time-varying image data and label data of a measurement section corresponding to the time-varying image data are prepared as training data, as illustrated in FIG. 18. Since the time-varying image data for training is acquired at different sweep speeds and/or different heart rates, the time-varying image data and the label data are standardized to have a predetermined sweep speed and/or a predetermined heart rate as described above, and are enlarged and/or reduced in the time direction, as illustrated. For example, the time-varying image data and the label data illustrated in FIG. 18 are first reduced in the time direction in order to be standardized to have a predetermined sweep speed and then enlarged in the time direction in order to be standardized to have a predetermined heart rate. The time-varying image data and the label data having been enlarged and reduced in this manner are superimposed on the background image so as to have a predetermined width in the time direction. Then, time-varying image data having the predetermined width and label data are input to the training process.

Figure 19:
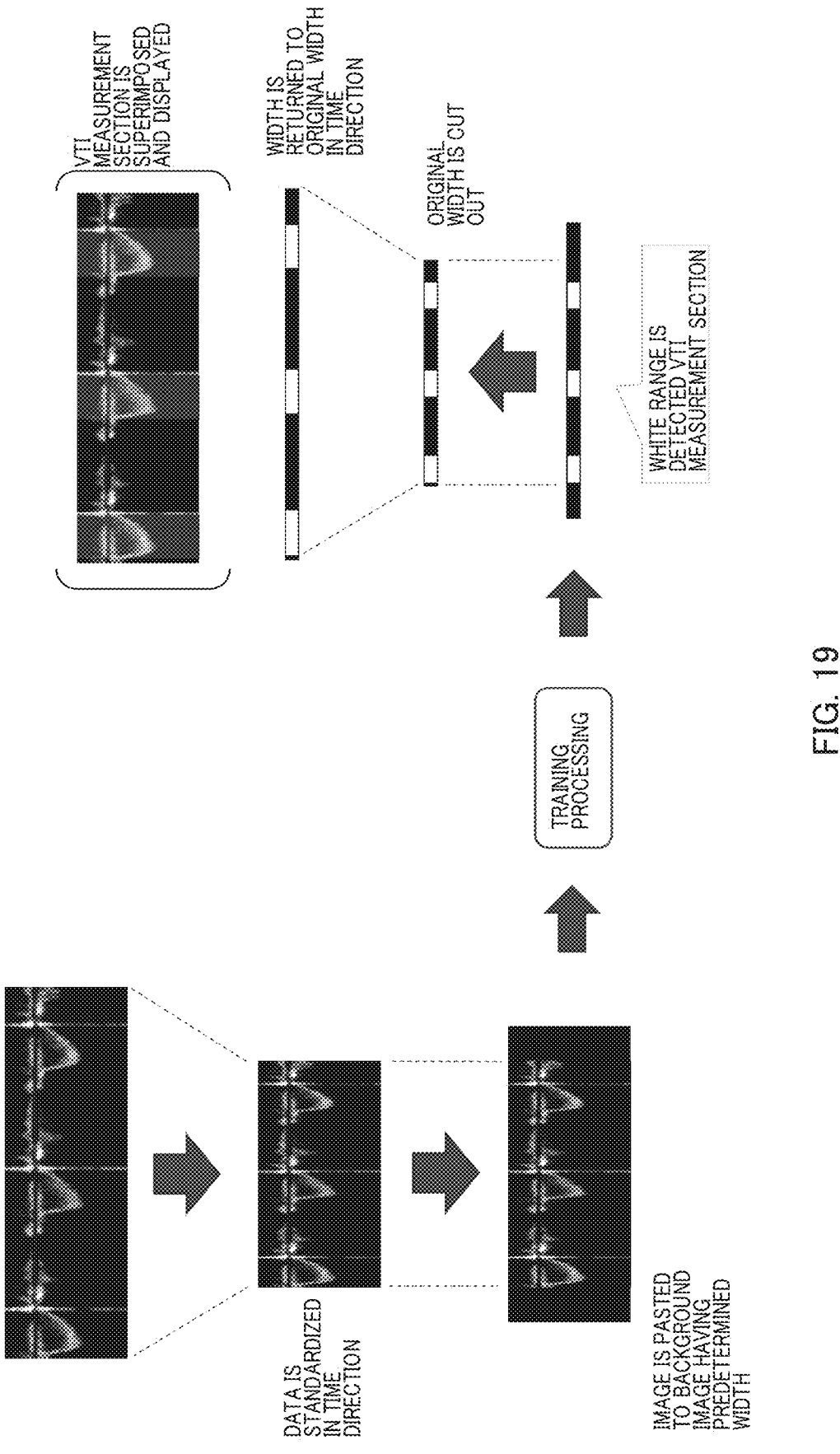
FIG. 19 is a diagram illustrating inference processing for VTI measurement according to the example of the present disclosure.

Next, in the inference processing using the trained machine learning model 10, when time-varying image data of an inference target as illustrated in FIG. 19 is provided, the time-varying image data of the inference target is standardized in the time direction and superimposed on the background image so as to have a predetermined width in the time direction. The standardized time-varying image data having a predetermined time width in this manner is input to the trained machine learning model 10, and as illustrated in FIG. 19, a VTI measurement section in the standardized time-varying image data is predicted. The processing opposite to the preprocessing is then performed on the predicted VTI measurement section. That is, the portion of the background image superimposed in the preprocessing is excluded from the VTI measurement section, and thereafter, the width is returned to the original width in the time direction. The VTI measurement section acquired in this manner may be superimposed and displayed on the time-varying image data of the inference target.

Figure 20:
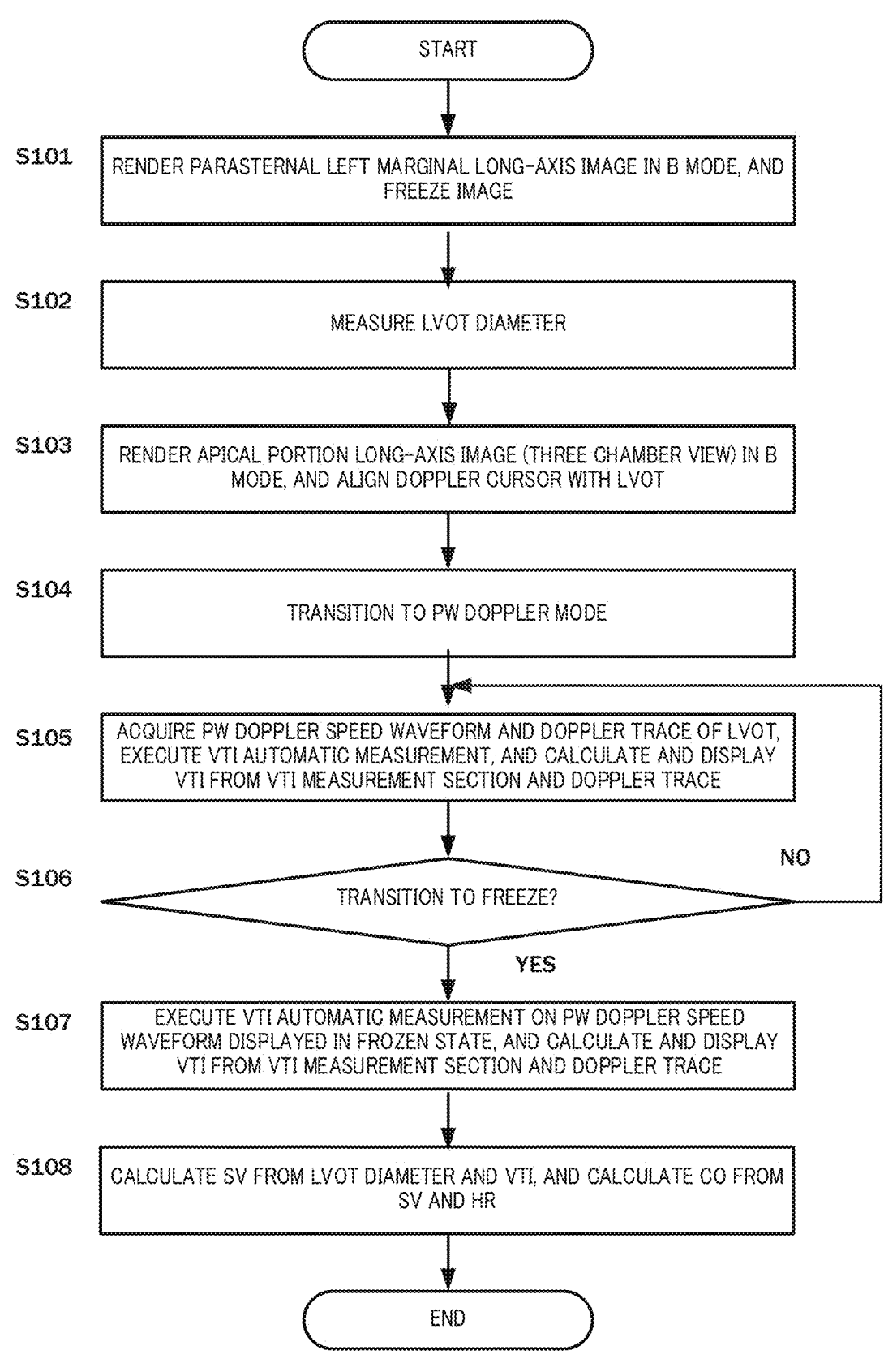
FIG. 20 is a flowchart illustrating VTI measurement processing according to the example of the present disclosure.

FIG. 20 is a flowchart illustrating ultrasound diagnostic processing according to an example of the present disclosure. As illustrated in FIG. 20, in step S101, the ultrasound diagnostic apparatus 100 renders a parasternal left marginal long-axis image in the B mode, and freezes the rendered image.

In step S102, the ultrasound diagnostic apparatus 100 measures the LVOT diameter. For example, the ultrasound diagnostic apparatus 100 may measure the length of a portion indicating the LVOT diameter designated by the user on the frozen parasternal left marginal long-axis image.

In step S103, the ultrasound diagnostic apparatus 100 renders an apical portion long-axis image (three chamber view) in the B mode, and aligns the Doppler cursor with the LVOT. For example, the ultrasound diagnostic apparatus 100 receives an instruction for LVOT from the user on the rendered apical portion long-axis image.

In step S104, the ultrasound diagnostic apparatus 100 transitions to a pulsed wave (PW) Doppler mode.

In step S105, the ultrasound diagnostic apparatus 100 acquires a PW Doppler speed waveform and a Doppler trace of the LVOT, executes VTI automatic measurement on the PW Doppler speed waveform as time-varying image data, and calculates and displays a VTI from a VTI measurement section and the Doppler trace. That is, the ultrasound diagnostic apparatus 100 inputs a PW Doppler speed waveform as time-varying image data of a measurement target to the trained machine learning model 10, and acquires a VTI measurement section from the trained machine learning model 10. Then, the ultrasound diagnostic apparatus 100 calculates the VTI from the acquired VTI measurement section and the Doppler trace.

In step S106, the ultrasound diagnostic apparatus 100 determines whether the state has transitioned to the freeze state. When the state has not transitioned to the freeze state (S106: NO), the ultrasound diagnostic apparatus 100 proceeds to step S105 and repeats the above-described processing. On the other hand, when the state has transitioned to the freeze state (S106: YES), the ultrasound diagnostic apparatus 100 proceeds to step S107.

In step S107, the ultrasound diagnostic apparatus 100 executes VTI automatic measurement for the PW Doppler speed waveform displayed in a frozen state, and calculates and displays a VTI from the VTI measurement section and the Doppler trace. That is, the ultrasound diagnostic apparatus 100 inputs a PW Doppler speed waveform as time-varying image data of a measurement target to the trained machine learning model 10, and acquires a VTI measurement section from the trained machine learning model 10. Then, the ultrasound diagnostic apparatus 100 calculates the VTI from the acquired VTI measurement section and the Doppler trace.

In step S108, the ultrasound diagnostic apparatus 100 calculates the stroke volume (SV) from the LVOT diameter and VTI, and calculates cardiac output (CO) from the SV and the heart rate (HR).

As described above, according to the present example, the VTI automatic measurement is executed by using the machine learning model 10 trained by the training data including the standardized time-varying image data and the VTI measurement target section, and the VTI can be estimated from the time-varying image data acquired from the subject 30, based on the estimated VTI measurement target section and the Doppler trace.

Figure 21:
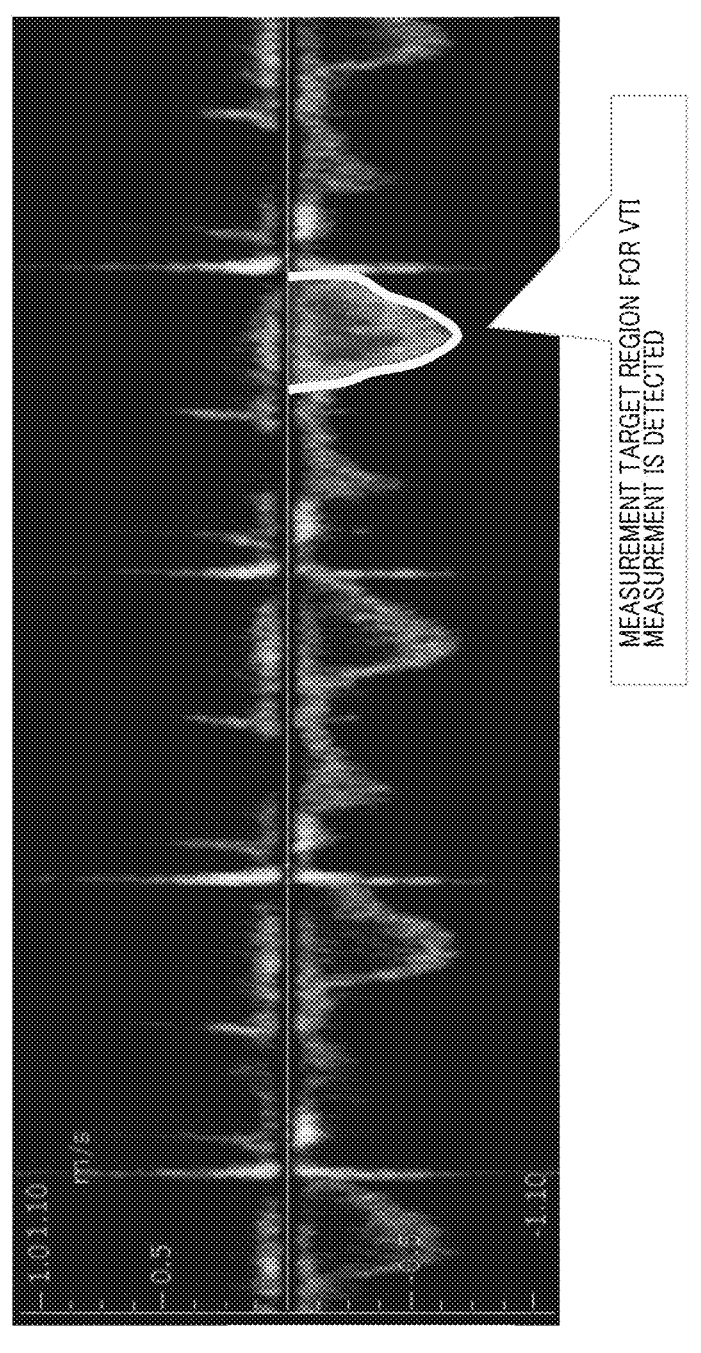
FIG. 21 is a diagram illustrating VTI measurement processing according to the example of the present disclosure.

In the above-described example, the VTI is estimated from the VTI measurement target section estimated by the VTI automatic measurement and the Doppler trace, but the machine learning model 10 according to the present example may be trained to detect the VTI measurement target region as illustrated in FIG. 21.

Figure 22:
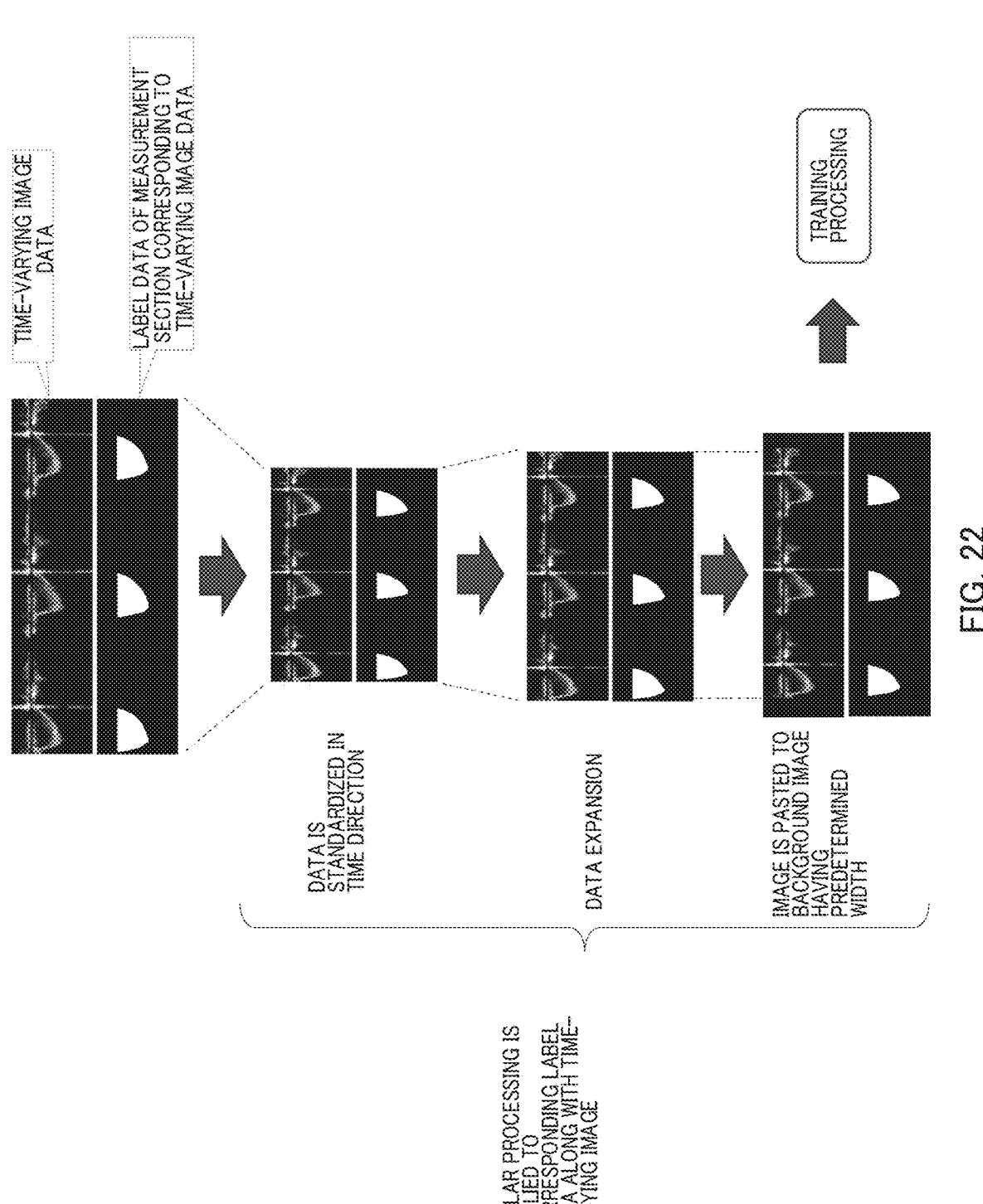
FIG. 22 is a diagram illustrating training processing for VTI measurement according to the example of the present disclosure.

In the training processing of the machine learning model 10, for example, time-varying image data and label data of measurement regions corresponding to the time-varying image data are prepared as training data, as illustrated in FIG. 22. Since the time-varying image data for training is acquired at different sweep speeds and/or different heart rates, the time-varying image data and the label data are standardized to have a predetermined sweep speed and/or a predetermined heart rate as described above, and are enlarged and/or reduced in the time direction, as illustrated. For example, the time-varying image data and the label data illustrated in FIG. 22 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 23:
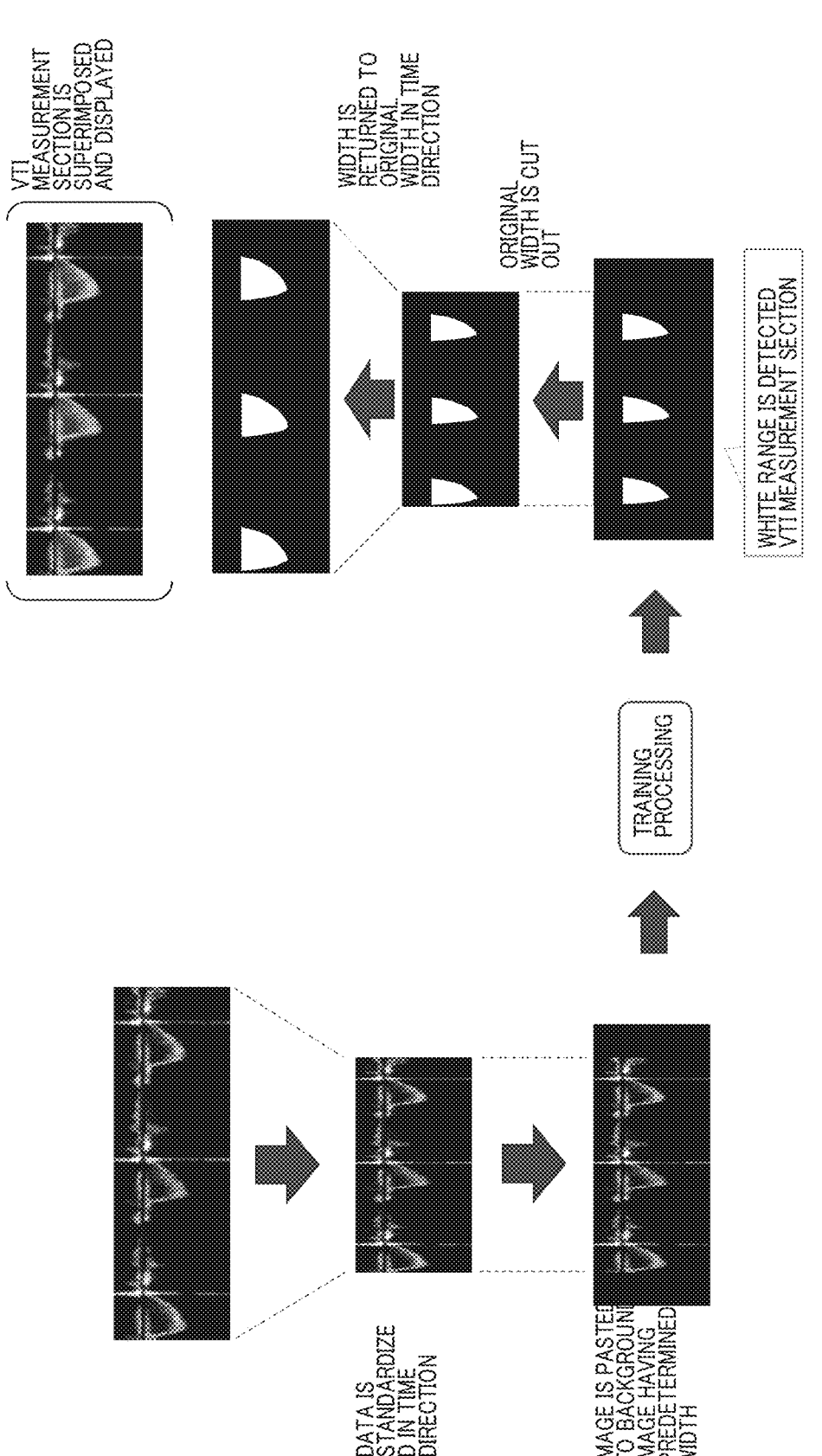
FIG. 23 is a diagram illustrating inference processing for VTI measurement according to the example of the present disclosure.

Next, when time-varying image data of an inference target as illustrated in FIG. 23 is provided in the inference processing using the trained machine learning model 10, the time-varying image data of the inference target is standardized in the time direction and superimposed on the background image so as to have a predetermined width in the time direction. The standardized time-varying image data having such a predetermined time width is input to the trained machine learning model 10, and as illustrated in FIG. 23, a VTI measurement target region in the standardized time-varying image data is predicted. Thereafter, processing opposite to the preprocessing is executed on the predicted VTI measurement target region. That is, the portion of the background image superimposed in the preprocessing is excluded from the VTI measurement target region, and thereafter, the width is returned to the original width in the time direction. The VTI measurement region acquired in this manner may be superimposed on the time-varying image data of the inference target and displayed.

Figure 24:
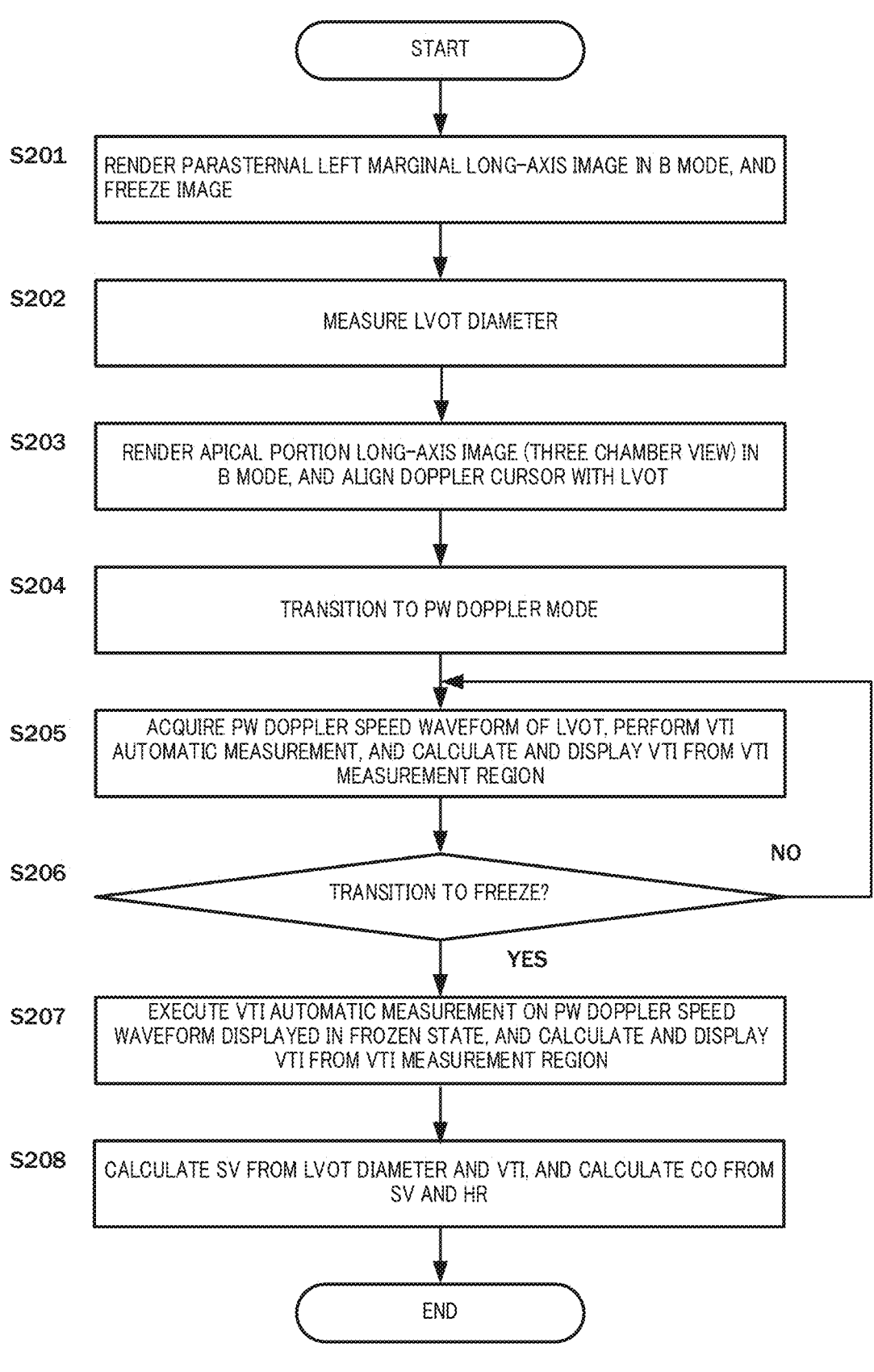
FIG. 24 is a flowchart illustrating VTI measurement processing according to an example of the present disclosure.

FIG. 24 is a flowchart illustrating ultrasound diagnostic processing according to an example of the present disclosure. As illustrated in FIG. 24, in step S201, the ultrasound diagnostic apparatus 100 renders a parasternal left marginal long-axis image in the B mode, and freezes the rendered image.

In step S202, the ultrasound diagnostic apparatus 100 measures the LVOT diameter. For example, the ultrasound diagnostic apparatus 100 may measure the length of a portion indicating the LVOT diameter designated by the user on the frozen parasternal left marginal long-axis image.

In step S203, the ultrasound diagnostic apparatus 100 renders an apical portion long-axis image (three chamber view) in the B mode, and aligns the Doppler cursor with the LVOT. For example, the ultrasound diagnostic apparatus 100 receives an instruction for LVOT from the user on the rendered apical portion long-axis image.

In step S204, the ultrasound diagnostic apparatus 100 transitions to the PW Doppler mode.

In step S205, the ultrasound diagnostic apparatus 100 acquires a PW Doppler speed waveform of the LVOT, performs VTI automatic measurement on the PW Doppler speed waveform, and calculates and displays a VTI from the estimated VTI measurement target region. That is, the ultrasound diagnostic apparatus 100 inputs a PW Doppler speed waveform as time-varying image data of a measurement target region to the trained machine learning model 10, and acquires a VTI measurement target region from the trained machine learning model 10. Then, the ultrasound diagnostic apparatus 100 calculates the VTI from the acquired VTI measurement target region.

In step S206, the ultrasound diagnostic apparatus 100 determines whether the state has transitioned to the freeze state. When the state has not transitioned to the freeze state (S206: NO), the ultrasound diagnostic apparatus 100 proceeds to step S205 and repeats the above-described processing. On the other hand, when the state has transitioned to the freeze state (S206: YES), the ultrasound diagnostic apparatus 100 proceeds to step S207.

In step S207, the ultrasound diagnostic apparatus 100 executes VTI automatic measurement on the PW Doppler speed waveform displayed in a frozen state, and calculates and displays a VTI from the estimated VTI measurement target region. That is, the ultrasound diagnostic apparatus 100 inputs a PW Doppler speed waveform as time-varying image data of a measurement target region to the trained machine learning model 10, and acquires a VTI measurement target region from the trained machine learning model 10. Then, the ultrasound diagnostic apparatus 100 calculates the VTI from the acquired VTI measurement target region.

In step S208, the ultrasound diagnostic apparatus 100 calculates the stroke volume (SV) from the LVOT diameter and the VTI, and calculates the cardiac output (CO) from the SV and the heart rate (HR).

As described above, according to the present example, the VTI automatic measurement is executed by using the machine learning model 10 trained by the training data including the standardized time-varying image data and the VTI measurement target region, and the VTI can be estimated from the time-varying image data acquired from the subject 30, based on the estimated VTI measurement target region.

Example of PSV and EDV

Figure 25:
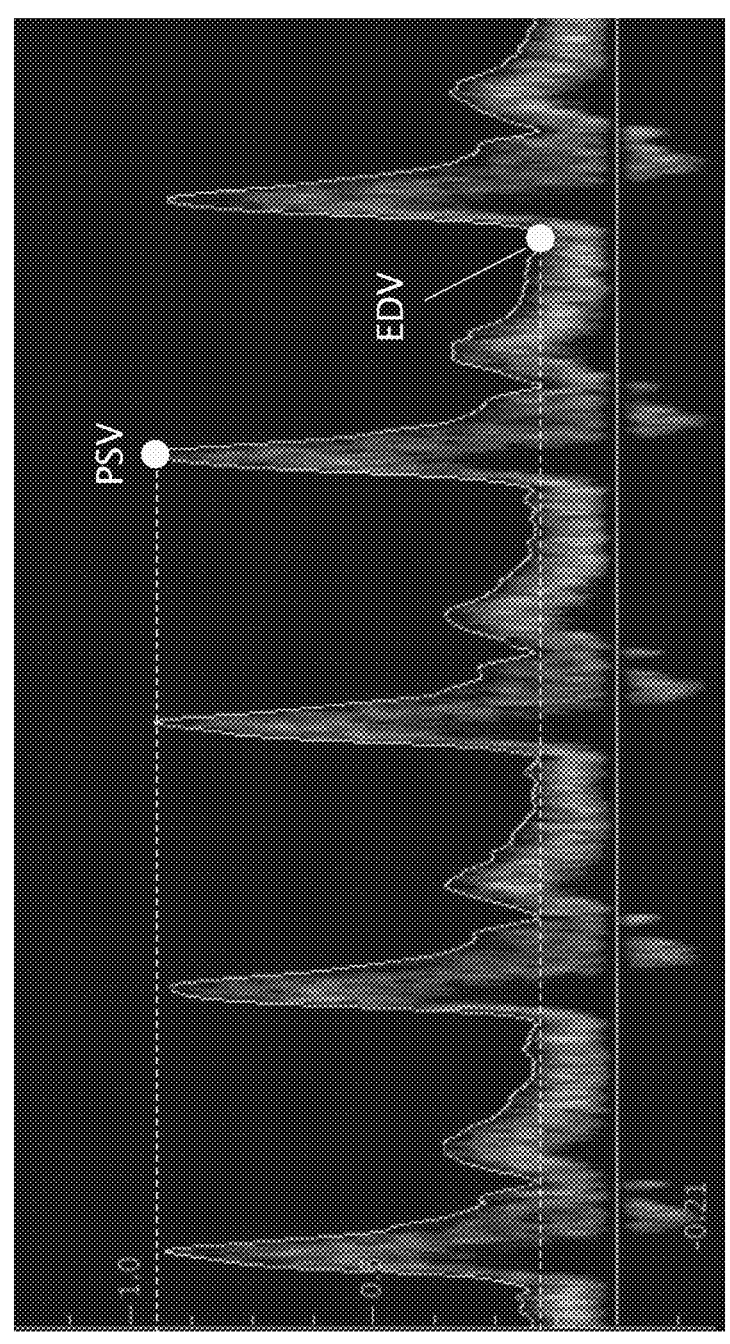
FIG. 25 is a diagram illustrating PSV and EDV measurement processing according to the example of the present disclosure.

As illustrated in FIG. 25, the machine learning model 10 according to the present example can be used to measure peak systolic velocity (PSV) and/or end diastolic velocity (EDV). Here, PSV is the maximum blood flow velocity during one heart beat, and EDV is the blood flow velocity at the end diastole (immediately before the heart contracts). PSV and EDV can be used to calculate indices of resistance index (RI) and pulsatility index (PI). That is, the following is satisfied: RI=(PSV−EDV)/PSV, and PI=(PSV−EDV)/TAMV. Here, the time-averaged maximum blood flow velocity (time averaged maximum velocity:TAMV) is a time average of one heartbeat of the maximum flow velocity. For PSV and EDV measurement, the machine learning model 10 is trained to detect the positions and/or timing of the PSV and EDV from the input time-varying image data.

Figure 26:
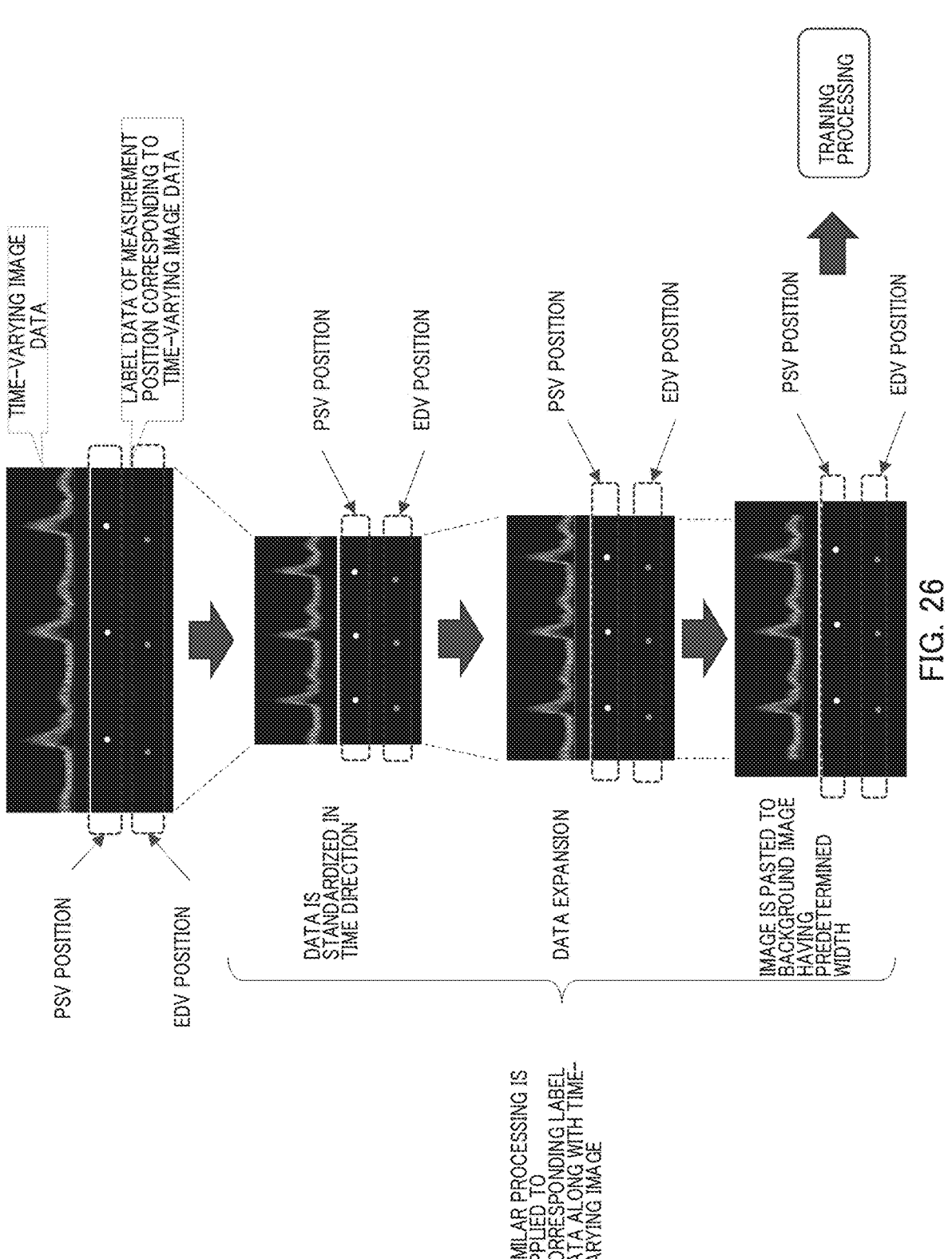
FIG. 26 is a diagram illustrating training processing for PSV and EDV measurement according to the example of the present disclosure.

In the training processing of the machine learning model 10, for example, time-varying image data as illustrated in FIG. 26 and label data on PSV positions and EDV positions corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate as described above, and are enlarged and/or reduced in the time direction, as illustrated. For example, the time-varying image data and the label data illustrated in FIG. 26 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 27:
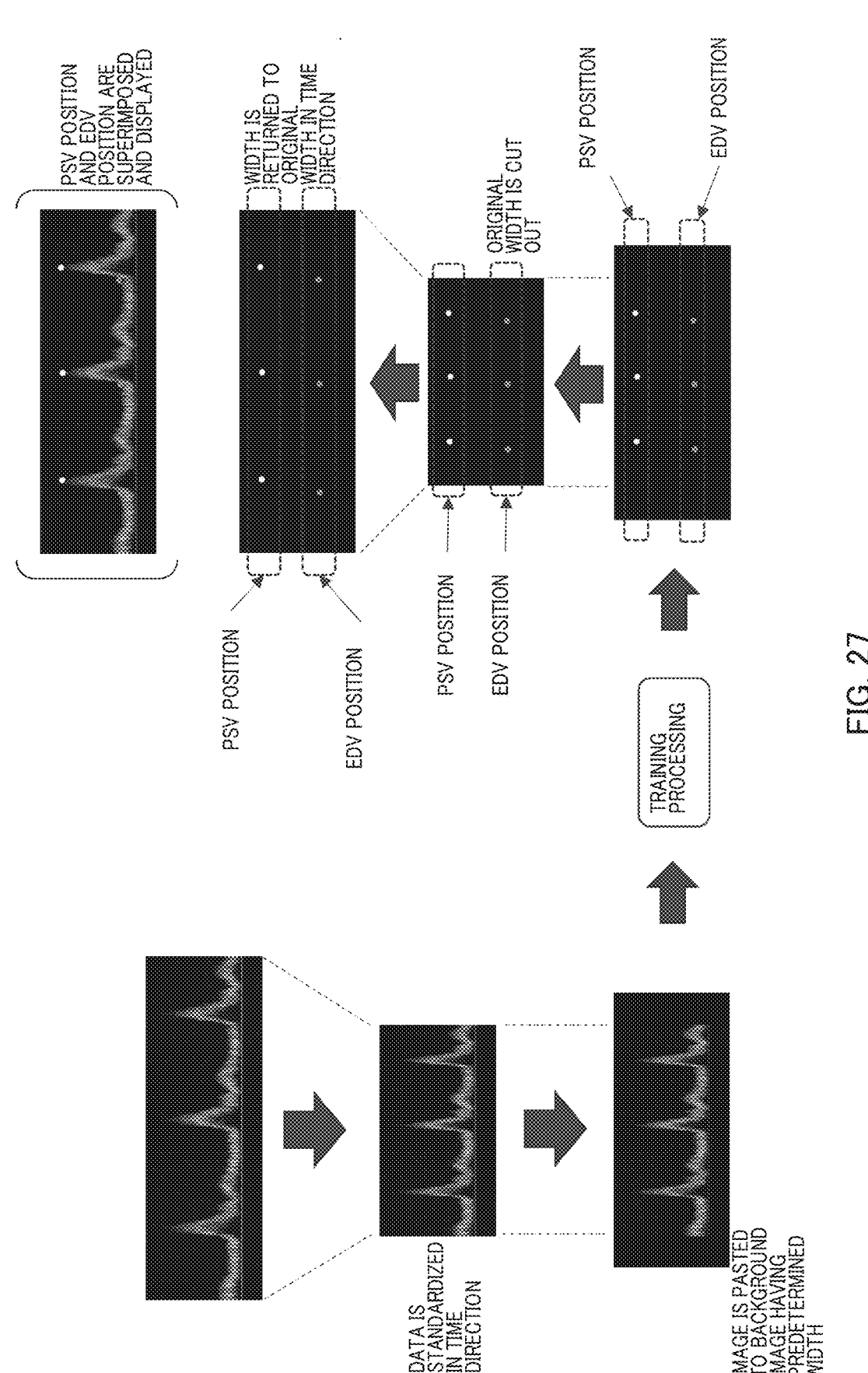
FIG. 27 is a diagram illustrating inference processing for PSV and EDV measurement according to the example of the present disclosure.

Next, in the inference processing using the trained machine learning model 10, when time-varying image data of an inference target as illustrated in FIG. 27 is provided, the time-varying image data of the inference target is standardized in the time direction and superimposed on the background image so as to have a predetermined width in the time direction. The standardized time-varying image data having a predetermined time width in this manner is input to the trained machine learning model 10, and as illustrated in FIG. 27, the PSV position and the EDV position in the standardized time-varying image data are predicted. The processing opposite to the preprocessing is then performed on the predicted PSV and EDV positions. That is, the portion of the background image superimposed in the preprocessing is excluded from the PSV position and the EDV position, and thereafter, the width is returned to the original width in the time direction. The PSV position and the EDV position acquired in this manner may be superimposed and displayed on the time-varying image data of the inference target.

FIG. 28 is a flowchart illustrating ultrasound diagnostic processing according to an example of the present disclosure. As illustrated in FIG. 28, in step S301, the ultrasound diagnostic apparatus 100 renders a blood vessel of the measurement target in the B mode, and aligns the Doppler cursor with the blood vessel. For example, the ultrasound diagnostic apparatus 100 receives an instruction for a blood vessel portion of the measurement target and a Doppler cursor from the user on the rendered blood vessel.

In step S302, the ultrasound diagnostic apparatus 100 transitions to the PW Doppler mode.

In step S303, the ultrasound diagnostic apparatus 100 acquires a PW speed waveform and a Doppler trace in the blood vessel, executes PSV and EDV automatic measurement on the PW Doppler speed waveform as time-varying image data, and calculates and displays the flow velocity of the PSV and the EDV.

In step S304, the ultrasound diagnostic apparatus 100 calculates and displays a resistance index RI from the PSV and the EDV, calculates a time-averaged maximum blood flow velocity (TAMV) from the Doppler trace, and calculates and displays a pulsatility index (PI) from the PSV and the TAMV.

In step S305, the ultrasound diagnostic apparatus 100 determines whether the state has transitioned to the freeze state. When the state has not transitioned to the freeze state (S305: NO), the ultrasound diagnostic apparatus 100 proceeds to step S303 and repeats the above-described processing. On the other hand, when the state has transitioned to the freeze state (S305: YES), the ultrasound diagnostic apparatus 100 proceeds to step S306.

In step S306, the ultrasound diagnostic apparatus 100 executes PSV and EDV automatic measurement on the PW Doppler speed waveform displayed in a frozen state, and calculates the flow velocity of the PSV and the EDV from the PSV position and the EDV position and displays the flow velocity. That is, the ultrasound diagnostic apparatus 100 inputs the PW Doppler speed waveform as time-varying image data of a measurement target to the trained machine learning model 10 and acquires the PSV position and the EDV position from the trained machine learning model 10. Then, the ultrasound diagnostic apparatus 100 calculates and displays the flow velocity of the PSV and the EDV from the acquired PSV position and EDV position.

In step S307, the ultrasound diagnostic apparatus 100 calculates and displays a resistance index (RI) from the PSV and the EDV, calculates a time-averaged maximum blood velocity (TAMV) from the Doppler trace, and calculates and displays a pulsatility index (PI) from the PSV and the TAMV.

As described above, according to the present example, the PSV and EDV automatic measurement is executed by using the machine learning model 10 trained by the training data including the standardized time-varying image data and the PSV position and the EDV position, and the RI and the PI can be estimated from the time-varying image data acquired from the subject 30, based on the estimated PSV position and EDV position, the Doppler trace, and the TAMV calculated from the Doppler trace.

Figure 29:
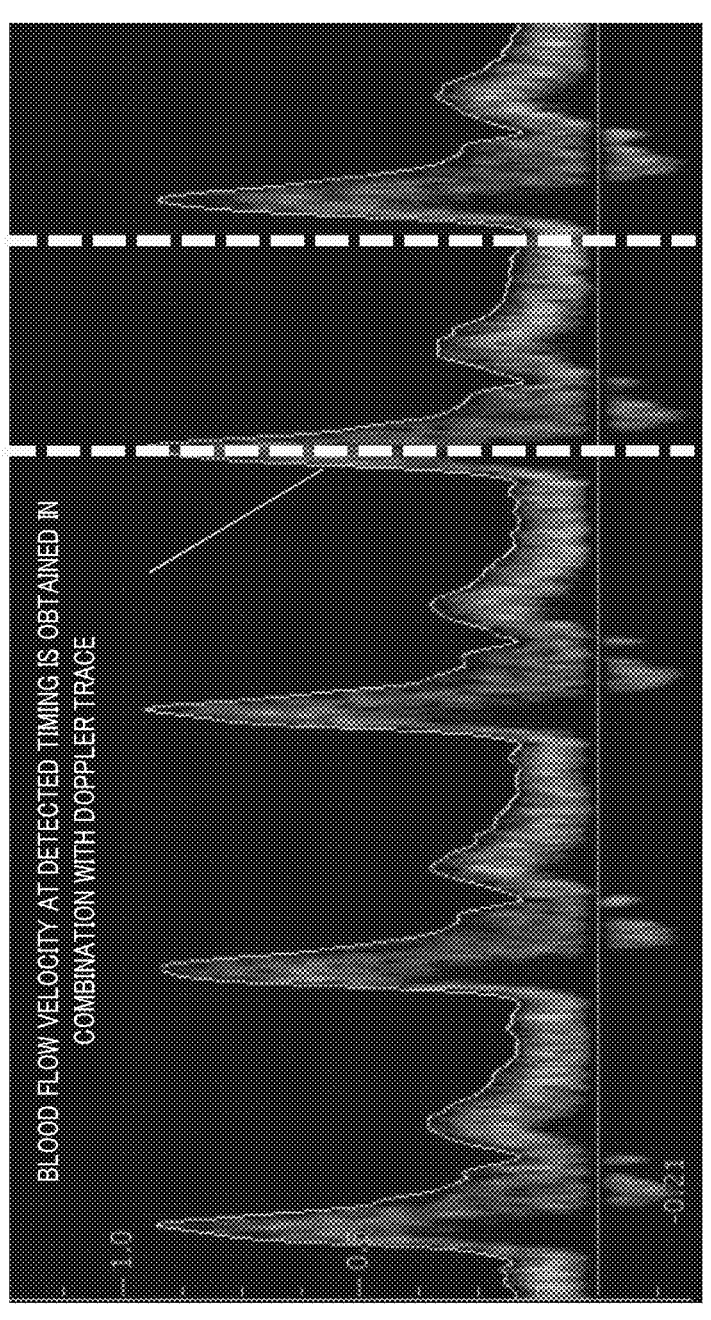
FIG. 29 is a diagram illustrating PSV and EDV measurement processing according to the example of the present disclosure.

In the above-described example, the RI and the PI are estimated from the PSV position and the EDV position estimated by the PSV and EDV automatic measurement and the Doppler trace, but the machine learning model 10 according to the present example may be trained to detect the PSV timing and the EDV timing as illustrated in FIG. 29.

Figure 30:
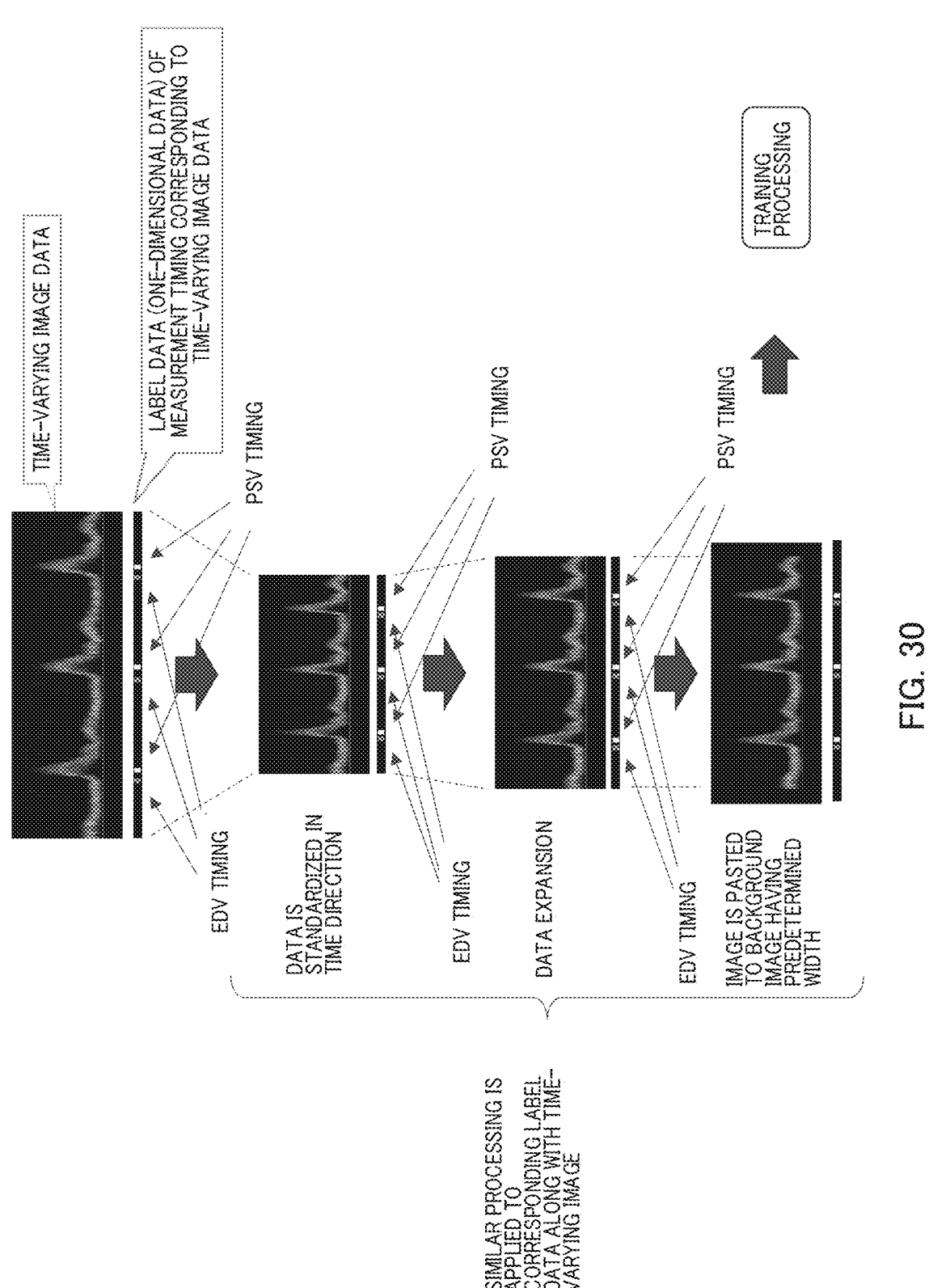
FIG. 30 is a diagram illustrating training processing for PSV and EDV measurement according to the example of the present disclosure.

In the training processing of the machine learning model 10, for example, time-varying image data as illustrated in FIG. 30 and label data on PSV timing and EDV timing corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate as described above, and are enlarged and/or reduced in the time direction, as illustrated. For example, the time-varying image data and the label data illustrated in FIG. 30 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 31:
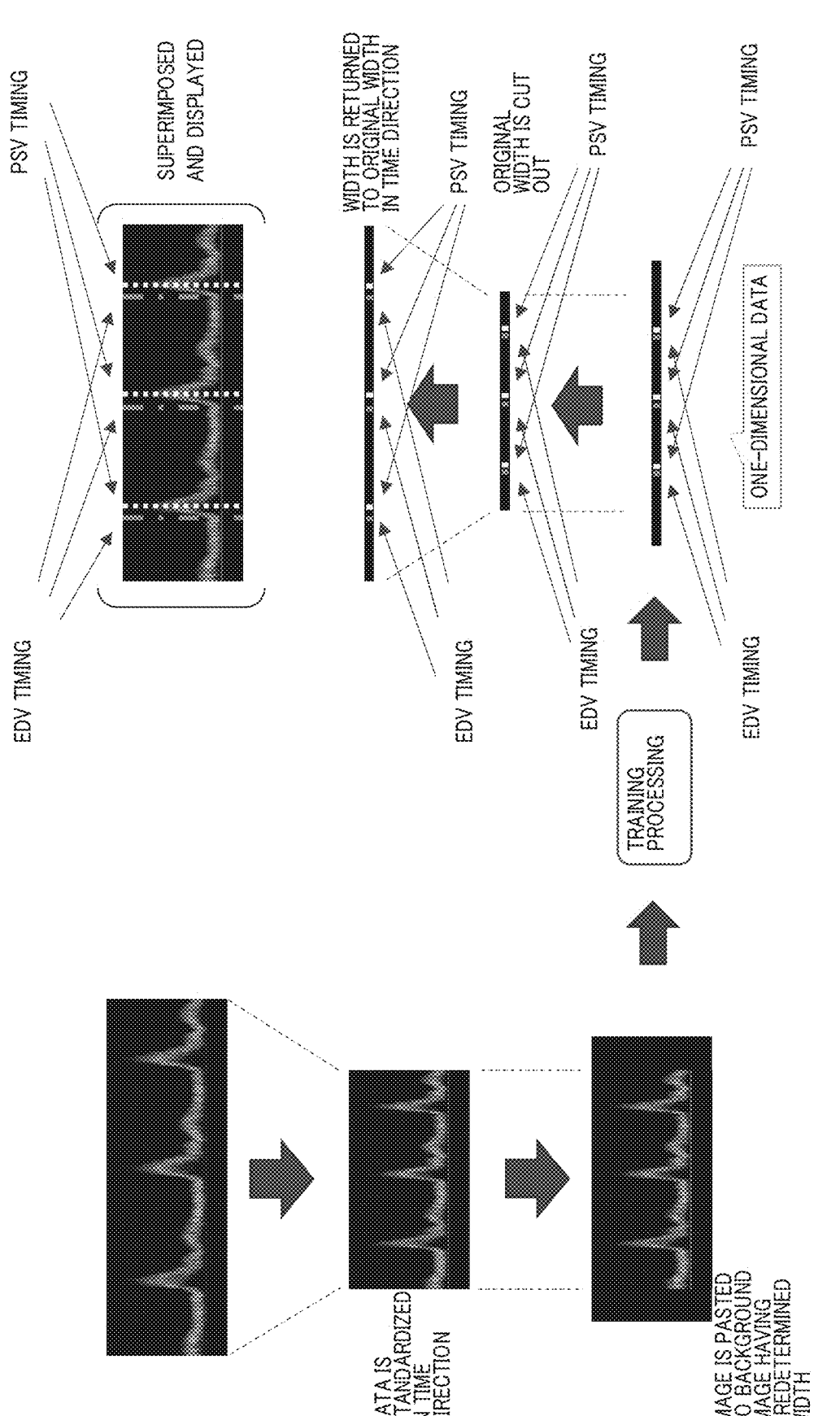
FIG. 31 is a diagram illustrating inference processing for PSV and EDV measurement according an example of the present disclosure.

Next, in the inference processing using the trained machine learning model 10, when time-varying image data of an inference target as illustrated in FIG. 31 is provided, the time-varying image data of the inference target is standardized in the time direction and superimposed on the background image so as to have a predetermined width in the time direction. The standardized time-varying image data having a predetermined time width in this manner is input to the trained machine learning model 10, and as illustrated in FIG. 31, the PSV timing and the EDV timing in the standardized time-varying image data are predicted. The processing opposite to the preprocessing is then performed on the predicted PSV timing and EDV timing. That is, the portion of the background image superimposed in the preprocessing is excluded from the PSV timing and the EDV timing, and thereafter, the width is returned to the original width in the time direction. The PSV timing and the EDV timing acquired in this manner may be superimposed and displayed on the time-varying image data of the inference target.

Figure 32:
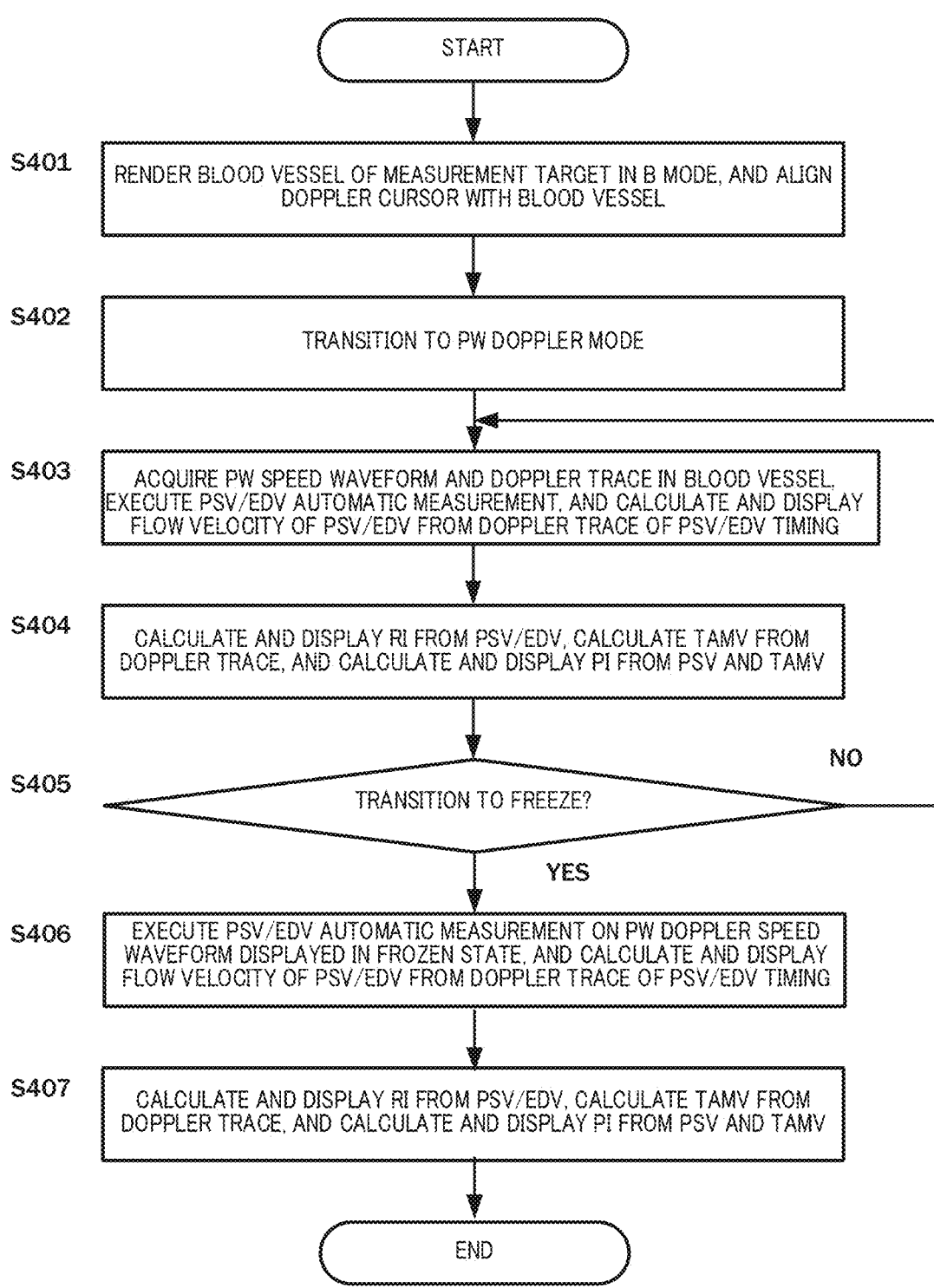
FIG. 32 is a flowchart showing a PSV and EDV measurement process according to an example of the present disclosure.

FIG. 32 is a flowchart illustrating ultrasound diagnostic processing according to an example of the present disclosure. As illustrated in FIG. 32, in step S401, the ultrasound diagnostic apparatus 100 renders a blood vessel of the measurement target in the B mode, and aligns the Doppler cursor with the blood vessel. For example, the ultrasound diagnostic apparatus 100 receives an instruction for a blood vessel portion of the measurement target and a Doppler cursor from the user on the rendered blood vessel.

In step S402, the ultrasound diagnostic apparatus 100 transitions to the PW Doppler mode.

In step S403, the ultrasound diagnostic apparatus 100 acquires a PW speed waveform and a Doppler trace in the blood vessel, executes PSV and EDV automatic measurement on the PW Doppler speed waveform as time-varying image data, and calculates the flow velocity of the PSV and the EDV from the estimated PSV timing, EDV timing, and the Doppler trace, and displays the flow velocity. That is, the ultrasound diagnostic apparatus 100 inputs the PW Doppler speed waveform as time-varying image data of a measurement target to the trained machine learning model 10, and acquires the PSV timing and the EDV timing from the trained machine learning model 10. Next, the ultrasound diagnostic apparatus 100 calculates the flow velocity of the PSV and the EDV from the acquired PSV timing, EDV timing, and the Doppler trace, and displays the flow velocity.

In step S404, the ultrasound diagnostic apparatus 100 calculates and displays a resistance index (RI) from the PSV and the EDV, calculates a time-averaged maximum blood velocity (TAMV) from the Doppler trace, and calculates and displays a pulsatility index (PI) from the PSV and the TAMV.

In step S405, the ultrasound diagnostic apparatus 100 determines whether the state has transitioned to the freeze state. When the state has not transitioned to the freeze state (S405: NO), the ultrasound diagnostic apparatus 100 proceeds to step S403 and repeats the above-described processing. On the other hand, when the state has transitioned to the freeze state (S405: YES), the ultrasound diagnostic apparatus 100 proceeds to step S406.

In step S406, the ultrasound diagnostic apparatus 100 executes the PSV and EDV automatic measurement on the PW Doppler speed waveform displayed in a frozen state, and calculates the flow velocity of the PSV and the EDV from the estimated PSV timing and EDV timing and the Doppler trace and displays the flow velocity. That is, the ultrasound diagnostic apparatus 100 inputs the PW Doppler speed waveform as time-varying image data of a measurement target to the trained machine learning model 10, and acquires the PSV timing and the EDV timing from the trained machine learning model 10. Next, the ultrasound diagnostic apparatus 100 calculates the flow velocity of the PSV and the EDV from the acquired PSV timing, EDV timing, and the Doppler trace, and displays the flow velocity.

In step S407, the ultrasound diagnostic apparatus 100 calculates and displays a resistance index (RI) from the PSV and the EDV, calculates a time-averaged maximum blood velocity (TAMV) from the Doppler trace, and calculates and displays a pulsatility index (PI) from the PSV and the TAMV.

As described above, according to the present example, the PSV and EDV automatic measurement is executed by using the machine learning model 10 trained by the training data including the standardized time-varying image data, the PSV timing, and the EDV timing, and the RI and the PI can be estimated from the time-varying image data acquired from the subject 30, based on the estimated PSV timing and EDV timing, the Doppler trace, and the TAMV calculated from the Doppler trace.

Example of Blood Flow Volume

Figure 33:
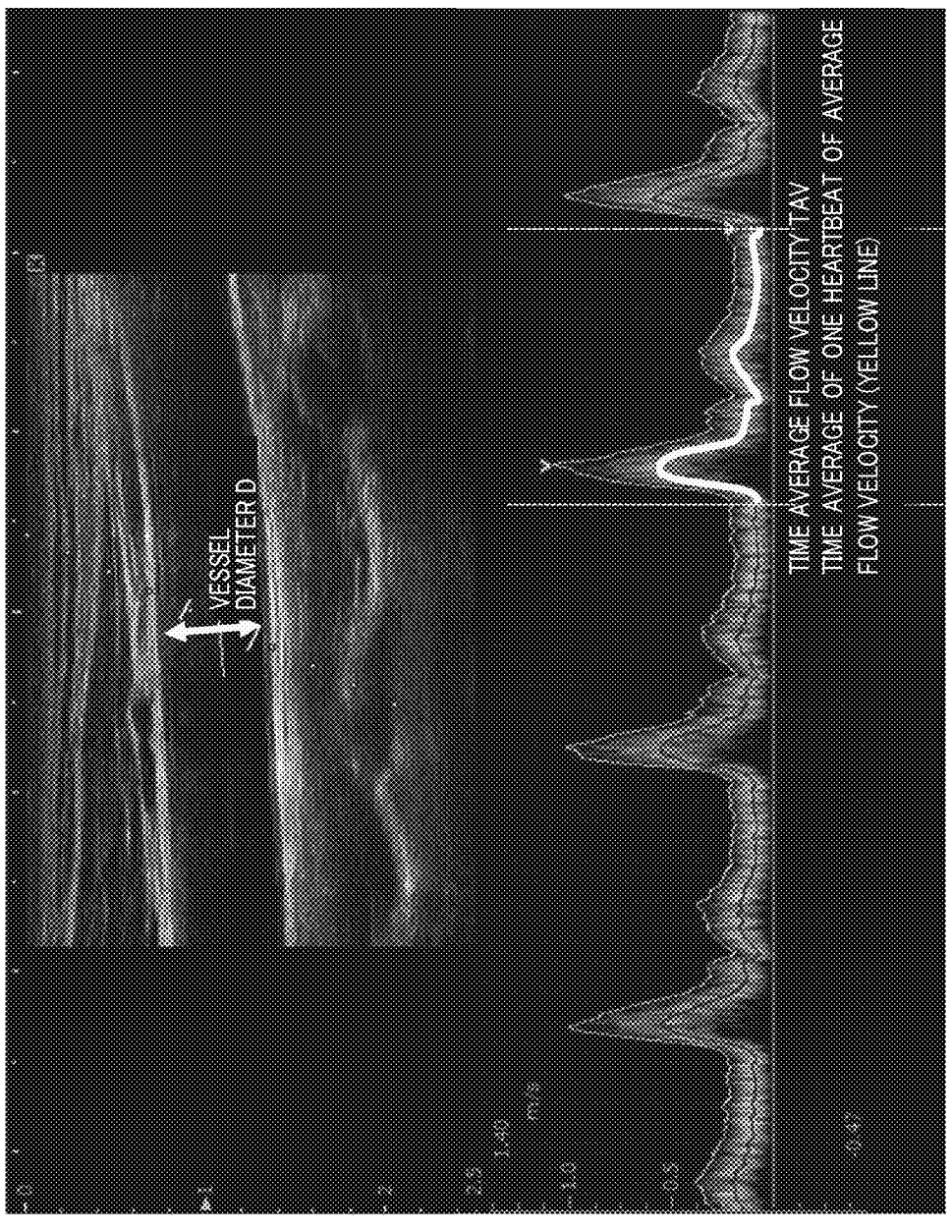
FIG. 33 is a diagram illustrating blood flow volume measurement processing according to the example of the present disclosure.

As illustrated in FIG. 33, the machine learning model 10 can be used to measure blood flow volume (FL). Here, the blood flow volume FL per unit time [mL/min] can be calculated by multiplying the time average blood flow velocity TAV [cm/sec] of one heartbeat, measured by Doppler measurement, by the blood vessel cross-sectional area S [mm$^2$] calculated from the blood vessel diameter D [mm] measured by B-mode measurement. That is, the following is satisfied: $S=\pi\times(D/2)^2$ and $FL=(S/10^2)\times(TAV\times60)$. In order to automatically measure the blood flow volume, the machine learning model 10 is trained to detect a boundary of a blood flow volume measurement target section (that is, a section of one heartbeat) from the input time-varying image data. The illustrated boundaries of the measurement target sections are set on the basis of the timing of the EDV, but the present disclosure is not necessarily limited thereto.

Figure 34:
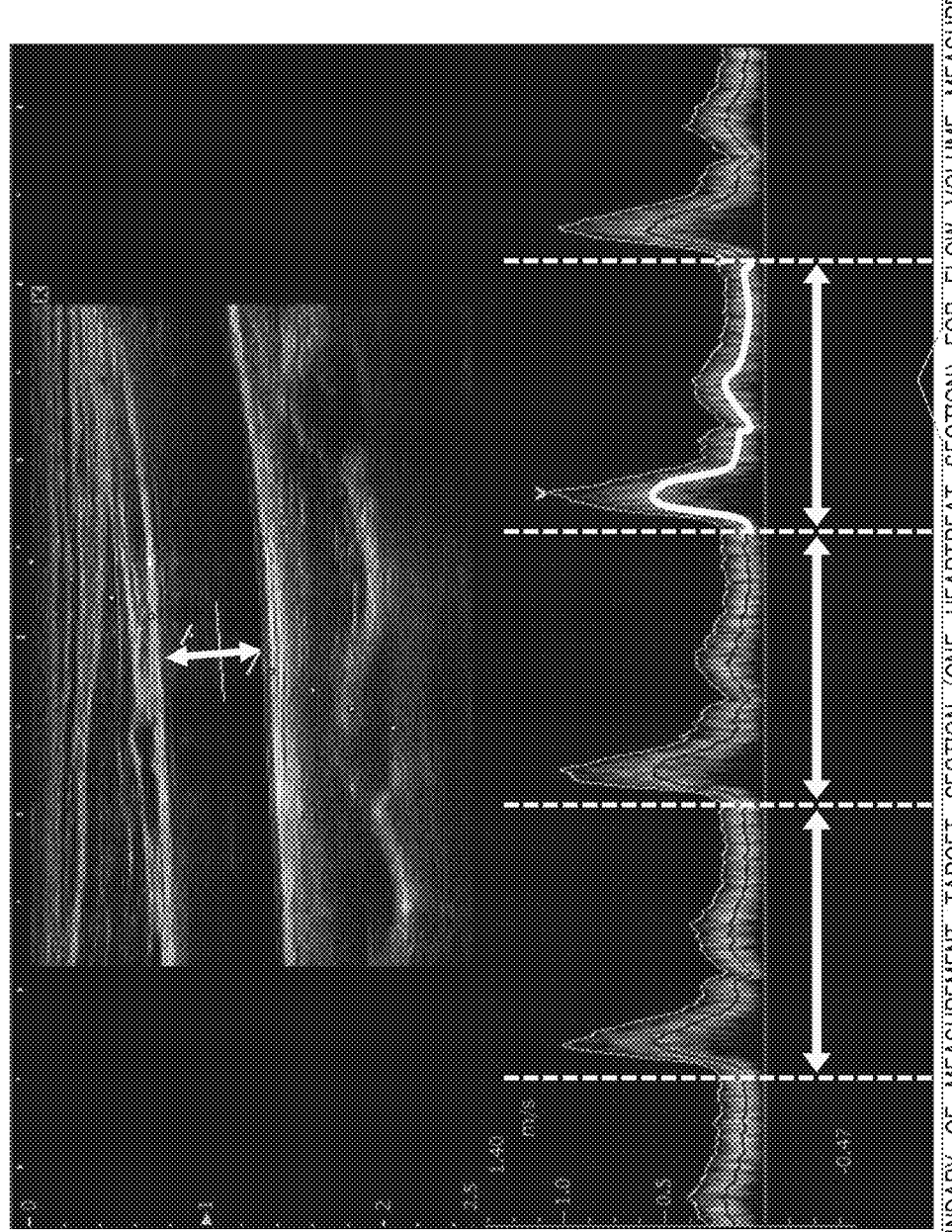
FIG. 34 is a diagram illustrating blood flow volume measurement processing according to the example of the present disclosure.

In the training processing of the machine learning model 10, for example, time-varying image data as illustrated in FIG. 34 and label data on EDV timing corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate, and enlarged and/or reduced in the time direction, as described above. For example, the time-varying image data and the label data are first reduced in the time direction to standardize to have a predetermined sweep speed, and then enlarged in the time direction to standardize to have a predetermined heart rate. The time-varying image data and the label data having been enlarged and reduced in this manner are superimposed on the background image so as to have a predetermined width in the time direction. Then, time-varying image data and label data having the predetermined widths are input to the training processing. Note that the standardization of the training data is the same as that in the example related to the detection of the EDV timing described above, and a detailed description thereof will be omitted to avoid a redundant description.

Next, in the inference processing using the trained machine learning model 10, when time-varying image data of an inference target is provided, the time-varying image data of the inference target is standardized in the time direction and is superimposed on the background image so as to have a predetermined width in the time direction. The standardized time-varying image data having a predetermined time width in this manner is input to the trained machine learning model 10, and the EDV timing in the standardized time-varying image data is predicted. The processing opposite to the preprocessing is then performed on the predicted EDV timing That is, the portion of the background image superimposed in the preprocessing is excluded from the EDV timing, and thereafter, the width is returned to the original width in the time direction. The EDV timing acquired in this manner may be superimposed and displayed on the time-varying image data of the inference target. Note that the standardization of the inference target data is the same as that in the example related to the detection of the EDV timing described above, and a detailed description thereof will be omitted to avoid a redundant description.

FIG. 35 is a flowchart illustrating ultrasound diagnostic processing according to an example of the present disclosure. As illustrated in FIG. 35, in step S501, the ultrasound diagnostic apparatus 100 renders a blood vessel of the measurement target in the B mode, and aligns the Doppler cursor with the blood vessel. For example, the ultrasound diagnostic apparatus 100 receives an instruction for a blood vessel portion of the measurement target and a Doppler cursor from the user on the rendered blood vessel.

In step S502, the ultrasound diagnostic apparatus 100 transitions to the PW Doppler mode.

In step S503, the ultrasound diagnostic apparatus 100 acquires a PW speed waveform and a Doppler trace in the blood vessel and transitions to the freeze state.

In step S504, the ultrasound diagnostic apparatus 100 executes the automatic measurement of the blood flow volume on the PW Doppler speed waveform as the time-varying image data, and detects a measurement target section such as the estimated EDV timing. That is, the ultrasound diagnostic apparatus 100 inputs the PW Doppler speed waveform as time-varying image data of a measurement target to the trained machine learning model 10, and acquires the EDV timing from the trained machine learning model 10.

In step S505, the ultrasound diagnostic apparatus 100 time-averages the average flow velocity in the measurement target section to acquire a time average blood flow velocity TAV.

In step S506, the ultrasound diagnostic apparatus 100 measures the vessel diameter D on the B-mode image.

In step S507, the ultrasound diagnostic apparatus 100 calculates the blood flow volume FL from the time average blood flow velocity TAV and the vessel diameter D. To be more specific, the ultrasound diagnostic apparatus 100 calculates the blood vessel cross-sectional area S from the vessel diameter D in accordance with the equation $S=\pi\times(D/2)^2$ and calculates the blood flow volume FL from the blood vessel cross-sectional area S and the time average blood flow velocity TAV in accordance with the equation $FL=(S/10^2)\times(TAV\times60)$.

As described above, according to the present example, the automatic measurement of the blood flow volume is executed by using the machine learning model 10 trained by the training data including the standardized time-varying image data and the EDV timing, and the blood flow can be estimated from the time-varying image data acquired from the subject 30, based on the estimated EDV timing and the Doppler trace.

Example of E/A Ratio

Figure 36:
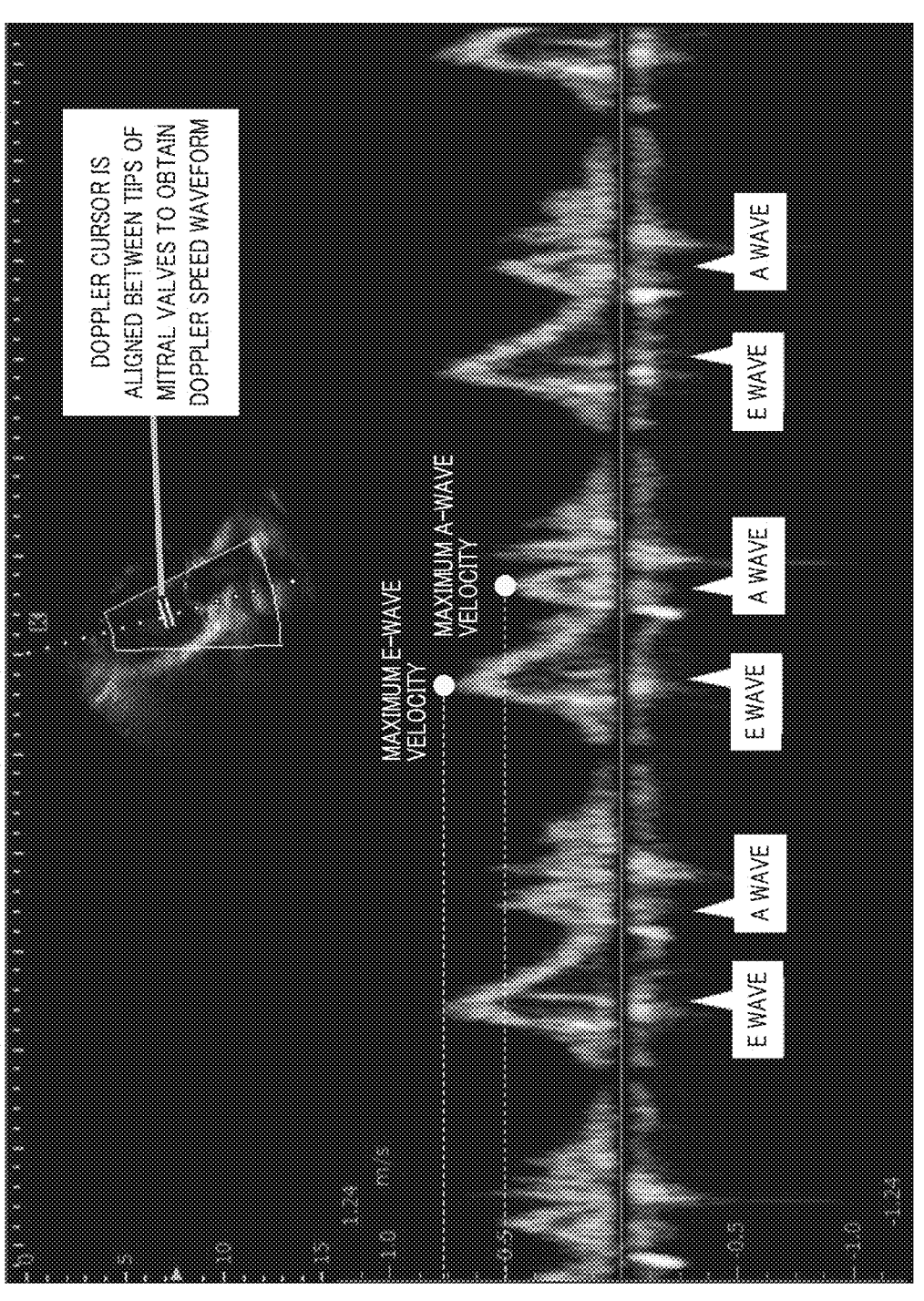
FIG. 36 is a diagram illustrating an E/A ratio measurement process according to the example of the present disclosure.

As illustrated in FIG. 36, the machine learning model 10 according to the present example can be used for E/A ratio measurement. Here, the E/A ratio is an evaluation index of left ventricular diastolic function, and can be calculated according to the equation E/A ratio=maximum E-wave velocity/maximum A-wave velocity. For example, in the case of the E/A≤0.8, the left ventricle is determined to be a relaxation-failure type, and in the case of the E/A≥2.0, the left ventricle is determined to be a restriction type. For automatic E/A ratio measurement, the machine learning model 10 is trained to detect the position of the maximum E-wave velocity and the position of the maximum A-wave velocity from input time-varying image data.

Figure 37:
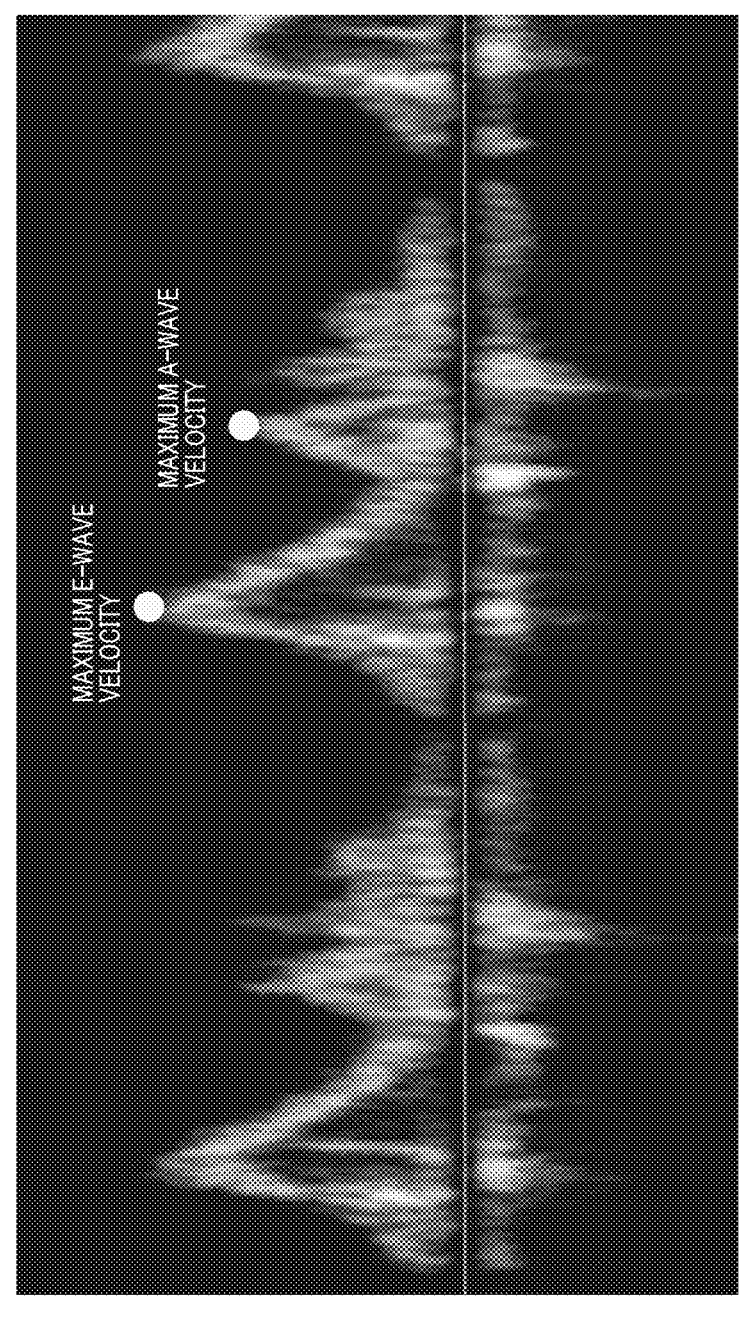
FIG. 37 is a diagram illustrating an E/A ratio measurement process according to the example of the present disclosure.

In the training processing of the machine learning model 10, for example, time-varying image data as illustrated in FIG. 37 and label data on the position of the maximum E-wave velocity and the position of the maximum A-wave velocity corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate, and enlarged and/or reduced in the time direction, as described above. For example, the time-varying image data and the label data are first reduced in the time direction to standardize to have a predetermined sweep speed, and then enlarged in the time direction to standardize to have a predetermined heart rate. The time-varying image data and the label data having been enlarged and reduced in this manner are superimposed on the background image so as to have a predetermined width in the time direction. Then, time-varying image data and label data having the predetermined widths are input to the training processing. Note that the standardization of the training data is the same as that in the example related to the detection of the PSV and EDV positions described above, and details are omitted to avoid redundant description.

Next, in the inference processing using the trained machine learning model 10, when time-varying image data of an inference target is provided, the time-varying image data of the inference target is standardized in the time direction and is superimposed on the background image so as to have a predetermined width in the time direction. The standardized time-varying image data having a predetermined time width in this manner is input to the trained machine learning model 10, and the position of the maximum E-wave velocity and the position of the maximum A-wave velocity in the standardized time-varying image data are predicted. Thereafter, processing opposite to the preprocessing is performed on the predicted position of the maximum E-wave velocity and the position of the maximum A-wave velocity. That is, the portion of the background image superimposed in the preprocessing is excluded from the position of the maximum E-wave velocity and the position of the maximum A-wave velocity, and thereafter, the width is returned to the original width in the time direction. The position of the maximum E-wave velocity and the position of the maximum A-wave velocity acquired in this manner may be superimposed and displayed on the time-varying image data of the inference target. Note that the standardization of the inference target data is similar to that in the above-described example related to the detection of the PSV and EDV positions, and details are omitted to avoid redundant description.

Figure 38:
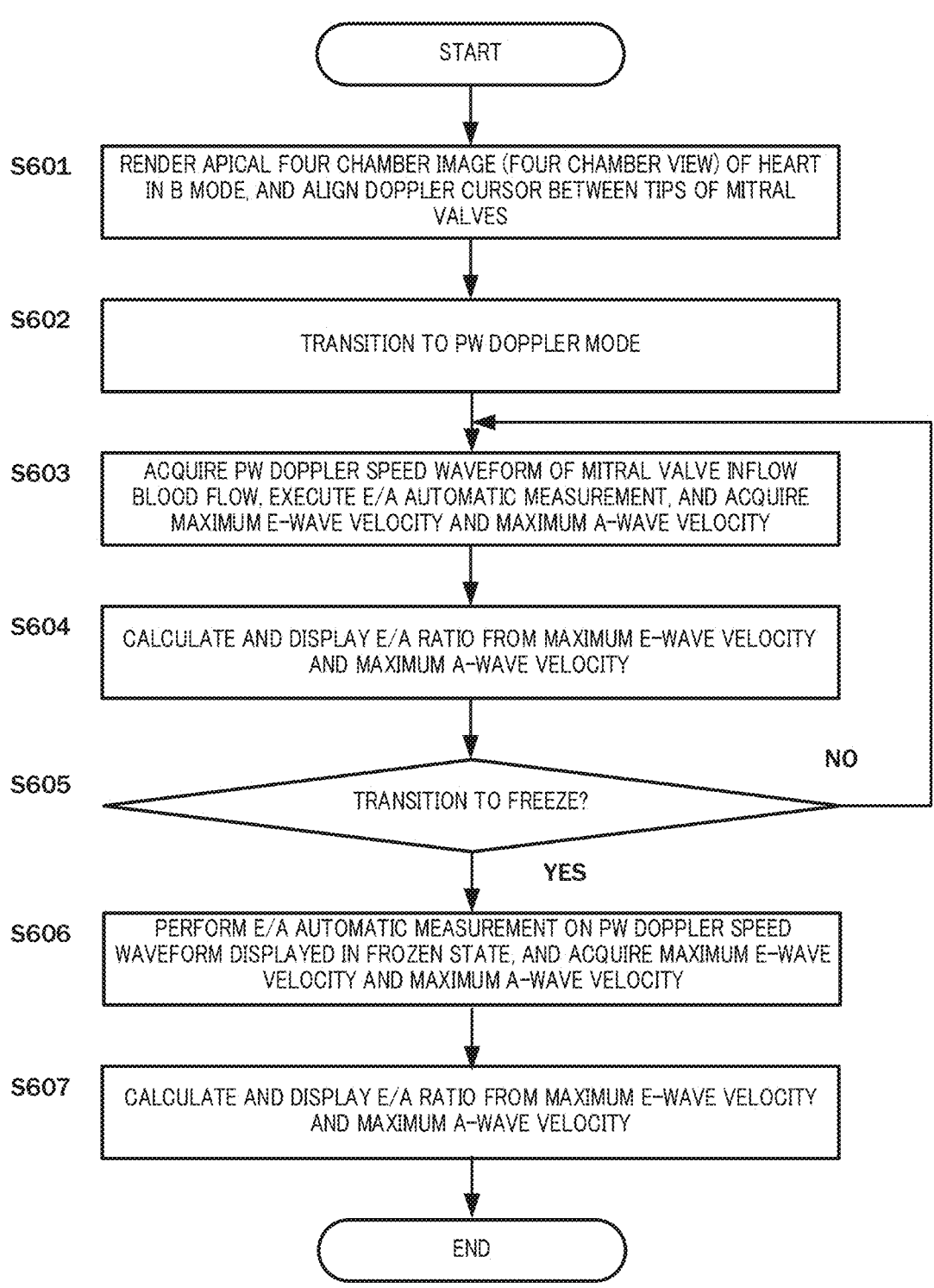
FIG. 38 is a flowchart illustrating E/A ratio measurement processing according to an example of the present disclosure.

FIG. 38 is a flowchart illustrating ultrasound diagnostic processing according to an example of the present disclosure. As illustrated in FIG. 38, in step S601, the ultrasound diagnostic apparatus 100 renders an apical four chamber image (four chamber view) of the heart in the B mode, and aligns the Doppler cursor between the tips of the mitral valves. For example, the ultrasound diagnostic apparatus 100 is instructed by the user for the position of the Doppler cursor on the rendered apical four chamber image.

In step S602, the ultrasound diagnostic apparatus 100 transitions to the PW Doppler mode.

In step S603, the ultrasound diagnostic apparatus 100 acquires the PW Doppler speed waveform of mitral valve inflow blood flow, executes E/A automatic measurement on the PW Doppler speed waveform as time-varying image data, and acquires the maximum E-wave velocity and the maximum A-wave velocity. That is, the ultrasound diagnostic apparatus 100 inputs the PW Doppler speed waveform as the time-varying image data of the measurement target to the trained machine learning model 10, and acquires the position of the maximum E-wave velocity and the position of the maximum A-wave velocity from the trained machine learning model 10.

In step S604, the ultrasound diagnostic apparatus 100 calculates an E/A ratio from the acquired maximum E-wave velocity and maximum A-wave velocity and displays the E/A ratio.

In step S605, the ultrasound diagnostic apparatus 100 determines whether the state has transitioned to the freeze state. When the state has not transitioned to the freeze state (S605: NO), the ultrasound diagnostic apparatus 100 proceeds to step S603 and repeats the above-described processing. On the other hand, when the state has transitioned to the freeze state (S605: YES), the ultrasound diagnostic apparatus 100 proceeds to step S606.

In step S606, the ultrasound diagnostic apparatus 100 performs E/A automatic measurement on the PW Doppler speed waveform displayed in a frozen state, and acquires the maximum E-wave velocity and the maximum A-wave velocity. That is, the ultrasound diagnostic apparatus 100 inputs the PW Doppler speed waveform as the time-varying image data of the measurement target to the trained machine learning model 10, and acquires the position of the maximum E-wave velocity and the position of the maximum A-wave velocity from the trained machine learning model 10. Then, the ultrasound diagnostic apparatus 100 acquires the maximum E-wave velocity and the maximum A-wave velocity from the acquired position of the maximum E-wave velocity and the acquired position of the maximum A-wave velocity.

In step S607, the ultrasound diagnostic apparatus 100 calculates an E/A ratio from the maximum E-wave velocity and the maximum A-wave velocity and displays the E/A ratio.

Thus, according to the present example, the E/A automatic measurement is executed using the machine learning model 10 trained by the training data including the standardized time-varying image data and the position of the maximum E-wave velocity and the position of the maximum A-wave velocity. The E/A ratio thus can be estimated from the time-varying image data acquired from the subject 30, based on the estimated the position of the maximum E-wave velocity and the position of the maximum A-wave velocity.

Figure 39:
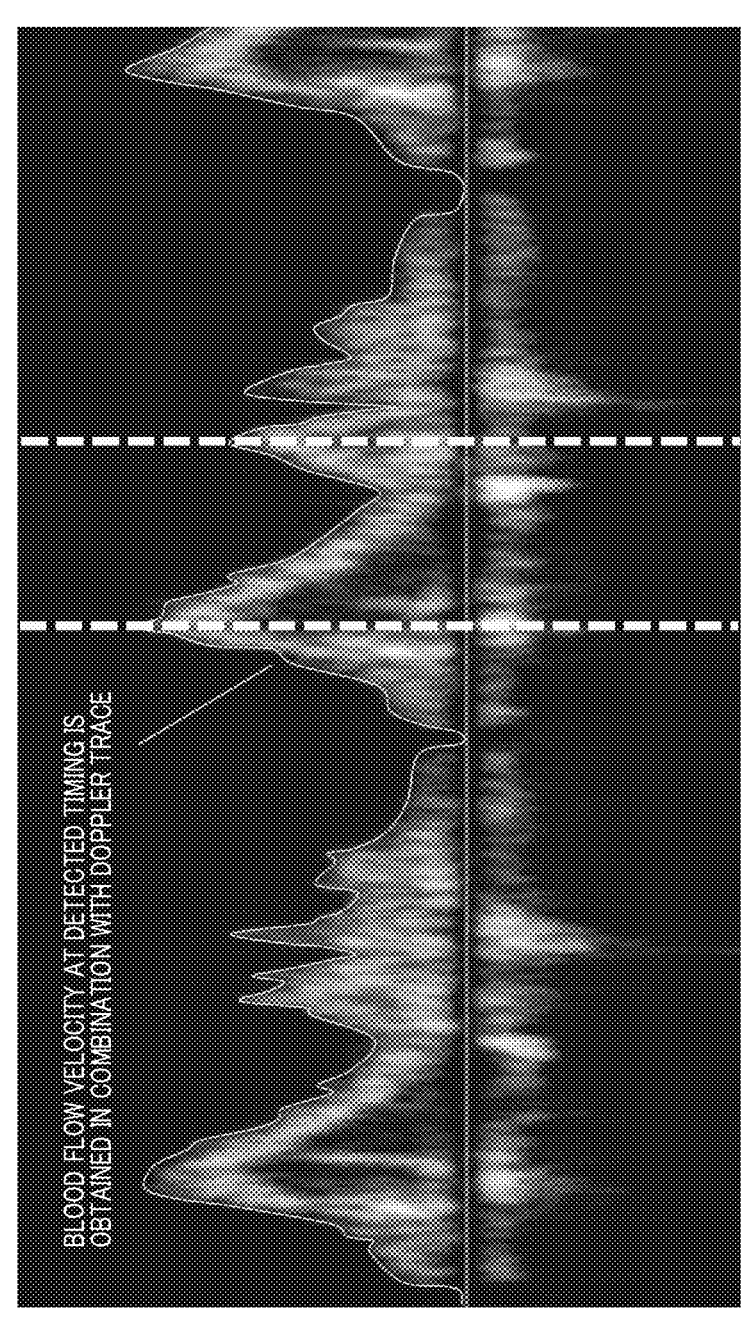
FIG. 39 is a diagram illustrating an E/A ratio measurement process according to the example of the present disclosure.

Although the E/A ratio is estimated from the position of the maximum E-wave velocity and the position of the maximum A-wave velocity estimated by the E/A automatic measurement in the above-described example, the machine learning model 10 according to the present example may be trained to detect the maximum E-wave velocity timing and the maximum A-wave velocity timing, as illustrated in FIG. 39.

In the training processing of the machine learning model 10, for example, time-varying image data as illustrated in FIG. 39 and label data of maximum E-wave velocity timing and maximum A-wave velocity timing corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate as described above, and are enlarged and/or reduced in the time direction, as illustrated. For example, the time-varying image data and the label data are first reduced in the time direction to standardize to have a predetermined sweep speed, and then enlarged in the time direction to standardize to have a predetermined heart rate. The time-varying image data and the label data having been enlarged and reduced in this manner are superimposed on the background image so as to have a predetermined width in the time direction. Then, time-varying image data and label data having the predetermined widths are input to the training processing. Note that the standardization of the training data is the same as that in the example related to the detection of the PSV timing and EDV timing described above, and details are omitted to avoid redundant description.

Next, in the inference processing using the trained machine learning model 10, when time-varying image data of an inference target is provided, the time-varying image data of the inference target is standardized in the time direction and is superimposed on the background image so as to have a predetermined width in the time direction. The standardized time-varying image data having a predetermined time width as described above is input to the trained machine learning model 10, and the machine learning model 10 predicts the maximum E-wave velocity timing and the maximum A-wave velocity timing in the standardized time-varying image data. The processing opposite to the preprocessing is then performed on the predicted maximum E-wave velocity timing and maximum A-wave velocity timing. That is, the portion of the background image superimposed in the preprocessing is excluded from the maximum E-wave velocity timing and the maximum A-wave velocity timing and thereafter, the width is returned to the original width in the time direction. The thus acquired maximum E-wave velocity timing and maximum A-wave velocity timing may be superimposed and displayed on the time-varying image data of the inference target. Note that the standardization of the inference target data is similar to that in the above-described example related to the detection of the PSV timing and EDV timing, and details are omitted to avoid redundant description.

Figure 40:
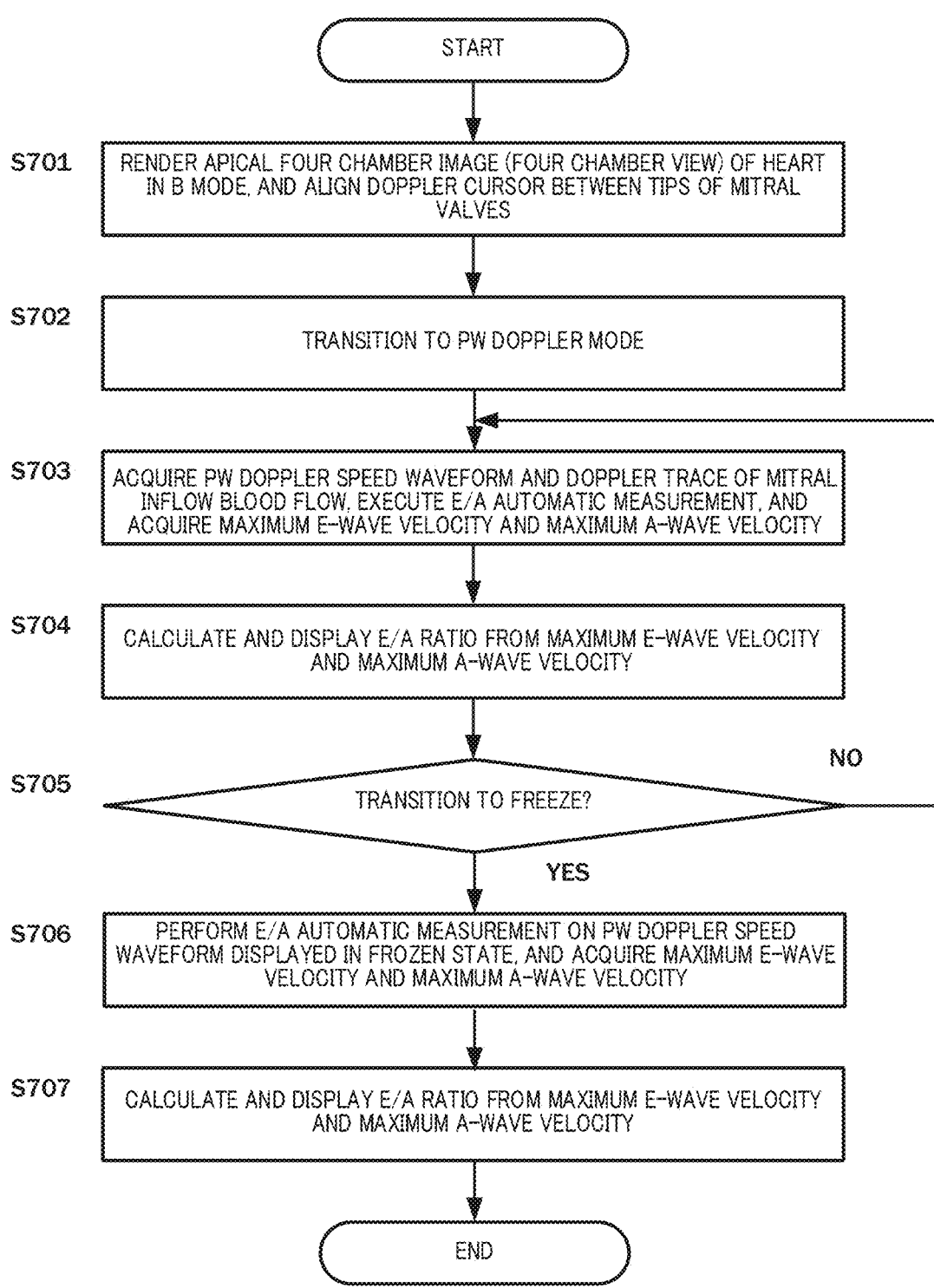
FIG. 40 is a flowchart illustrating E/A ratio measurement processing according to the example of the present disclosure.

FIG. 40 is a flowchart illustrating ultrasound diagnostic processing according to an example of the present disclosure. As illustrated in FIG. 40, in step S701, the ultrasound diagnostic apparatus 100 generates an apical four chamber image (four chamber view) of the apical portion of the heart in the B mode, and positions the Doppler cursor between the tips of the mitral valves. For example, the ultrasound diagnostic apparatus 100 is instructed by the user for the position of the Doppler cursor on the rendered apical four chamber image.

In step S702, the ultrasound diagnostic apparatus 100 transitions to the PW Doppler mode.

In step S703, the ultrasound diagnostic apparatus 100 acquires the PW Doppler speed waveform of the mitral inflow blood flow, executes the E/A automatic measurement on the PW Doppler speed waveform as the time-varying image data, and acquires the maximum E-wave velocity timing and the maximum A-wave velocity timing. That is, the ultrasound diagnostic apparatus 100 inputs the PW Doppler speed waveform as the time-varying image data of the measurement target to the trained machine learning model 10, and acquires the maximum E-wave velocity timing and the maximum A-wave velocity timing from the trained machine learning model 10. Then, the maximum E-wave velocity and the maximum A-wave velocity are acquired from the maximum E-wave velocity timing, the maximum A-wave velocity timing, and the Doppler trace.

In step S704, the ultrasound diagnostic apparatus 100 calculates an E/A ratio from the acquired maximum E-wave velocity and maximum A-wave velocity and displays the E/A ratio.

In step S705, the ultrasound diagnostic apparatus 100 determines whether the state has transitioned to the freeze state. When the state has not transitioned to the freeze state (S705: NO), the ultrasound diagnostic apparatus 100 proceeds to step S703 and repeats the above-described processing. On the other hand, when the state has transitioned to the freeze state (S705: YES), the ultrasound diagnostic apparatus 100 proceeds to step S706.

In step S706, the ultrasound diagnostic apparatus 100 executes E/A automatic measurement for the PW Doppler speed waveform displayed in a frozen state, and acquires the maximum E-wave velocity timing and the maximum A-wave velocity timing. That is, the ultrasound diagnostic apparatus 100 inputs the PW Doppler speed waveform as the time-varying image data of the measurement target to the trained machine learning model 10, and acquires the maximum E-wave velocity timing and the maximum A-wave velocity timing from the trained machine learning model 10. Then, the ultrasound diagnostic apparatus 100 acquires the maximum E-wave velocity and the maximum A-wave velocity from the acquired maximum E-wave velocity timing, maximum A-wave velocity timing, and Doppler trace.

In step S707, the ultrasound diagnostic apparatus 100 calculates an E/A ratio from the maximum E-wave velocity and the maximum A-wave velocity and displays the E/A ratio.

In this manner, according to the present example, the E/A automatic measurement is executed using the machine learning model 10 trained by the training data including the standardized time-varying image data, maximum E-wave velocity timing, and maximum A-wave velocity timing. The E/A ratio thus can be estimated from the time-varying image data acquired from the subject 30, based on the estimated maximum E-wave velocity timing and maximum A-wave velocity timing.

Example of TASTE and MAPSE

Figure 41:
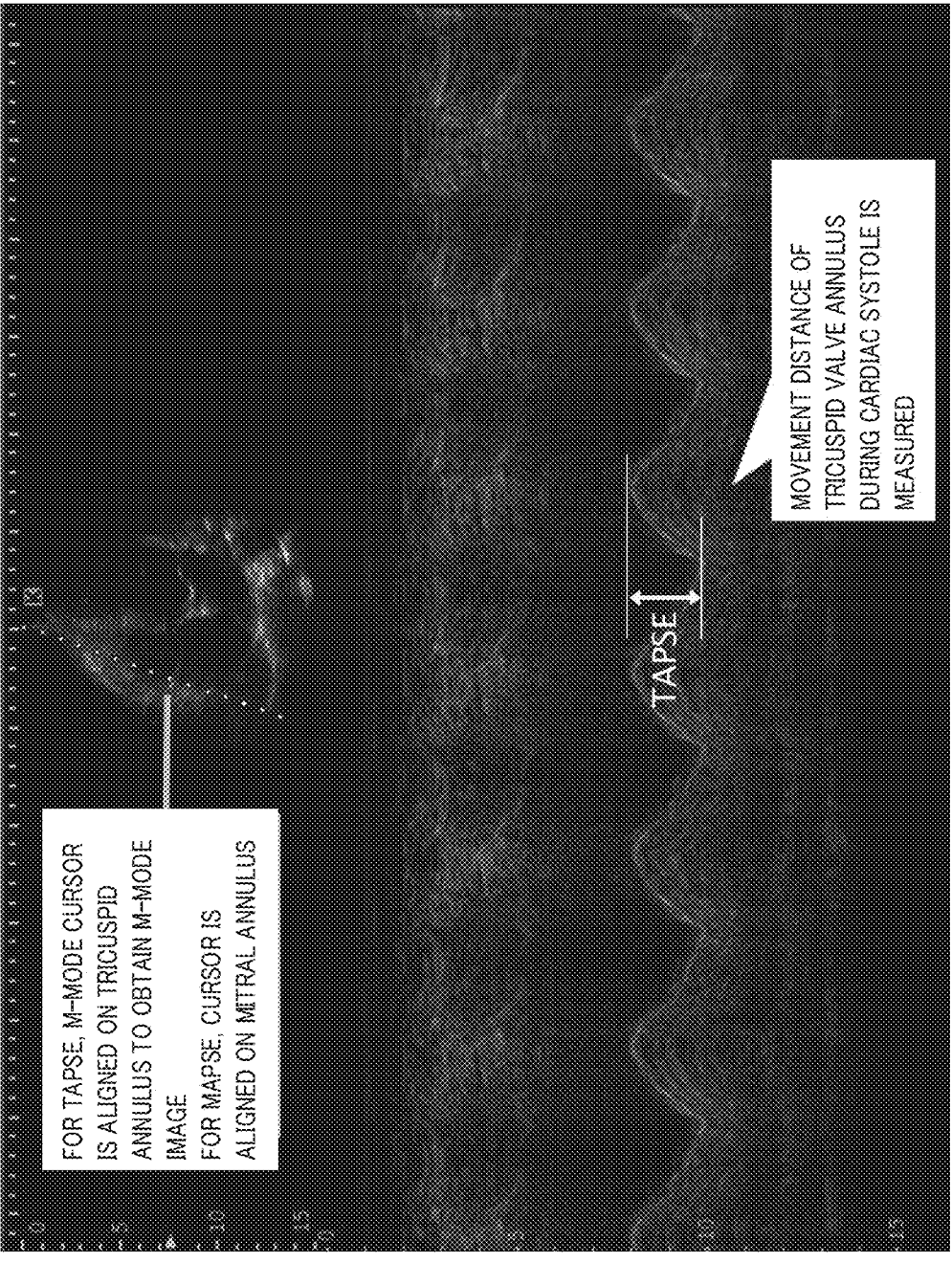
FIG. 41 is a diagram illustrating TAPSE measurement processing according to an example of the present disclosure.
Figure 42:
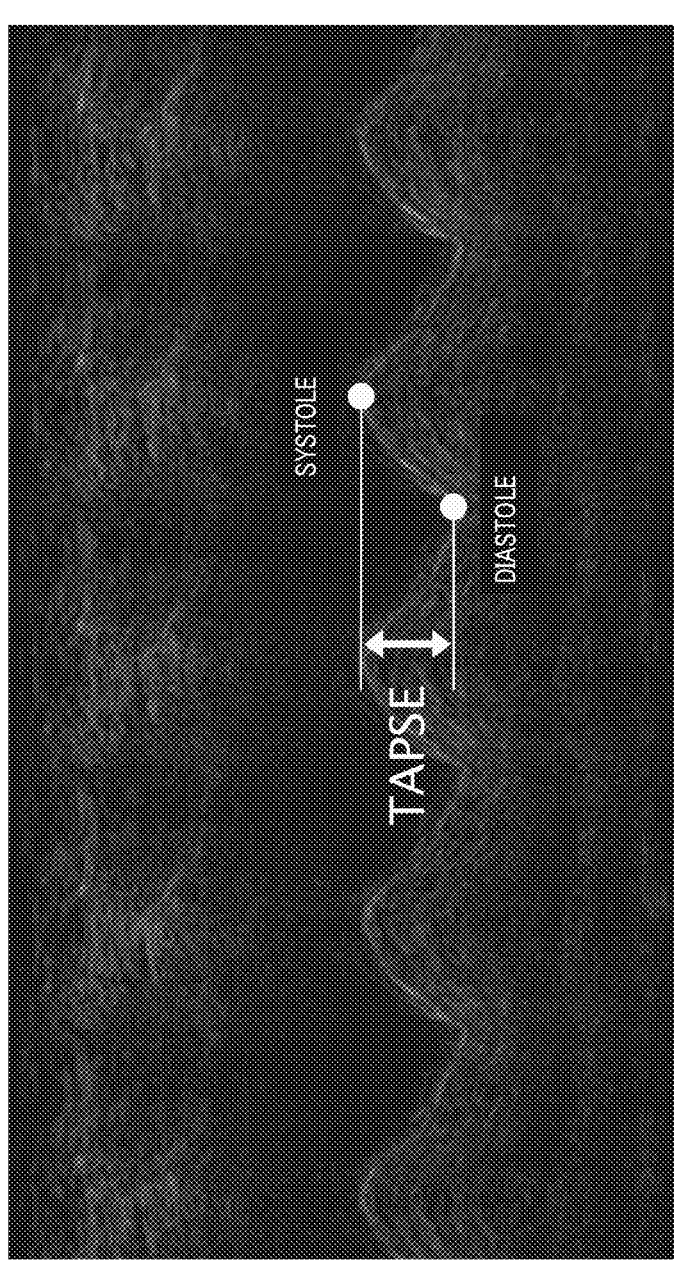
FIG. 42 is a diagram illustrating TAPSE measurement processing according to the example of the present disclosure.

The machine learning model 10 according to the present example can be used for measurement of a tricuspid annulus systolic movement distance (tricuspid annular plane systolic excursion: TAP SE) and/or mitral annular systolic movement distance (mitral annular plane systolic excursion: MAPSE). Here, the TAPSE is an evaluation index of the right heart function, and as illustrated in FIG. 41, is used to evaluate the amount of movement of the annulus of the tricuspid valve in the M mode. In addition, the MAPSE is an evaluation function of the left heart function, can be used in a case where it is difficult to render the left ventricle, and is used to evaluate the amount of movement of the annulus of the mitral valve in the M mode. As illustrated in FIG. 42, the TAPSE can be determined based on the position of the diastole and the position of the systole in the M-mode image, and although not illustrated, the MAPSE can be similarly determined. TAPSE and MAPSE automatic measurement, the machine learning model 10 is trained to detect the diastolic and systolic positions of the TAPSE and/or MAPSE from the input time-varying image data.

Figure 43:
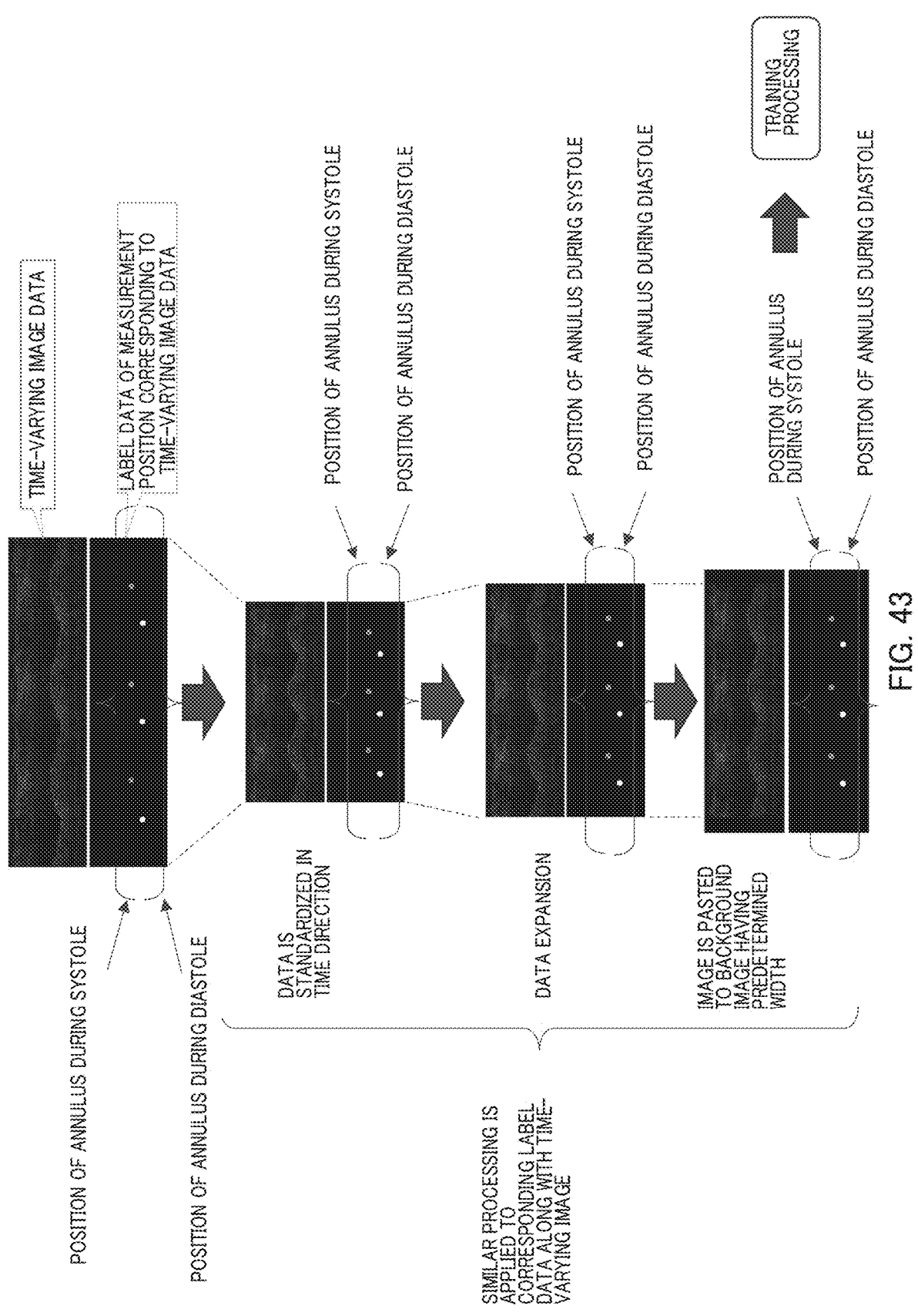
FIG. 43 is a diagram illustrating a training process for TPSE measurement according to the example of the present disclosure.

In the training processing of the machine learning model 10, for example, time-varying image data as illustrated in FIG. 43 and label data on the position of the valve annulus in diastole and the position of the valve annulus in systole corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate, and enlarged and/or reduced in the time direction, as described above. For example, the time-varying image data and the label data illustrated in FIG. 43 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 44:
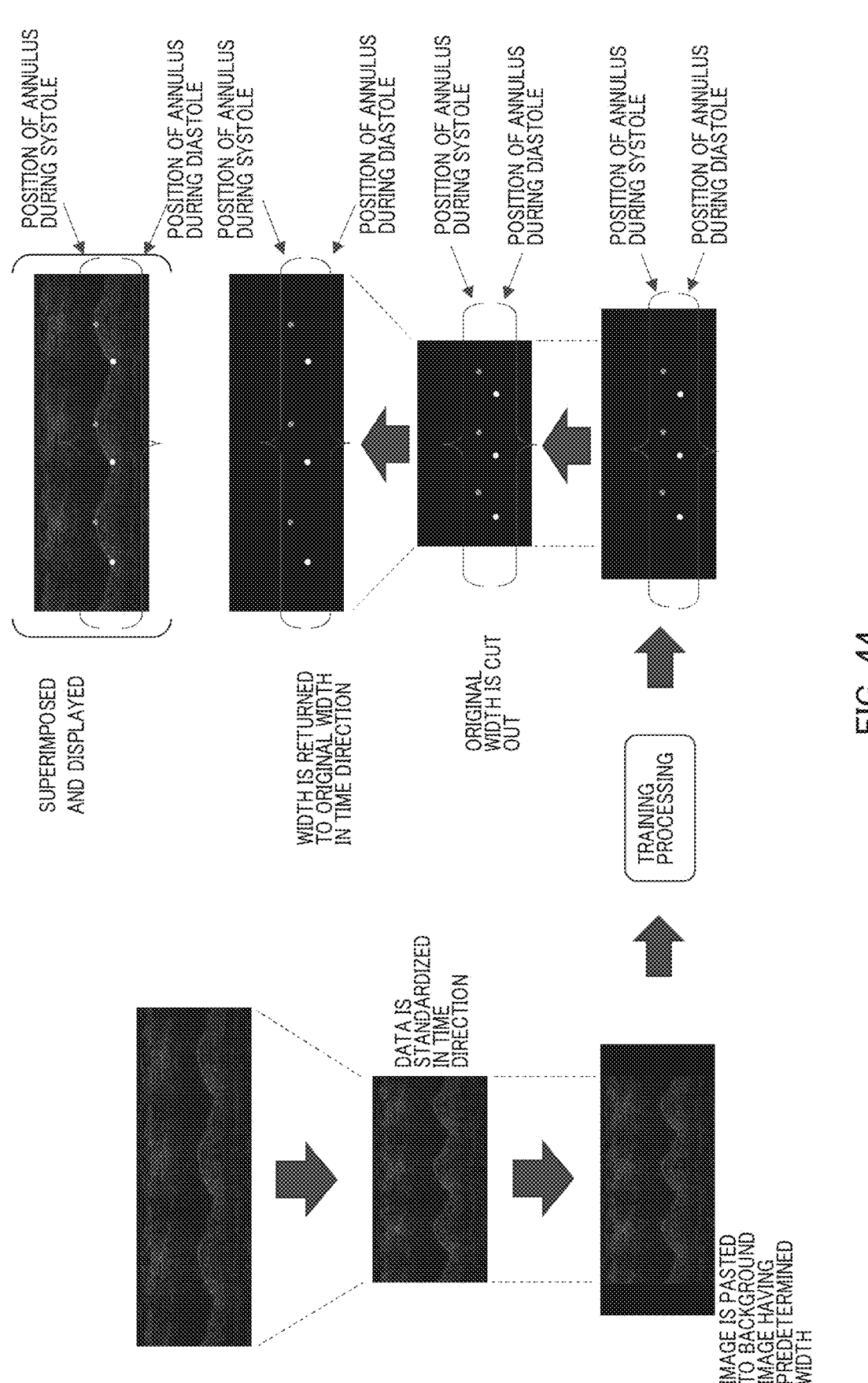
FIG. 44 is a diagram illustrating an inference process for PTSE measurement according to the example of the present disclosure.

Next, in the inference processing using the trained machine learning model 10, when time-varying image data of an inference target is provided as illustrated in FIG. 44, the time-varying image data of the inference target is standardized in the time direction and superimposed on the background image so as to have a predetermined width in the time direction. The standardized time-varying image data having a predetermined time width in this manner is input to the trained machine learning model 10, and the position of the valve annulus in diastole and the position of the valve annulus in systole in the standardized time-varying image data are predicted. The processing opposite to the preprocessing is then performed on the predicted diastolic and systolic annulus positions. That is, the portion of the background image superimposed in the preprocessing is excluded from the position of the annulus in diastole and the position of the annulus in systole, and then the width is returned to the original width in the time direction. The position of the annulus in diastole and the position of the annulus in systole acquired in this manner may be superimposed and displayed on the time-varying image data of the inference target.

Figure 45:
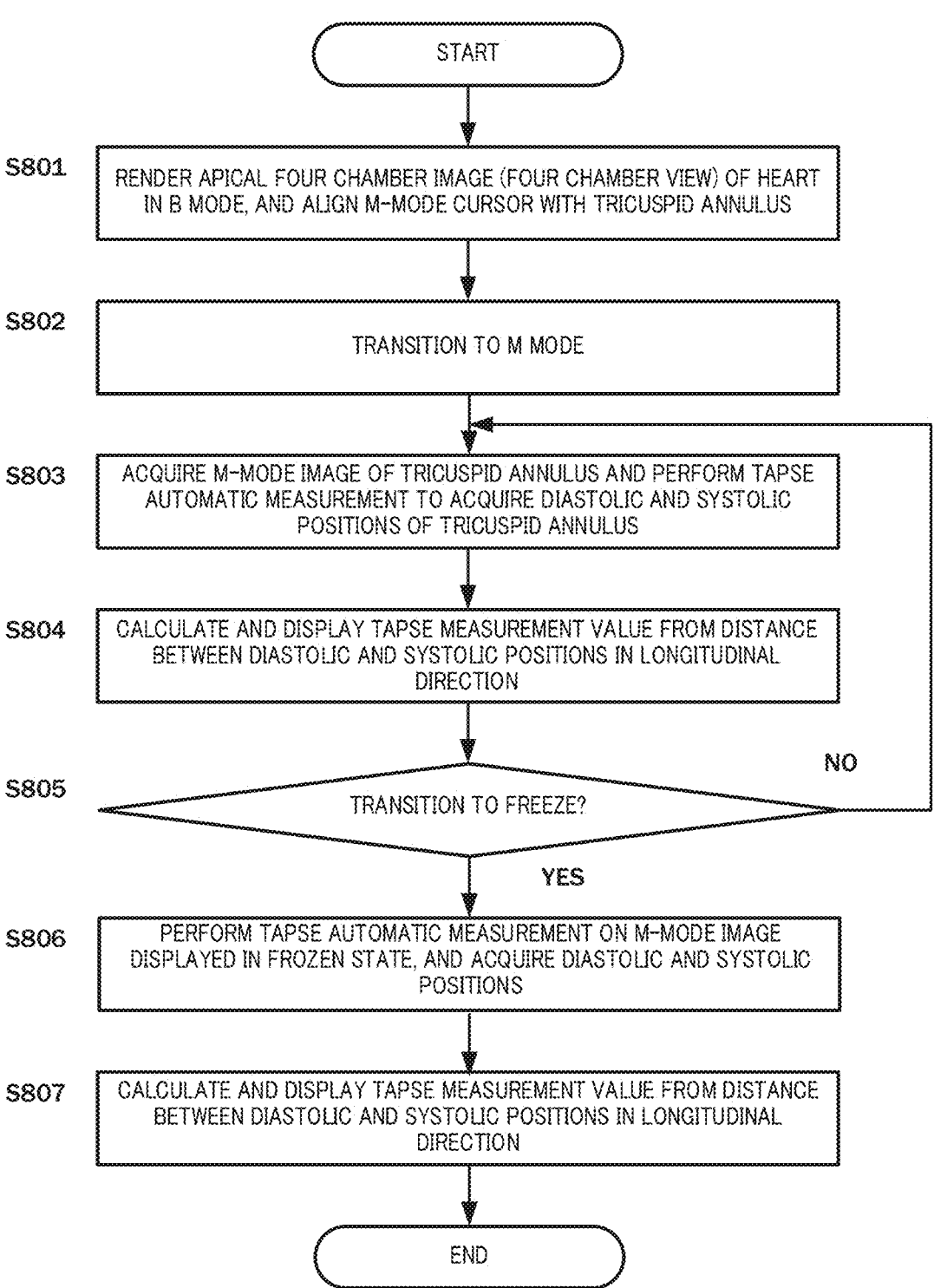
FIG. 45 is a flowchart illustrating TAPSE measurement processing according to an example of the present disclosure.

FIG. 45 is a flowchart illustrating ultrasound diagnostic processing according to an example of the present disclosure. As illustrated in FIG. 45, in step S801, the ultrasound diagnostic apparatus 100 renders an apical four chamber image (four chamber view) of the heart in the B mode, and aligns the M-mode cursor with the tricuspid annulus. For example, the ultrasound diagnostic apparatus 100 is instructed by the user for the position of the M-mode cursor on the rendered apical four chamber image.

In step S802, the ultrasound diagnostic apparatus 100 transitions to the M mode.

In step S803, the ultrasound diagnostic apparatus 100 acquires an M-mode image of the tricuspid annulus and performs TAPSE automatic measurement on the M-mode image as time-varying image data to acquire the positions of the tricuspid annulus in diastole and systole. That is, the ultrasound diagnostic apparatus 100 inputs an M-mode image as time-varying image data of a measurement target to the trained machine learning model 10 and acquires the position of the tricuspid valve annulus in diastole and the position of the tricuspid valve annulus in systole from the trained machine learning model 10.

In step S804, the ultrasound diagnostic apparatus 100 calculates TAPSE values from the acquired positions of the tricuspid annulus in diastole and systole and displays the TAPSE values.

In step S805, the ultrasound diagnostic apparatus 100 determines whether the state has transitioned to the freeze state. When the state has not transitioned to the freeze state (S805: NO), the ultrasound diagnostic apparatus 100 proceeds to step S803 and repeats the above-described processing. On the other hand, when the state has transitioned to the freeze state (S805: YES), the ultrasound diagnostic apparatus 100 proceeds to step S806.

In step S806, the ultrasound diagnostic apparatus 100 performs TAPSE automatic measurement on the M-mode image displayed in a frozen state, and acquires the position of the tricuspid annulus in diastole and the position of the tricuspid annulus in systole. That is, the ultrasound diagnostic apparatus 100 inputs an M-mode image as time-varying image data of a measurement target to the trained machine learning model 10 and acquires the position of the tricuspid valve annulus in diastole and the position of the tricuspid valve annulus in systole from the trained machine learning model 10.

In step S807, the ultrasound diagnostic apparatus 100 calculates TAPSE values from the acquired positions of the tricuspid annulus in diastole and systole and displays the TAPSE value.

As described above, according to the present example, the machine learning model 10 trained by the training data including the standardized time-varying image data and the diastolic and systolic positions of the tricuspid annulus, is used to perform the TAPSE automatic measurement. The TAPSE value thus can be estimated from the time-varying image data acquired from the subject 30, based on the estimated diastolic and systolic positions of the tricuspid annulus.

Note that for MAPSE, the machine learning model 10 trained to estimate the diastolic and systolic positions of the mitral annulus in M-mode images can be used to obtain MAPSE values in a similar manner.

Figure 46:
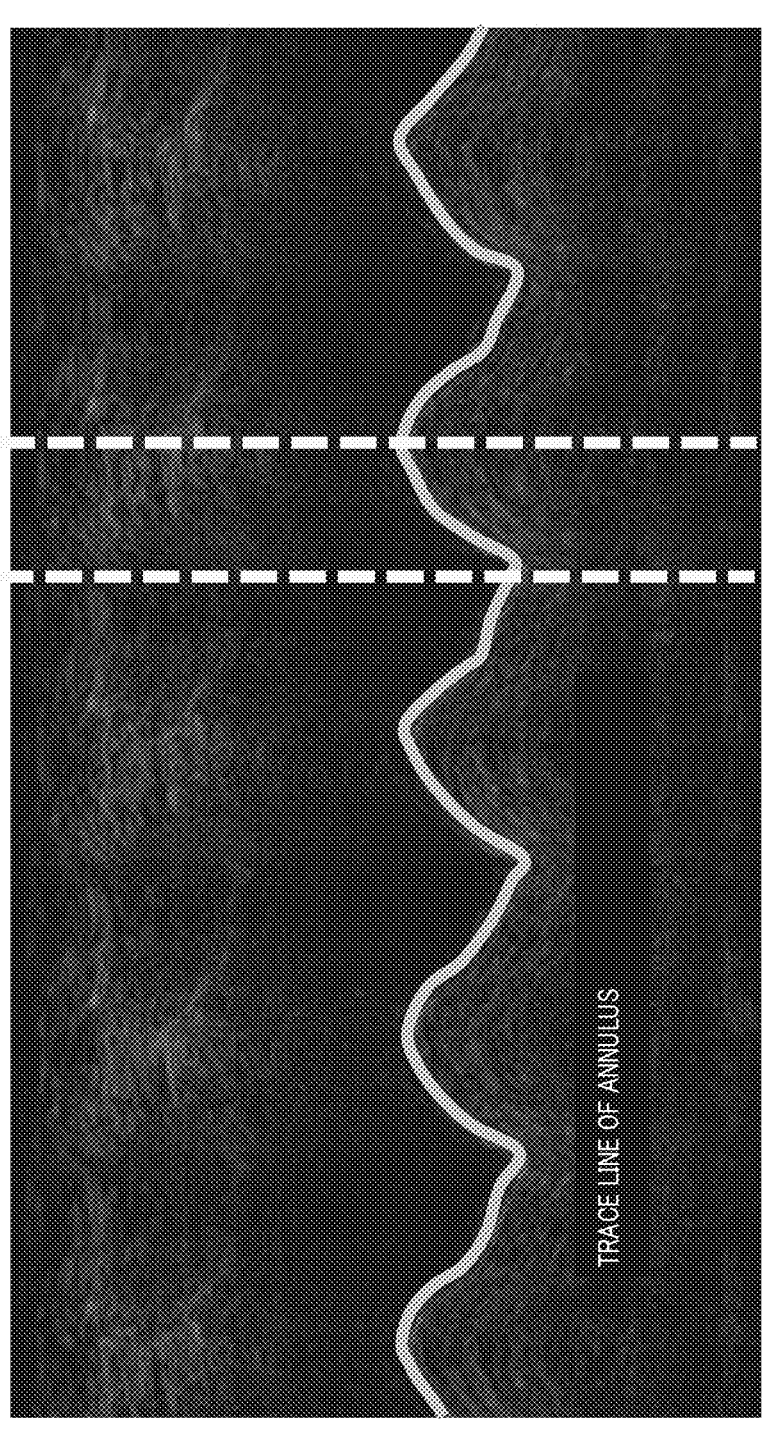
FIG. 46 is a diagram illustrating TAPSE measurement processing according to the example of the present disclosure.

Although the TAPSE value is estimated from the diastolic position and the systolic position of the tricuspid valve annulus and estimated by the TAPSE automatic measurement in the above-described example, the machine learning model 10 according to the present example may be trained to detect the diastolic timing and the systolic timing of the tricuspid valve annulus, as illustrated in FIG. 46.

Figure 47:
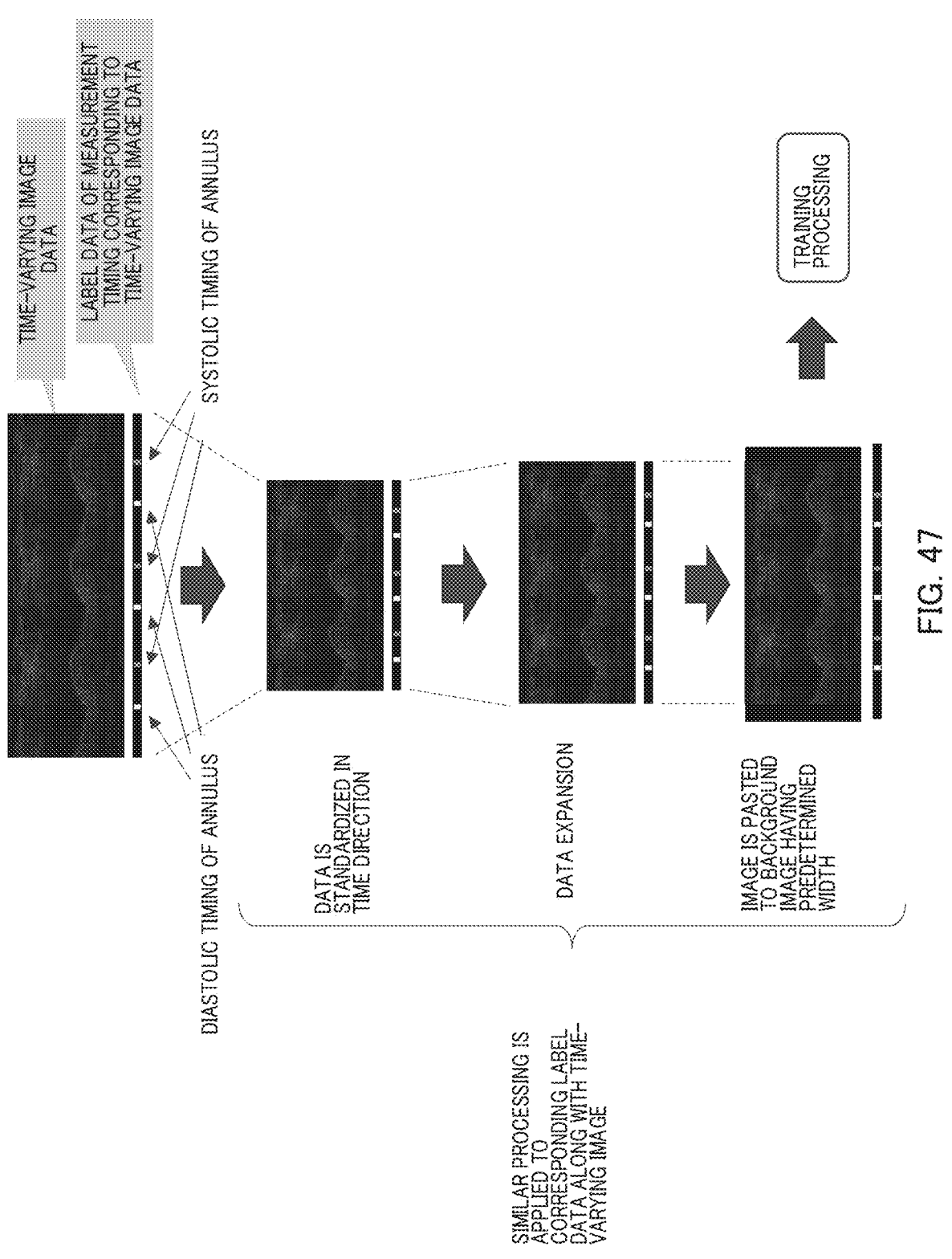
FIG. 47 is a diagram illustrating training processing for TPSE measurement according to the example of the present disclosure.

In the training processing of the machine learning model 10, for example, time-varying image data as illustrated in FIG. 47 and label data of the diastolic timing and the systolic timing corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate, and enlarged and/or reduced in the time direction, as described above. For example, the time-varying image data and the label data illustrated in FIG. 47 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 48:
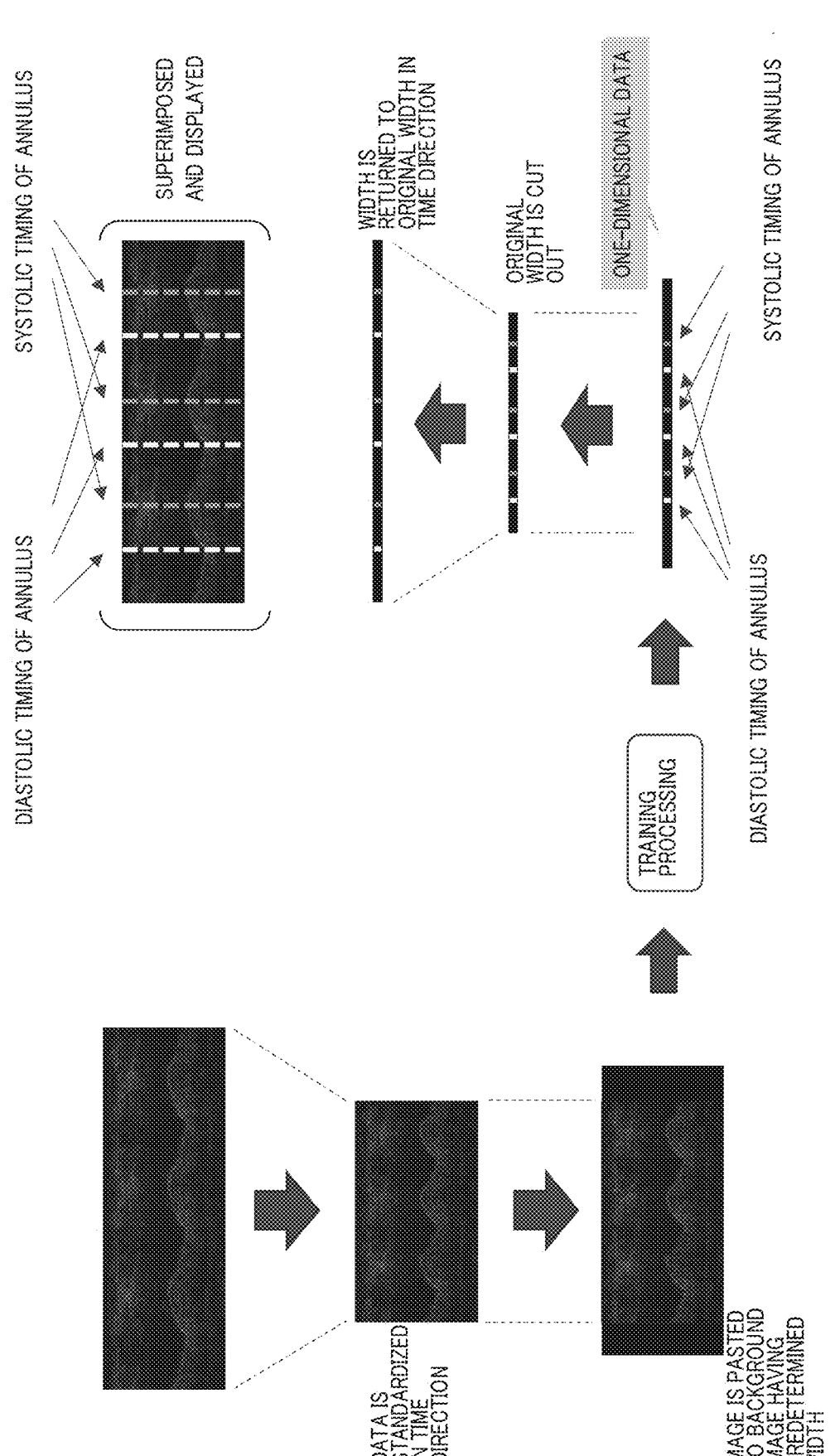
FIG. 48 is a diagram illustrating inference processing for TAPSE instrumentation according to the example of the present disclosure.

Next, in the inference processing using the trained machine learning model 10, when time-varying image data of an inference target is provided as illustrated in FIG. 48, the time-varying image data of the inference target is standardized in the time direction and superimposed on the background image so as to have a predetermined width in the time direction. The standardized time-varying image data having a predetermined time width in this manner is input to the trained machine learning model 10, and the diastolic timing and the systolic timing in the standardized time-varying image data are predicted. The processing opposite to the preprocessing is then performed on the predicted diastolic timing and systolic timing. That is, the portion of the background image superimposed in the preprocessing is excluded from the diastole timing and the systole timing, and then the width is returned to the original width in the time direction. The diastolic timing and the systolic timing acquired in this manner may be superimposed and displayed on the time-varying image data of the inference target.

Figure 49:
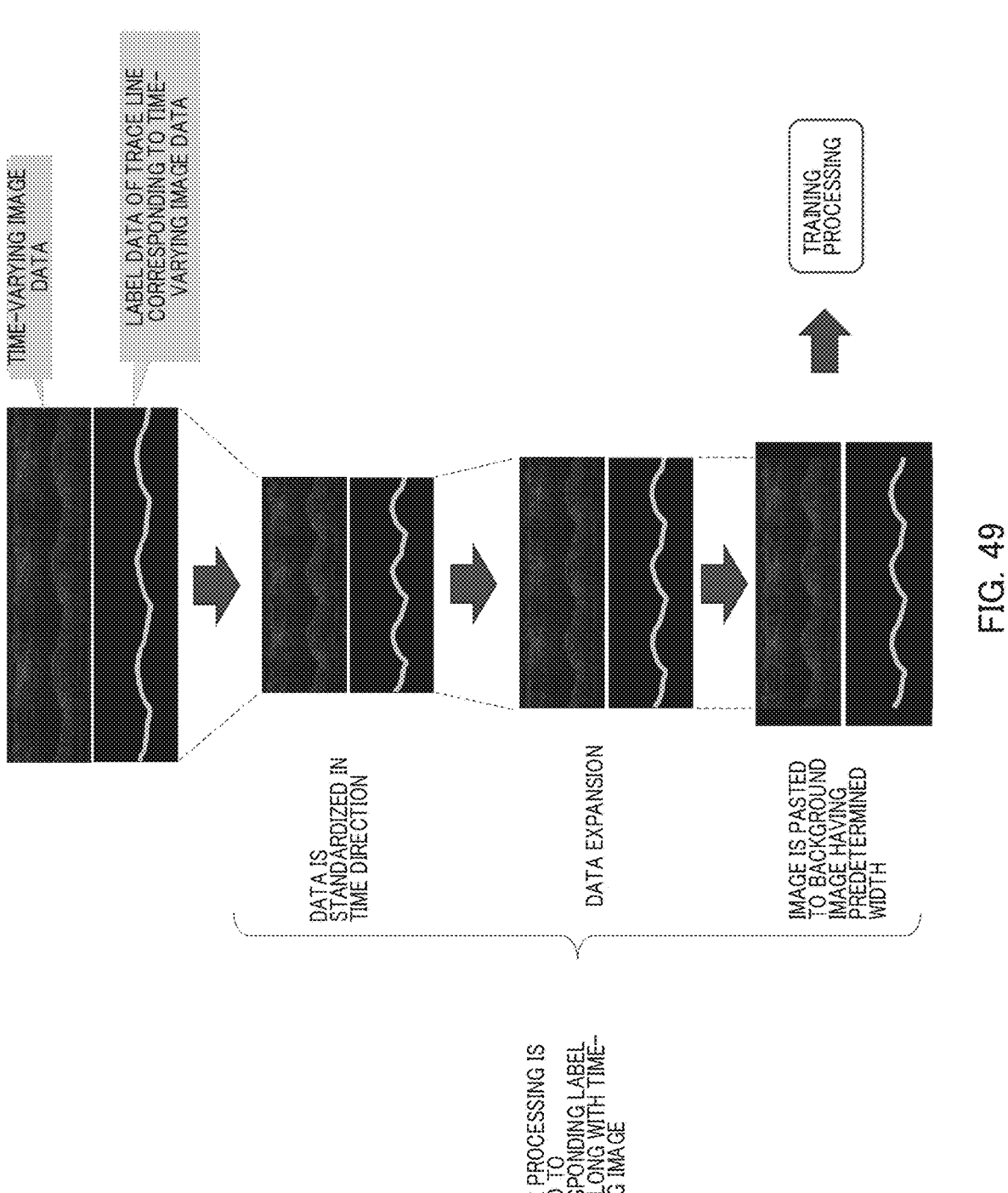
FIG. 49 is a diagram illustrating training processing for TPSE measurement according to the example of the present disclosure.

Further, as illustrated in FIG. 49, the machine learning model 10 according to the present example may be trained to detect trace lines of the tricuspid valve annulus in the M-mode image. In the training processing of the machine learning model 10, for example, time-varying image data as illustrated in FIG. 49 and label data of the trace line of the tricuspid valve annulus corresponding to the time-varying image data are prepared as training data. Since the time-varying image data for training is acquired at different sweep speeds and/or different heart rates, the time-varying image data and the label data are standardized to have a predetermined sweep speed and/or a predetermined heart rate, and enlarged and/or reduced in the time direction, as described above. For example, the time-varying image data and the label data illustrated in FIG. 48 are first reduced in the time direction in order to be standardized to have a predetermined sweep speed, and then enlarged in the time direction in order to be standardized to have a predetermined heart rate. The time-varying image data and the label data having been enlarged and reduced in this manner are superimposed on the background image so as to have a predetermined width in the time direction. Then, time-varying image data and label data having the predetermined widths are input to the training processing.

Figure 50:
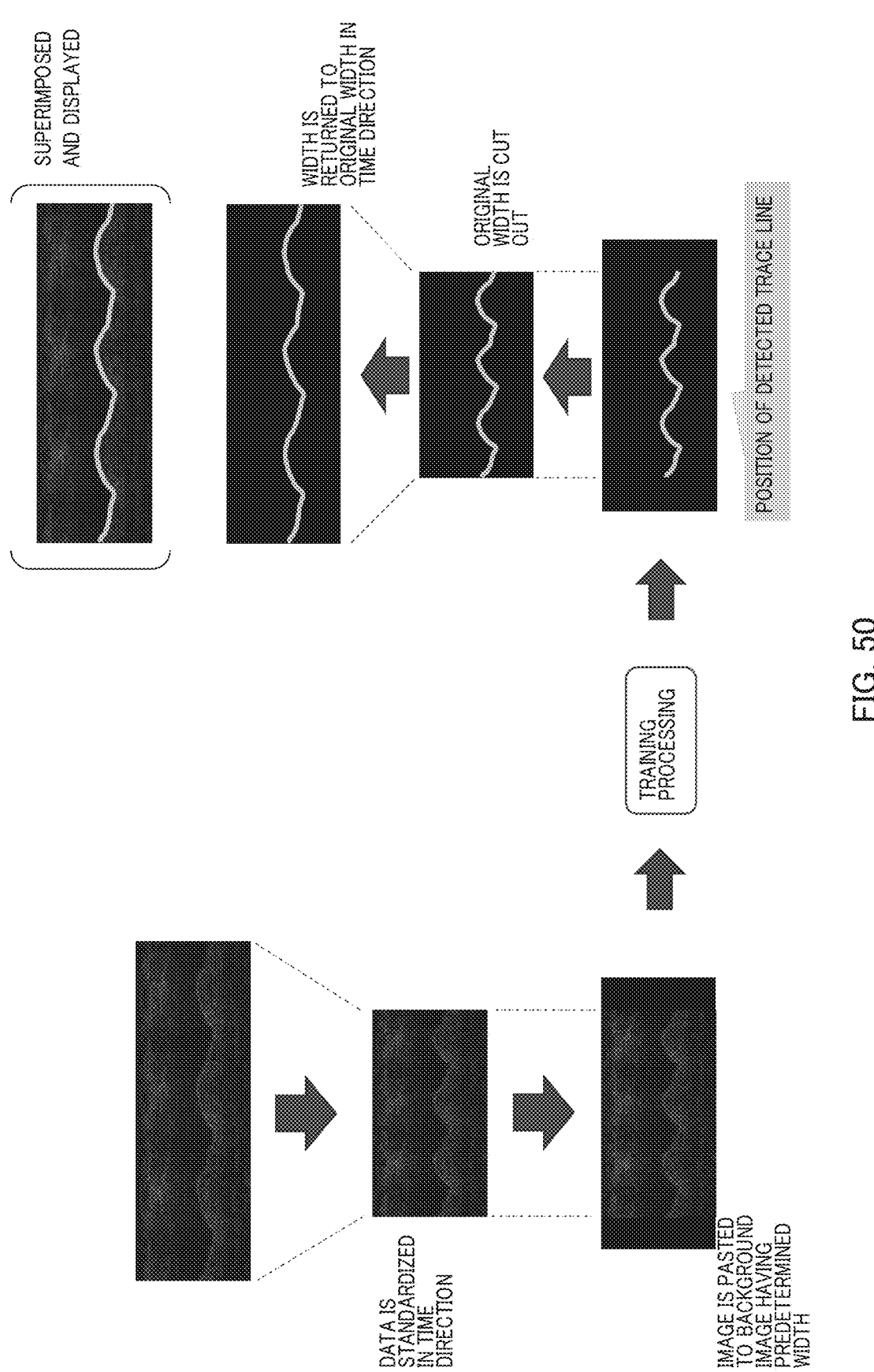
FIG. 50 is a diagram illustrating inference processing for PTSE measurement according to the example of the present disclosure.

Next, in the inference processing using the trained machine learning model 10, when time-varying image data of an inference target is provided as illustrated in FIG. 50, the time-varying image data of the inference target is standardized in the time direction and superimposed on the background image so as to have a predetermined width in the time direction. The standardized time-varying image data having a predetermined time width in this manner is input to the trained machine learning model 10, and the position of the trace line of the tricuspid valve annulus in the standardized time-varying image data are predicted. The processing opposite to the preprocessing is then performed on the predicted trace line of the tricuspid annulus That is, the portion of the background image superimposed in the preprocessing is excluded from the trace line of the tricuspid valve annulus, and thereafter, the width is returned to the original width in the time direction. The trace line of the tricuspid valve annulus thus acquired may be superimposed and displayed on the time-varying image data of the inference target.

Figure 51:
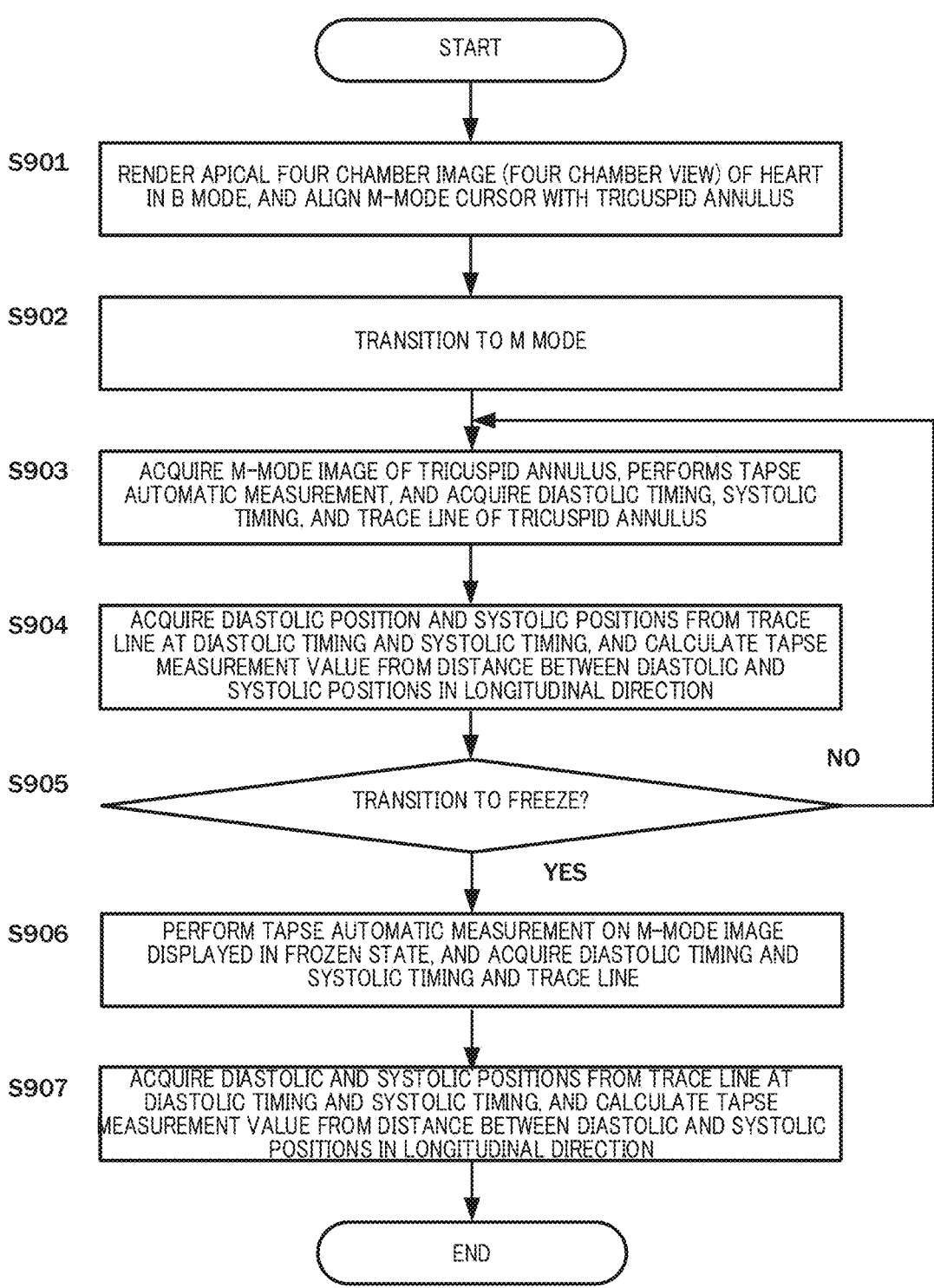
FIG. 51 is a flowchart illustrating PTSE measurement processing according to an example of the present disclosure.

FIG. 51 is a flowchart illustrating ultrasonic diagnostic processing according to an example of the present disclosure. As illustrated in FIG. 51, in step S901, the ultrasound diagnostic apparatus 100 renders an apical four chamber image (four chamber view) of the heart in the B-mode, and aligns the M-mode cursor with the tricuspid annulus. For example, the ultrasound diagnostic apparatus 100 is instructed by the user for the position of the M-mode cursor on the rendered apical four chamber image.

In step S902, the ultrasound diagnostic apparatus 100 transitions to the M mode.

In step S903, the ultrasound diagnostic apparatus 100 acquires an M-mode image of the tricuspid annulus, performs TAPSE automatic measurement on the M-mode image, and acquires the diastolic timing, the systolic timing, and the trace lines of the tricuspid annulus. That is, the ultrasound diagnostic apparatus 100 inputs an M-mode image as time-varying image data of a measurement target to the trained machine learning model 10, and acquires a diastolic timing and a systolic timing of the tricuspid valve annulus and a trace line from the trained machine learning model 10.

In step S904, the ultrasound diagnostic apparatus 100 acquires a diastolic position and a systolic position from the acquired trace lines at the diastolic timing and the systolic timing of the tricuspid annulus, and calculates a TAPSE value from the diastolic position and the systolic position and displays the TAPSE value.

In step S905, the ultrasound diagnostic apparatus 100 determines whether the state has transitioned to the freeze state. When the state has not transitioned to the freeze state (S905: NO), the ultrasound diagnostic apparatus 100 proceeds to step S903 and repeats the above-described processing. On the other hand, when the state has transitioned to the freeze state (S905: YES), the ultrasound diagnostic apparatus 100 proceeds to step S906.

In step S906, the ultrasound diagnostic apparatus 100 performs TAPSE automatic measurement on the M-mode image displayed in a frozen state, and acquires the diastolic timing and the systolic timing of the tricuspid annulus and a trace line. That is, the ultrasound diagnostic apparatus 100 inputs an M-mode image as time-varying image data of a measurement target to the trained machine learning model 10, and acquires a diastolic timing and a systolic timing of the tricuspid valve annulus and a trace line from the trained machine learning model 10.

In step S907, the ultrasound diagnostic apparatus 100 acquires a diastolic position and a systolic position from the acquired trace line at the diastolic timing and the systolic timing of the tricuspid annulus, and calculates a TAPSE value from the diastolic position and the systolic position and displays the TAPSE value.

In this manner, according to the present example, TAPSE automatic measurement is executed by using the machine learning model 10 trained by the training data including the standardized time-varying image data and the diastolic timing and systolic timing and the trace line of the tricuspid valve annulus, and a TAP SE value can be estimated from the time-varying image data acquired from the subject 30 on the basis of the estimated diastolic and systolic timings and the trace line of the tricuspid valve annulus.

Note that with respect to MAPSE, a MAP SE value can be similarly acquired by using the machine learning model 10 trained to estimate diastolic timing and systolic timing and the trace line of the mitral annulus in an M-mode image.

Example of IVC Diameter

Figure 52:
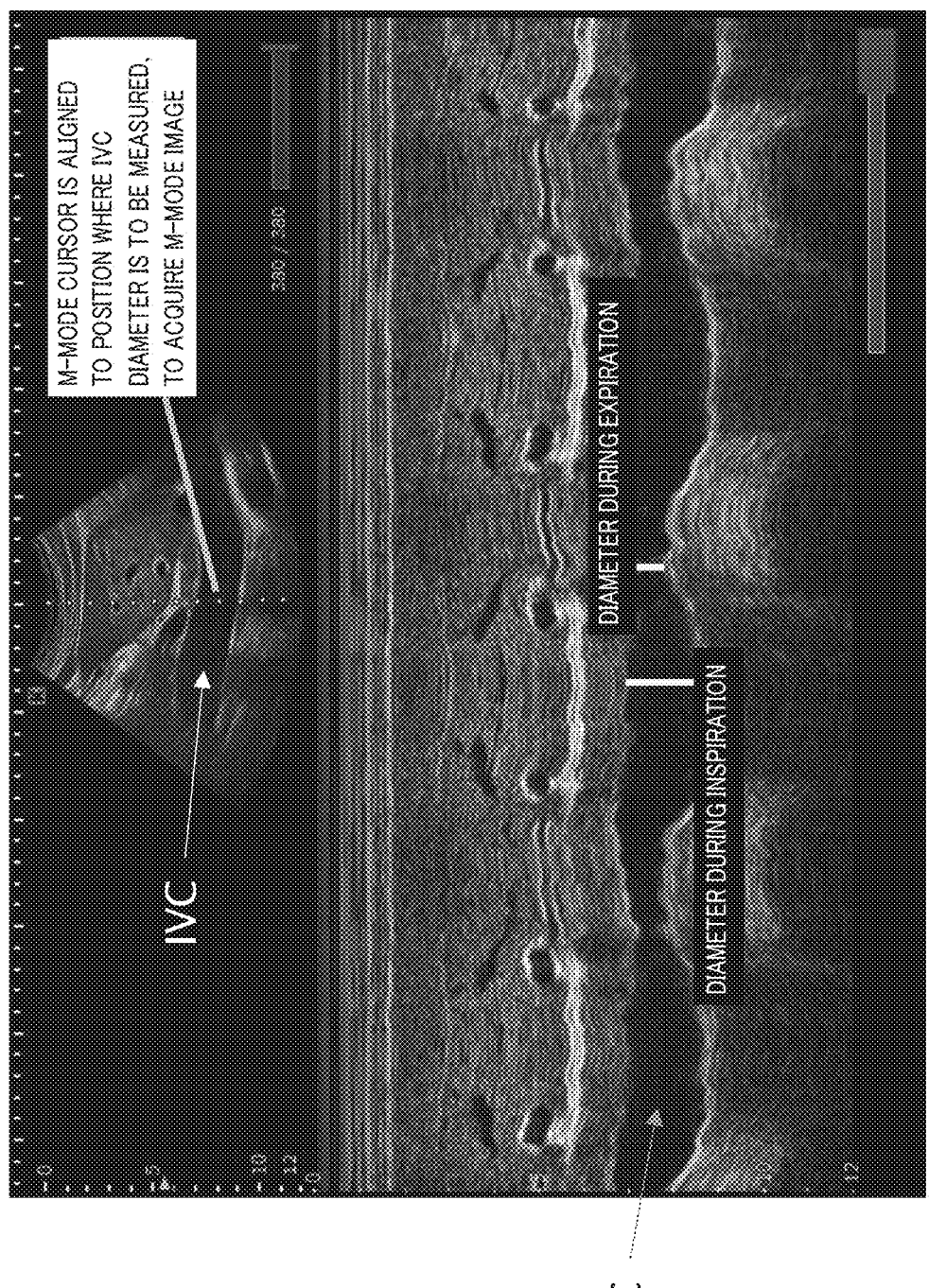
FIG. 52 is a diagram illustrating IVC diameter measurement processing according to an example of the present disclosure.

The machine learning model 10 according to the present example can be used for the inferior vena cava (IIVC) measurement. Here, the IVC diameter can be used to measure the maximum value of the blood vessel diameter of the inferior vena cava and a respiratory fluctuation due to respiration on a B-mode image or an M-mode image. The respiratory fluctuation in the vessel diameter can be expressed by, for example, (maximum size-minimum size)/maximum size×100 [%]. As illustrated in FIG. 52, the maximum diameter is a diameter of the inferior vena cava during expiration, and the minimum diameter is a diameter of the inferior vena cava during inspiration. The IVC diameter can be used as, for example, an index for infusion management. For automatic IVC diameter measurement, the machine learning model 10 is trained to detect the position and width of a blood vessel during expiration and the position and width of a blood vessel during inspiration from the input time-varying image data.

Figure 53:
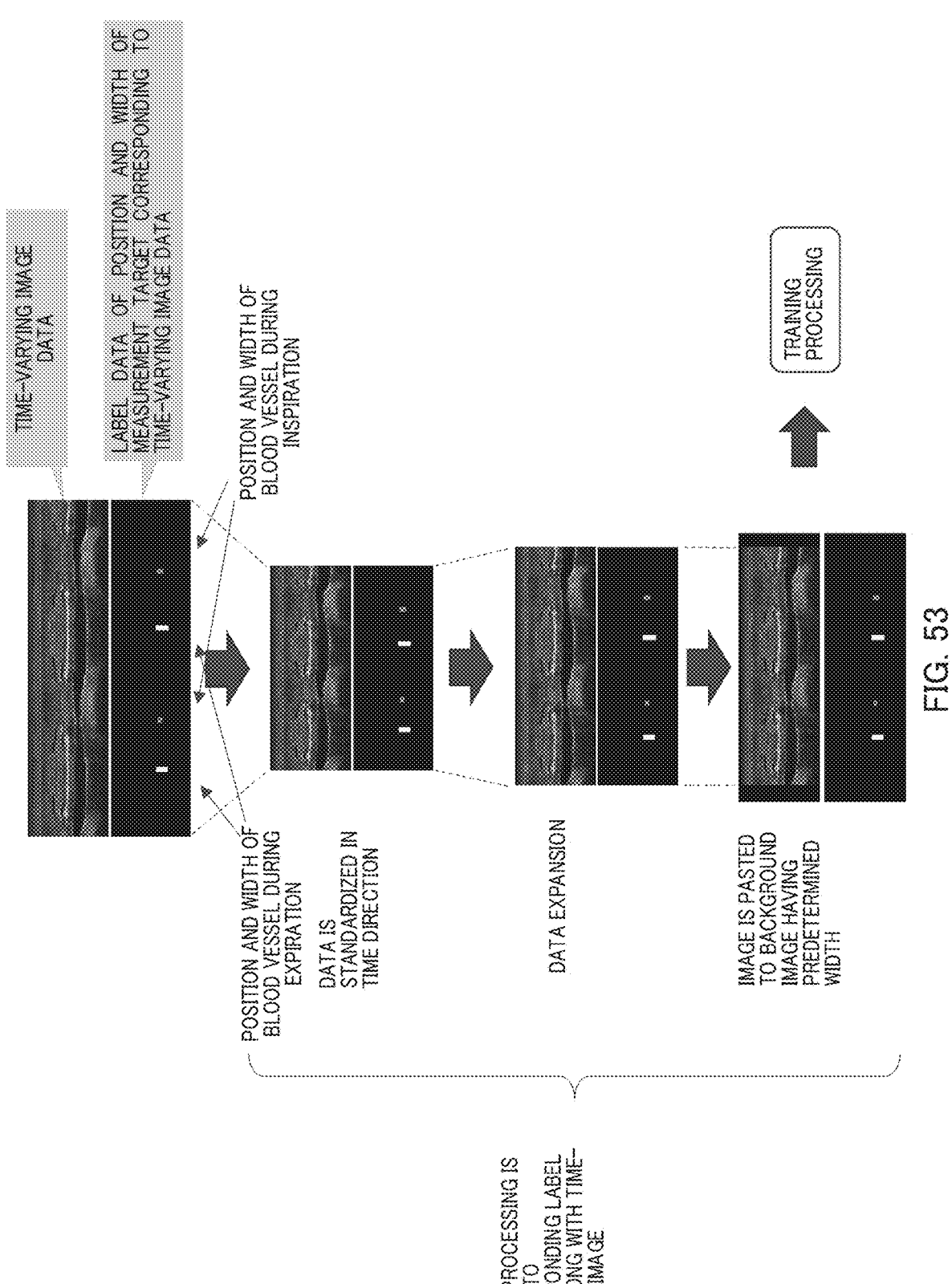
FIG. 53 is a diagram illustrating training processing for IVC diameter measurement according to the example of the present disclosure.

In the training processing of the machine learning model 10, for example, time-varying image data as illustrated in FIG. 53 and label data on the position and width of a blood vessel during expiration and the position and width of a blood vessel during inspiration that correspond to the time-varying image data are prepared as training data. Since the time-varying image data for training is acquired at different sweep speeds, the time-varying image data and the label data are standardized to a predetermined sweep speed and enlarged and/or reduced in the time direction, as described above. Note that since the IVC diameter is not a measurement related to pulsation of the heart but a measurement related to respiratory fluctuation, standardization according to the heart rate is not performed. For example, the time-varying image data and the label data illustrated in FIG. 53 are first reduced in the time direction in order to be standardized to have a predetermined sweep speed. Next, in order to cope with different respiration rates, data may be expanded so as to be enlarged or reduced at a random ratio in the time direction. The time-varying image data and the label data having been enlarged and reduced in this manner are superimposed on the background image so as to have a predetermined width in the time direction. Then, time-varying image data and label data having the predetermined widths are input to the training processing.

Figure 54:
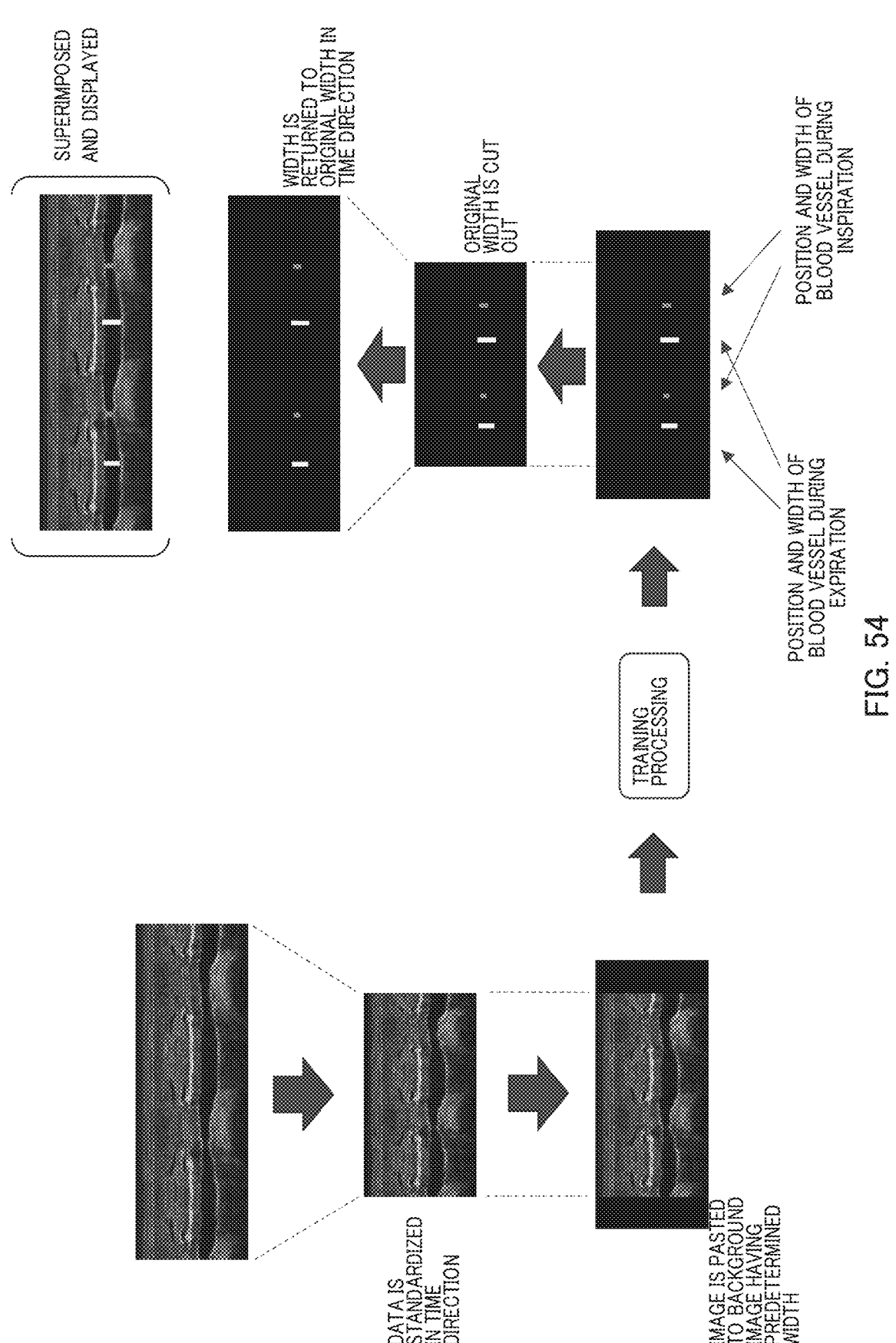
FIG. 54 is a diagram illustrating inference processing for IVC diameter measurement according to the example of the present disclosure.

Next, in the inference processing using the trained machine learning model 10, when time-varying image data of an inference target is provided as illustrated in FIG. 54, the time-varying image data of the inference target is standardized in the time direction and superimposed on the background image so as to have a predetermined width in the time direction. The standardized time-varying image data having a predetermined time width in this manner is input to the trained machine learning model 10, and the position and width of the blood vessel at the time of expiration and the position and width of the blood vessel at the time of inspiration in the standardized time-varying image data are predicted. Thereafter, processing opposite to the preprocessing is performed on the predicted position and width of the blood vessel at expiration and the position and width of the blood vessel at inspiration. That is, the portion of the background image superimposed in the preprocessing is excluded from the position and the width of the blood vessel at the time of expiration and the position and the width of the blood vessel at the time of inspiration, and thereafter, the width is returned to the original width in the time direction. The position and width of the blood vessel at the time of expiration and the position and width of the blood vessel at the time of inspiration acquired in this manner may be superimposed and displayed on the time-varying image data of the inference target.

Figure 55:
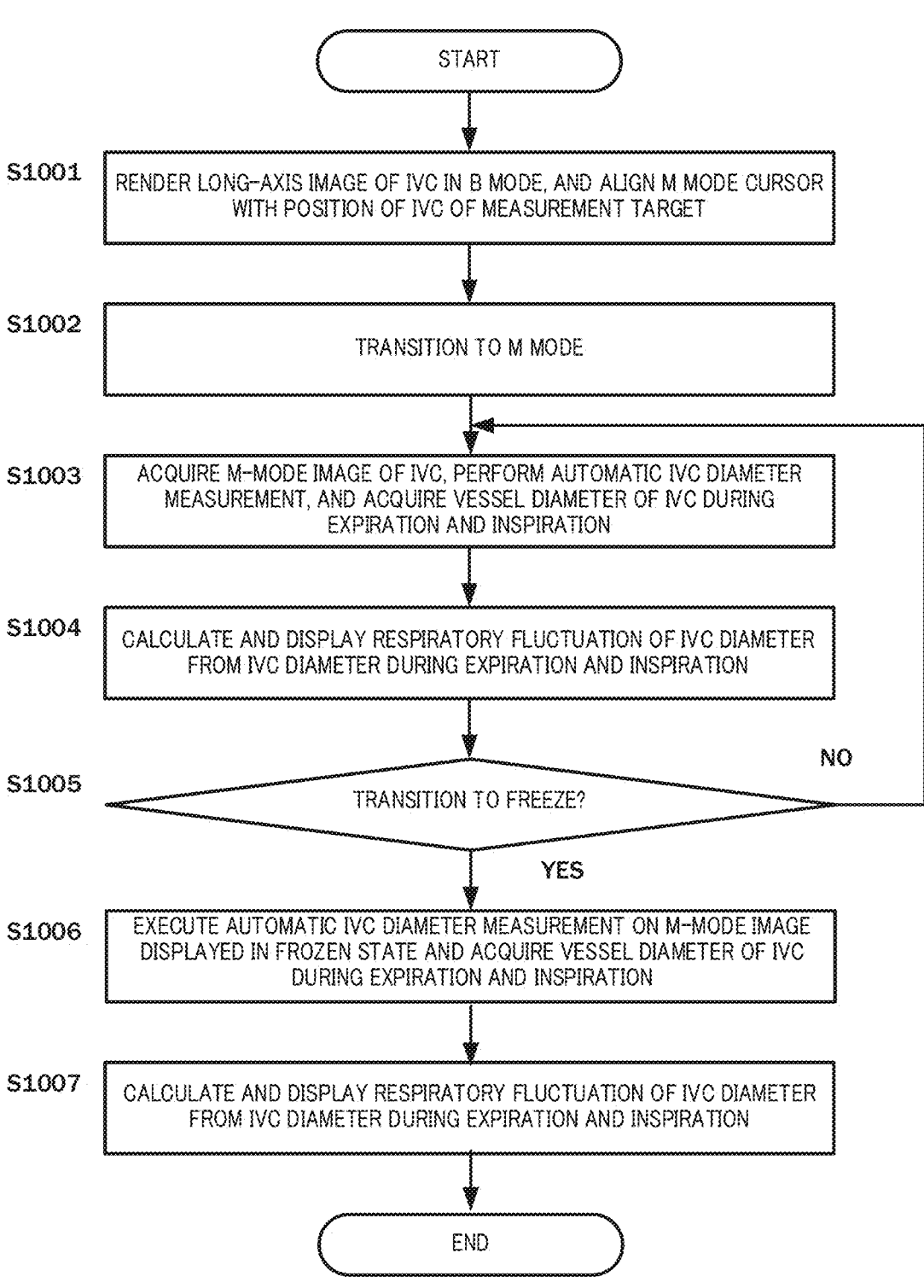
FIG. 55 is a flowchart illustrating IVC diameter measurement processing according to the example of the present disclosure.

FIG. 55 is a flowchart illustrating ultrasound diagnostic processing according to an example of the present disclosure. As illustrated in FIG. 55, in step S1001, the ultrasound diagnostic apparatus 100 renders a long-axis image of the IVC in the B mode, and aligns the M mode cursor with the position of the IVC of the measurement target. For example, the ultrasound diagnostic apparatus 100 is instructed by the user about the position of the M-mode cursor on the rendered long-axis image of the IVC.

In step S1002, the ultrasound diagnostic apparatus 100 transitions to the M mode.

In step S1003, the ultrasound diagnostic apparatus 100 acquires an M-mode image of the IVC, performs automatic IVC diameter measurement on the M-mode image as time-varying image data, and acquires the vessel diameter of the IVC during expiration and inspiration.

In step S1004, the ultrasound diagnostic apparatus 100 calculates the respiratory fluctuation of the IVC diameter from the acquired IVC diameter at the time of expiration and inspiration and displays the respiratory fluctuation.

In step S1005, the ultrasound diagnostic apparatus 100 determines whether the state has transitioned to the freeze state. When the state has not transitioned to the freeze state (S1005: NO), the ultrasound diagnostic apparatus 100 proceeds to step S1003 and repeats the above-described processing. On the other hand, when the state has transitioned to the freeze state (S1005: YES), the ultrasound diagnostic apparatus 100 proceeds to step S1006.

In step S1006, the ultrasound diagnostic apparatus 100 executes automatic IVC diameter measurement on the M-mode image displayed in a frozen state and acquires the blood vessel diameter of the IVC during expiration and inspiration. That is, the ultrasound diagnostic apparatus 100 inputs an M-mode image as time-varying image data of a measurement target to the trained machine learning model 10, and acquires the position and width of the blood vessel at the time of expiration and the position and width of the blood vessel at the time of inspiration from the trained machine learning model 10.

In step S1007, the ultrasound diagnostic apparatus 100 calculates the respiratory fluctuation in the IVC diameter from the acquired blood vessel diameter of the IVC at the time of expiration and at the time of inspiration, and displays the respiratory fluctuation.

In this manner, according to the present example, the IVC diameter automatic measurement is executed using the machine learning model 10 trained by the training data including the standardized time-varying image data, and the position and width of the blood vessel at expiration and the position and width of the blood vessel at inspiration. Based on the estimated, and the position and width of the blood vessel at expiration and the position and width of the blood vessel at inspiration, and the respiratory fluctuation of the IVC diameter can be estimated from the time-varying image data acquired from the subject 30.

Figure 56:
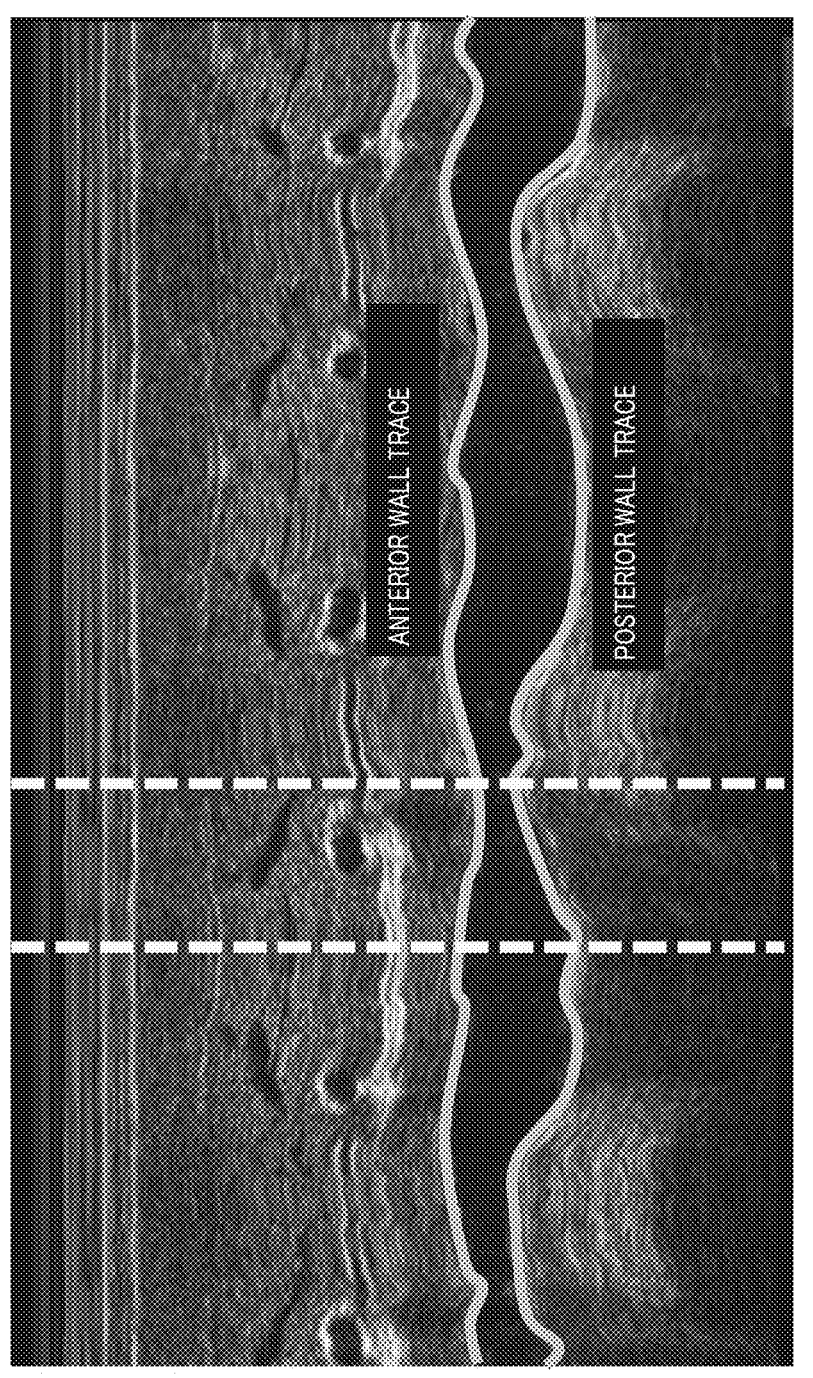
FIG. 56 is a diagram illustrating IVC diameter measurement processing according to the example of the present disclosure.

In the above-described example, from the position and width of the blood vessel at expiration and the position and width of the blood vessel at inspiration and the respiratory fluctuation of the IVC diameter estimated by the IVC diameter automatic measurement are estimated, but the machine learning model 10 according to the present example may be trained to detect the timing of expiration and inspiration of the IVC and the anterior wall and posterior wall traces as illustrated in FIG. 56.

In the training processing of the machine learning model 10, for example, time-varying image data and label data of timing of expiration and timing of inspiration of the IVC corresponding to the time-varying image data are prepared as training data. Since the time-varying image data for training is acquired at different sweep speeds, the time-varying image data and the label data are standardized to a predetermined sweep speed and enlarged and/or reduced in the time direction, as described above. For example, the time-varying image data and the label data are first reduced in the time direction to be standardized to a predetermined sweep speed. Next, in order to cope with different respiration rates, data may be expanded so as to be enlarged or reduced at a random ratio in the time direction. The time-varying image data and the label data having been enlarged and reduced in this manner are superimposed on the background image so as to have a predetermined width in the time direction. Then, time-varying image data and label data having the predetermined widths are input to the training processing. Note that the standardization for the training dataset is similar to that in the above-described example involving the detection of diastolic timing and systolic timing in TAPSE/MAPSE measurement, and details are omitted to avoid redundant description. However, since the IVC diameter is not a measurement related to the pulsation of the heart but a measurement related to the respiratory fluctuation, standardization according to the heart rate is not performed.

Next, in the inference processing using the trained machine learning model 10, when time-varying image data of an inference target is provided, the time-varying image data of the inference target is standardized in the time direction and is superimposed on the background image so as to have a predetermined width in the time direction. The standardized time-varying image data having a predetermined time width in this manner is input to the trained machine learning model 10, and the machine learning model 10 predicts and the timing at the time of expiration and inspiration of the IVC in the standardized time-varying image data. The processing opposite to the preprocessing is then performed on the predicted IVC expiratory and inspiratory timing. That is, the portion of the background image superimposed in the preprocessing is excluded from the expiratory timing and inspiratory timing of the IVC, and then the width is returned to the original width in the time direction. The timing and the timing at the time of expiration and the time of inspiration of the IVC acquired in this manner may be superimposed and displayed on the time-varying image data of the inference target. It is to be noted that the standardization of the inference target data is the same as that in the above-described example relating to the detection of the diastolic timing and systolic timing in the TAPSE/MAPSE measurement, and a detailed description thereof will be omitted in order to avoid a duplicate description.

Further, the machine learning model 10 according to the present example may be trained to detect trace lines of the front wall and the rear wall in the M-mode image, for example. In the training processing of the machine learning model 10, for example, time-varying image data and label data of and trace lines of the front wall and the rear wall corresponding to the time-varying image data are prepared as training data. Since the time-varying image data for training is acquired at different sweep speeds, the time-varying image data and the label data are standardized to a predetermined sweep speed and enlarged and/or reduced in the time direction, as described above. For example, the time-varying image data and the label data are first reduced in the time direction to be standardized to a predetermined sweep speed. The time-varying image data and the label data having been enlarged and reduced in this manner are superimposed on the background image so as to have a predetermined width in the time direction. Then, time-varying image data and label data having the predetermined widths are input to the training processing. Note that the standardization of the training dataset is similar to that in the above-described example of detecting the trace lines of the tricuspid annulus/mitral annulus in TAPSE/MAPSE measurement, and details are omitted to avoid redundant description. However, since the IVC diameter is not a measurement related to the pulsation of the heart but a measurement related to the respiratory fluctuation, standardization according to the heart rate is not performed.

Next, in the inference processing using the trained machine learning model 10, when time-varying image data of an inference target is provided, the time-varying image data of the inference target is standardized in the time direction and is superimposed on the background image so as to have a predetermined width in the time direction. The standardized time-varying image data having a predetermined time width in this manner is input to the trained machine learning model 10, and the machine learning model 10 predicts and the trace lines of the front wall and the rear wall in the standardized time-varying image data. The processing opposite to the preprocessing is then performed on the predicted front and rear wall trace lines. That is, the portion of the background image superimposed in the preprocessing is excluded from the trace lines of the front wall and the rear wall, and then the width is returned to the original width in the time direction, and the trace lines of the front wall and the rear wall acquired in this manner May be superimposed and displayed on the time-varying image data of the inference target. Note that the standardization is the same as in the above-described example relating to the detection of the trace line of the tricuspid annulus/mitral annulus in the TAPSE/MAPSE measurement, and a detailed description thereof will be omitted to avoid a redundant description.

Figure 57:
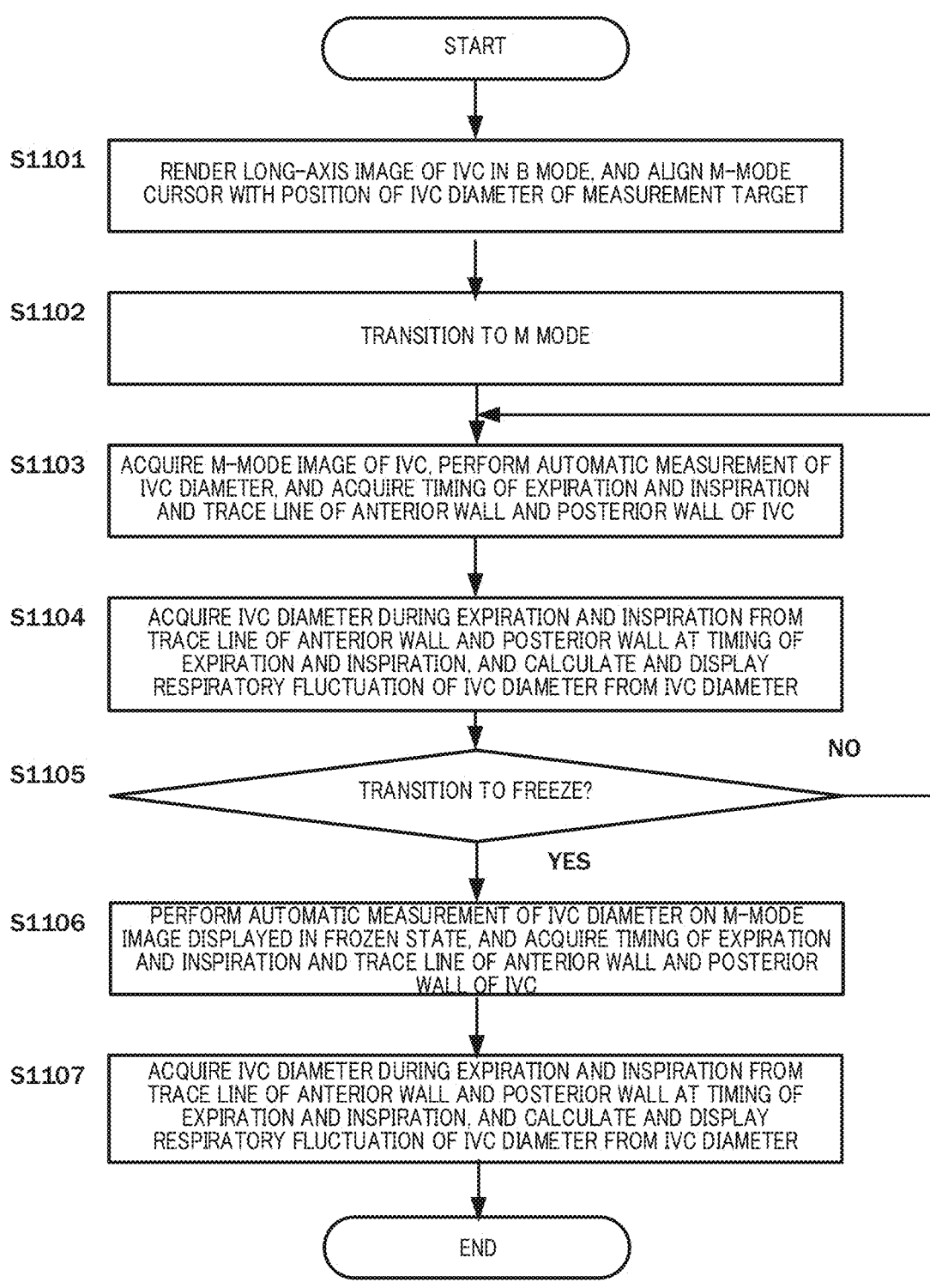
FIG. 57 is a flowchart illustrating IVC diameter measurement processing according to the example of the present disclosure.

FIG. 57 is a flowchart illustrating ultrasound diagnostic processing according to an example of the present disclosure. As illustrated in FIG. 57, in step S1101, the ultrasound diagnostic apparatus 100 renders a long-axis image of the IVC in the B mode, and aligns the M-mode cursor with the position of the IVC of the measurement target. For example, the ultrasound diagnostic apparatus 100 is instructed by the user about the position of the M-mode cursor on the rendered long-axis image of the IVC.

In step S1102, the ultrasound diagnostic apparatus 100 transitions to the M mode.

In step S1103, the ultrasound diagnostic apparatus 100 acquires an M-mode image of the IVC, performs automatic measurement of the IVC diameter on the M-mode image, and acquires the timings of expiration and inspiration and the trace lines of the anterior wall and the posterior wall of the IVC.

In step S1104, the ultrasound diagnostic apparatus 100 acquires the IVC diameters at the time of expiration and at the time of inspiration from the trace lines of the anterior wall and the posterior wall at the acquired timings at the time of expiration and at the time of inspiration, and calculates and displays the respiratory fluctuation from the IVC diameters. That is, the distance between the trace lines of the anterior wall and the posterior wall at the acquired timings of expiration and inspiration is the IVC diameter.

In step S1105, the ultrasound diagnostic apparatus 100 determines whether the state has transitioned to the freeze state. When the state has not transitioned to the freeze state (S1105: NO), the ultrasound diagnostic apparatus 100 proceeds to step S1103 and repeats the above-described processing. On the other hand, when the state has transitioned to the freeze state (S1105: YES), the ultrasound diagnostic apparatus 100 proceeds to step S1106.

In step S1106, the ultrasound diagnostic apparatus 100 performs automatic measurement of the IVC diameter on the M-mode image displayed in a frozen state, and acquires the timings of expiration and inspiration and the trace lines of the anterior wall and the posterior wall of the IVC. That is, the ultrasound diagnostic apparatus 100 inputs an M-mode image as time-varying image data of a measurement target to the trained machine learning model 10, and acquires the timings of expiration and inspiration and the trace lines of the anterior wall and the posterior wall of the IVC from the trained machine learning model 10.

In step S1107, the ultrasound diagnostic apparatus 100 acquires the IVC diameters at the time of expiration and at the time of inspiration from the trace lines of the anterior wall and the posterior wall at the acquired timings at the time of expiration and at the time of inspiration, and calculates and displays the respiratory fluctuation from the IVC diameters. That is, the distance between the trace lines of the anterior wall and the posterior wall at the acquired timings of expiration and inspiration is the IVC diameter.

In this manner, according to the present example, the IVC diameter automatic measurement is executed using the machine learning model 10 trained by the training data including the standardized time-varying image data, and the tracing lines of the anterior and posterior walls and, and based on the estimated, and the tracing lines of the anterior and posterior walls and, the respiratory fluctuation of the IVC diameter can be estimated from the time-varying image data acquired from the subject 30.

According to the above-described example, A machine learning model is trained using training data including a pair of training time-varying image data including time-varying image data standardized by expanding and contracting time-varying image data based on a reception signal for image generation received by an ultrasound probe in the time direction and/or time-varying image data generated based on the standardized time-varying image data, and ground truth data including a detection target corresponding to the training time-varying image data. For example, the machine learning model may be implemented by any type of neural network, such as a convolutional neural network. Furthermore, the time-varying image data based on a signal received by the ultrasound probe may be a Doppler image, an M-mode image, or the like, and the time-varying image data standardized from the time-varying image data may be time-varying image data standardized to a predetermined sweep speed. Further, the time-varying image data generated based on the standardized time-varying image data may be time-varying image data standardized to a predetermined heart rate.

In addition, the detection target by machine learning models may be information related to a feature that is affected by a time change in a time-varying image data. To be more specific, the detection target may be information on the position of one or more points in the time-varying image, information on the width, information on the shape of the waveform, information on the timing, information on the time segment, information on the trace, or the like. For example, when a Doppler image is acquired by the ultrasound diagnostic apparatus, the machine learning model may be trained to detect the following as the detection target:

i) a segment in the time direction of a spectral waveform that is a target of velocity time integral (VTI) measurement or a region of the spectral waveform;

ii) positions or timing on a time axis of peak systolic velocity (PSV) and end diastolic velocity (EDV);

iii) a boundary of a segment in the time direction of a spectral waveform that is a target of blood flow volume measurement; and iv) positions or timing on the time axis of the blood flow velocities of an E wave and an A wave in E/A measurement.

Furthermore, when an M-mode image is acquired by the ultrasound diagnostic apparatus, the machine learning model may be trained to detect the following as a detection target based on the acquired M-mode image.

i) diastolic and systolic positions of an annulus in tricuspid annular plane systolic excursion (TAPSE) measurement or mitral annular plane systolic excursion (MAPSE) measurement, diastolic and systolic timing on a time axis, or a trace of the annulus; and ii) a blood vessel diameter of an inferior vena cava, timing of expiration and inspiration, or traces of an anterior wall and a posterior wall of the inferior vena cava, in M-mode inferior vena cava (IVC) diameter measurement.

Although the examples of the present disclosure have been described in detail above, the present disclosure is not limited to the above-described specific embodiments, and various modifications and changes can be made within the scope of the gist of the present disclosure described in the claims.

Although embodiments of the present invention have been described and illustrated in detail, the disclosed embodiments are made for purposes of illustration and example only and not limitation. The scope of the present invention should be interpreted by terms of the appended claims.

What is claimed is:

1. A method of training a machine learning model comprising the steps of:

obtaining first time-varying image data based on a reception signal for image generation received by an ultrasound probe and label data as ground truth data including a detection target;

generating second time-varying image data by standardizing first time-varying image data in a time direction based on one or both of a sweep speed and a heart rate per predetermined time when the first time-varying image data is generated, or third time-varying image data by deforming and/or further standardizing the second time varying image data in the time direction; and using the second time-varying image data or the third time-varying image data as training time-varying image data to train the machine learning model.

2. The method of training the machine learning model according to claim 1, wherein the detection target is information on a feature that is affected by a time change in a time-varying image.

3. The method of training the machine learning model according to claim 1, wherein the detection target is at least one piece of information selected from information on a position of at least one point in a time-varying image, information on a width, information on a shape of a waveform, information on timing, information on a time segment, and information on a trace.

4. The method of training the machine learning model according to claim 1, wherein the third time-varying image data is data obtained by standardizing the second time-varying image data in the time direction.

5. The method of training the machine learning model according to claim 1, wherein the third time-varying image data is data obtained by deforming the second time-varying image data in the time direction.

6. The method of training the machine learning model according to claim 1, wherein the second time-varying image data is data obtained by standardizing the first time-varying image data in the time direction based on information that affects a time-varying image in the time direction when the first time-varying image data is generated.

7. The method of training the machine learning model according to claim 1, wherein the training time-varying image data is time-varying image data cut out to have a predetermined image width or time-varying image data pasted on background image data having a predetermined image width.

8. The method of training the machine learning model according to claim 1, wherein:

the first time-varying image data is a Doppler image; and the detection target is one of the following i) a segment in the time direction of a spectral waveform that is a target of velocity time integral (VTI) measurement or a region of the spectral waveform, ii) positions or timing on a time axis of peak systolic velocity (PSV) and end diastolic velocity (EDV), iii) a boundary of a segment in the time direction of a spectral waveform that is a target of blood flow volume measurement, and iv) positions or timing on the time axis of the blood flow velocities of an E wave and an A wave in E/A measurement.

9. The method of training the machine learning model according to claim 1, wherein the first time-varying image data is an M-mode image; and the detection target is one of the following i) diastolic and systolic positions of an annulus in tricuspid annular plane systolic excursion (TAPSE) measurement or mitral annular plane systolic excursion (MAPSE) measurement, diastolic and systolic timing on a time axis, or a trace of the annulus, and ii) a blood vessel diameter of an inferior vena cava, timing of expiration and inspiration, or traces of an anterior wall and a posterior wall of the inferior vena cava, in M-mode inferior vena cava (IVC) diameter measurement.

10. The method of training the machine learning model according to claim 1, wherein the step of using the second time-varying image data or the third time-varying image data comprises using ground truth data including a detection target corresponding to the at least one piece of training time-varying image data.

11. A non-transitory computer-readable storage medium storing a program for causing a hardware processor of a computer to, by using the machine learning model trained according to the method of claim 1, implement an output function of outputting, as an inference result, the detection target from second prediction target time-varying image data obtained by standardizing first prediction target time-varying image data in a time direction based on one or both of a sweep speed and a heart rate per predetermined time when the first prediction time-varying image data is generated, the first prediction target time-varying image data being based on the reception signal for image generation received by an ultrasound probe.

12. The non-transitory computer-readable storage medium according to claim 11, wherein the detection target output as the inference result is information on a feature affected by a time change in a time-varying image.

13. The non-transitory computer-readable storage medium according to claim 11, wherein the detection target output as the inference result is at least one piece of information selected from information on a position of at least one point in a time-varying image, information on a width, information on a shape of a waveform, information on timing, information on a time segment, and information on a trace.

14. The non-transitory computer-readable storage medium according to claim 11, wherein the second prediction target time-varying image data is data obtained by standardizing the first prediction target time-varying image data in the time direction based on information that affects a time-varying image in the time direction when the first prediction target time-varying image data is generated.

15. The non-transitory computer-readable storage medium according to claim 11, wherein the second prediction target time-varying image data is time-varying image data cut out to have a predetermined image width or time-varying image data pasted on background image data having a predetermined image width.

16. The non-transitory computer-readable storage medium according to claim 11, wherein:

the first prediction target time-varying image data is a Doppler image; and the detection target output as the inference result is one of the following i) a segment in the time direction of a spectral waveform that is a target of velocity time integral (VTI) measurement or a region of the spectral waveform, ii) positions or timing on a time axis of peak systolic velocity (PSV) and end diastolic velocity (EDV), iii) a boundary of a segment in the time direction of a spectral waveform that is a target of blood flow volume measurement, and iv) positions or timing on the time axis of the blood flow velocities of an E wave and an A wave in E/A measurement.

17. The non-transitory computer-readable storage medium according to claim 11, wherein:

the first prediction target time-varying image data is an M-mode image; and the detection target is one of the following i) diastolic and systolic positions of an annulus in tricuspid annular plane systolic excursion (TAPSE) measurement or mitral annular plane systolic excursion (MAPSE) measurement, diastolic and systolic timing on a time axis, or a trace of the annulus, and ii) a blood vessel diameter of an inferior vena cava, timing of expiration and inspiration, or traces of an anterior wall and a posterior wall of the inferior vena cava, in M-mode inferior vena cava (IVC) diameter measurement.

18. An ultrasound diagnostic apparatus, comprising:

an ultrasound probe that transmits and receives an ultrasonic wave to and from a subject; and a hardware processor that, by using the machine learning model trained according to the method of claim 1, outputs the detection target as an inference result from the second prediction target time-varying image data, the second prediction target time-varying image data being obtained by standardizing first prediction target time-varying image data in a time direction based on one or both of a sweep speed and a heart rate per predetermined time when the first prediction time-varying image data is generated, the first prediction target time-varying image data being based on a reception signal received by the ultrasound probe.

19. An ultrasound diagnostic system, comprising:

a database that stores the machine learning model trained according to the method of claim 1;

an ultrasound probe that transmits and receives an ultrasonic wave to and from a subject; and a hardware processor that, by using the machine learning model, outputs the detection target as an inference result from the second prediction target time-varying image data, the second prediction target time-varying image data being obtained by standardizing first prediction target time-varying image data in a time direction based on one or both of a sweep speed and a heart rate per predetermined time when the first prediction time-varying image data is generated, the first prediction target time-varying image data being based on a reception signal received by the ultrasound probe.

20. An image processing apparatus comprising:

a hardware processor that, by using the machine learning model trained according to the method of claim 1, outputs the detection target as an inference result from the second prediction target time-varying image data, the second prediction target time-varying image data being obtained by standardizing first prediction target time-varying image data in a time direction based on one or both of a sweep speed and a heart rate per predetermined time when the first prediction time-varying image data is generated, the first prediction target time-varying image data being based on a reception signal received by an ultrasound probe.

21. A training apparatus for training a machine learning model by using training data that comprises the following data:

at least one piece of training time-varying image data of second time-varying image data and third time-varying image data, the second time-varying image data being obtained by standardizing first time-varying image data in a time direction, the first time-varying image data being based on a reception signal for image generation received by an ultrasound probe, and the third time-varying image data by deforming and/or further standardizing the second time-varying image data in the time direction, and ground truth data including a detection target corresponding to the at least one piece of training time-varying image data.

* * * * *